US008182816B2

(12) United States Patent
Sanchez-Madrid et al.

(10) Patent No.: US 8,182,816 B2
(45) Date of Patent: May 22, 2012

(54) METHODS OF TREATING CANCER

(75) Inventors: Francisco Sanchez-Madrid, Madrid (ES); Carlos-Martinez Alonso, Madrid (ES); David Sancho Madrid, Madrid (ES); Pablo Engel Rocamora, Barcelona (ES); Enric Esplugues Artola, Barbera del Valles (ES); Javier Vega Ramos, Barcelona (ES); Pilar Lauzurica Gomez, Barcelona (ES)

(73) Assignees: Universidad Autonoma de Madrid, Madrid (ES); Consejo Superior de Investigaciones Cientificas, Madrid (ES); Pilar Lauzurica Gómez, Barcelona (ES)

( * ) Notice: Subject to any disclaimer, the term of this patent is extended or adjusted under 35 U.S.C. 154(b) by 0 days.

(21) Appl. No.: 12/944,338

(22) Filed: Nov. 11, 2010

(65) Prior Publication Data

US 2011/0165071 A1    Jul. 7, 2011

Related U.S. Application Data

(63) Continuation of application No. 10/770,639, filed on Feb. 2, 2004, now Pat. No. 7,867,475.

(30) Foreign Application Priority Data

Jan. 31, 2003  (ES) .................................. 200300252
Nov. 5, 2003   (ES) .................................. 200302587

(51) Int. Cl.
*A61K 39/395* (2006.01)

(52) U.S. Cl. ............... 424/144.1; 424/153.1; 424/154.1; 424/156.1; 424/155.1

(58) Field of Classification Search ........................ None
See application file for complete search history.

(56) References Cited

U.S. PATENT DOCUMENTS 5,643,759 A * 7/1997 Pfreundschuh ............ 435/70.21

FOREIGN PATENT DOCUMENTS

| EP | 1004667 A1 | 5/2000 |
|---|---|---|
| ES | 2192128 A1 | 9/2003 |
| WO | WO-9521618 A1 | 8/1995 |
| WO | WO-0105964 A1 | 1/2001 |
| WO | WO-2004069183 A2 | 8/2004 |

OTHER PUBLICATIONS

Esplugues et al., J. Exp. Med., vol. 197, No. 9, May 5, 2003 1093-1106.*
David Goldenberg, Perspectives on oncologic imaging with radiolabeled antibodies. Cancer. Dec. 15, 1997;80(12 Suppl):2431-5.*
Borrego et al., Immunology 1999, 97, 159-165.*
Hudson et al., Journal of Immunological Methods 231, 1999. 177-189.*
Karre et al. Nature. Feb. 20-26, 1986;319(6055):675-8.*
Fehse et al. "Efficient depletion of alloreactive donor T lymphocytes based on expression of two activation-induced antigens (CD25 and CD69)," Brit. J. of Haematol., 109:644-651 (2000).
D'Arena et al., CD69 Expression in B-cell Chronic Lymphocytic Leukemia: a New Prognostic Marker?, Heamotologica, 86(9):995-996 (2000).
Damale et al., B-cell Chronic Lymphocytic Leukemia Cells Express a Surface Membrane Phenotype of Activated, Antigen-Experienced B Lymphocytes, Blood, 99(11):4087-4093 (2002).
Eichler et al., "Differentially Induced Expression of C-Type Lectins in Activated Lymphocytes", J. Cell. Biochem., Suppl. 36:201-208, J. Clin. Invest., 112:872-882 (2001).
Sansho et al., "CD69 Downregulates Autioimmune Reactivity Through Active Transforming Growth Factor-beta Production in Collagen-Induced Arthritis", 112(6):872-882 (2003).
Choy et al., "Percentage of Anti-CD4 Monoclonal Anti-body Coated Lymphocytes in the Rheumatoid Joint is Associated with Clinical Improvement", Arthri. Rheuma., 39(1):52-56 (1996).
Hamann et al., "AICL: a new activation-induced antigen encoded by the human NK gene cpmplex", Immunogene., 45:295-300 (1997).
Ziegler et al., "Molecular characterization of the early activation antigen CD69: a type II membrane glycoprotein related to a family of natural killer cell activation antigens", Eur. J. Immunol., 23L1643-1648 (1993).
Lopez-Cabrera et al., "Moleular cloning, expression, and chromosomal localization of the human earliest lymphocyte activation AIM/CD69, a new member of the C-type animal lectin superfamily of signal-transmitting receptors", J. Exp. Med., 178:537-547 (1993).
Testi et al., "The CD69 receptor: a multipurpose cell-surface trigger for hematopoietic cells", Immunol.,Today, 15:479-483 (1994).
Long, E.O., "Regulation of Immune Responses through Inhibitory Receptors", Annu. Rev. Immunol., 17:875-904 (1999).
Pisegnan et al., "Src-dependant Syk activation controls CD69-mediated signaling and function on human NK cells", J. Immunol., 169:68-74 (2002).
Zingoni et al., "CD69-triggered ERK activation and functions are negatively regulated by CD94/NKG2-A inhibitory receptor", Eur. J. Immunol., 30:644-651 (2000).
Risso et al., "CD69 in resting and activated T lymphocytes Its association with a GTP binding protein and biochemical requirements for its expression", J. Immunol., 146:4105-4114 (1991).
Bikah et al., "Regulating T helper cell Immunity through antigen responsiveness and clacium entry", Nat. Immunol., 1:402-412 (2000).
Sancho et al., "Functional analysis of ligand-binding and signal transduction domains of CD69 and CD23 C-type lectin leukocyte receptors", 165:3868-3875 (2000).
Testi et al., "T cell activation via Leu-23 (CD69)", J. Immunol., 143:1123-1128 (1989).
Cebrian et al., "Triggering of T cell proliferation through AIM, an activation inducer molecule expressed on activated human lymphocytes", J. Exp. Med., 168:1621-1637 (1998).

(Continued)

*Primary Examiner* — Zachary Skelding
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

Disclosed are methods of treating subjects having cancers including administering an effective amount of an early activation molecule agonist, antagonist or depletor, to the subject. Human monoclonal antibodies specific to the early activation molecules, and methods of use, are also disclosed.

5 Claims, 36 Drawing Sheets

OTHER PUBLICATIONS

Santis et al., "Tumor necrosis factor-a production in T lymphocytes through the AIM/CD69 activation pathway", Eur. J. Immunol., 22:1253-1259 (1992).

De-Maria et al., "Triggering of human monocyte activation through CD69, a member of the natural killer cell gene complex family of signal transducing receptors", J. Exp. Med., 180:1999-2004 (1994).

Testi et al., "CD69 is expreseed on platelets and mediates platelet activation and aggregation", J. Exp. Med., 172:701-707 (1990).

Walsh et al., "Ligation of CD69 induces apoptosis and cell death in human eosinophils cultured with granulocyte-macrophage colony-stimulating factor", Blood, 87:2815-2821 (1996).

Cosulich et al., "Functional characterization of an antigen involved in an early step of T-cell activation", Proc. Natl. Acad. Sci. U.S.A., 84:4205-4209 (1987).

Nakayama et al., "The generation of mature, single-positive thymocytes in vivo is dysregulated by CD69 blockade or overexpression", J. Immunol., 168:87-94 (2002).

Laffon et al., "Upregulated expression and function of VLA-4 fibronectin receptors on human activated T cells in rheumatoid arthritis", J. Clin. Invest., 88:546-552 (1991).

Remmers et al., "A genome scan localizes five non-MHC loci controlling colagen-induced arthritis in rats", Nat. Gent., 14:82-85 (1996).

McIndoe et al., "Localization on non-MHC collagen-induced arthritis susceptibility loci inDBA/1j mice", Proc. Natl. Acad. Sci. USA, 96:2210-2214 (1999).

Brandes et al., "Transforming growth factor b1 suppresses acute and chronic arthritis in experimental animals", J. Clin. Invest., 87:1108-1113 (1991).

Grewal et al., "Serotonin 5-HT2A receptor induces TGF-b1 expression in mesangial cells via ERK: proliferative and fibrotic signals", Am. J. Physiol. Rwnal Physiol., 276:F922-F930 (1999).

Gorelik, L. and Flavell, R.A., "Immune-mediated eradication of tumors through the blockade of transforming growth factor-b signaling in T cells", Nat. Med., 7:1118-1122 (2001).

Gorelik et al., "Mechanism of transforming growth factor b-induced inhibition of T helper type 1 differentiation", J. Med., 195:1499-1505 (2002).

Cazac, B.B and Roes, J., "TGF-b receptor controls B cell responsiveness and induction of IgA in vivo", Immunity, 13:443-451 (2000).

Fava et al., "Transforming growth factor 1 induced neutrophil recruitment to synovial tissues: implications for TGF-b driven synovial inflammation and hyperplasia", J. Exp. Med., 173:1121-1132 (1991).

Sancho et al., "Activation of peripheral blood T cells by interaction and migration through endothelium: role of lymphocyte function antigen-1/intercellular adhesion molecule01 and interleukin-15", Bllod, 93:886-896 (1999).

Fava et al., "Active and latent forms of transforming growth factor b activity in synovial effusions", J. Exp. Med., 169:291-296 (1989).

Yu, X. et al., "Anti-CD69 autoantibodies cross-react with low density lipoprotein receptor-related protein 2 in systemic autoimmune diseases", J. Immunol., 166:1360-1369 (2001).

Kulkarni, A.B. et al., "Transforming growth factor b1 null mutation in mice causes excessive inflammatory response and early death", Proc. Natl. Acad. Sci. U. S. A., 90:770-774 (1993).

Shull, M.M. et al., "Targeted disruption of the mouse transforming growth factor-b1 gene results in multifocal inflammatory disease", Nature, 359:693-699 (1992).

Shevach, E.M., "CD4+CD25+ suppressor T-cells: more questions than answers", Nat. Rev. Immunol., 2:389-400 (2002).

Chatenoud et al., "Induced dominant self-tolerance in overtly diabetic NOD mice", J. Immunol., 158:2947-2954 (1997).

Ishikawa et al., "A subset of CD4C T cells expressing early activation antigen CD69 in murine lupus: possible abnormal regulatory role for cytokine imbalance", J. Immunol., 161: 1267-1273 (1998).

Portales-Perez et al., "Abnormalities in CD69 expression, cytosolic pH and Ca2C during activation of lymphocytes from patients with systemic lupus erythematosus", Lupus, 6:48-56 (1997).

Hernández-García et al., "The CD69 activation pathway in rheumatoid arthritis synovial fluid T cells", Arthritis Rheum., 39:1277-1286 (1996).

McGuirk, P. and Mills, L., "Pathogen-specific regulatory T cells provoke a shift in the Th1/Th2 paradigm in immunity to infectious diseases", Trends Immunol., 23:450-455 (2002).

Swat et al., "CD69 expression during selection and maturation of CD4C8C thymocytes", Eur. J. Immunol., 23:739-746 (1993).

Bendelac et al., "Activation events during thymic selection", J. Exp. Med., 175:731-742 (1992).

Yamashita et al., "CD69 cell surface expression identifies developing thymocytes which audition for T cell antigen receptor mediated positive selection", Int. Immunol., 5:1139-1150 (1993).

Hare et al., "CD69 expression discriminates MHC dependent and -independent stages of thymocyte positive selection", J. Immunol., 162:3978-3983 (1999).

Feng et al., "A potential role for CD69 in thymocyte emigration", Int. Immunol., 14:535-544 (2002).

Lauzurica et al., Phenotypic and functional characteristics of hematopoietic cell lineages in CD69-deficient mice, Blood 95:2312-2320 (2000).

Ramirez et al., "CD69-induced monocyte apoptosis involves multiple nonredundant signaling pathways", Cell. Immunol., 172:192-199 (1996).

Moretta et al., "CD69-mediated pathway of lymphocyte activation: Anti-CD69 monoclonal antibodies trigger the cytolytic activity of different lymphoid effector cells with the exception of cytolytic T lymphocytes expressing T cell receptor α/β", J. Exp. Med., 174:1393-1398 (1991).

* cited by examiner

```
  1  mssencfvae nsslhpesgq endatsphfs trhegsfqvp vlcavmnvvf itiliialia
 61  lsvgqyncpg qytfsmpsds hvsscsedwv gyqrkcyfis tvkrswtsaq nacsehgatl
121  avidsekdmn flkryagree hwvglkkepg hpwkwsngke fnnwfnvtgs dkcvflknte
181  vssmeceknl ywicnkpyk  (SEQ ID NO:2)
```

```
   1 agactcaaca agagctccag caaagacttt cactgtagct tgacttgacc tgagattaac
  61 tagggaatct tgagaataaa gatgagctct gaaaattgtt tcgtagcaga gaacagctct
 121 ttgcatccgg agagtggaca agaaaatgat gccaccagtc cccatttctc aacacgtcat
 181 gaagggtcct tccaagttcc tgtcctgtgt gctgtaatga atgtggtctt catcaccatt
 241 ttaatcatag ctctcattgc cttatcagtg ggccaataca attgtccagg ccaatacaca
 301 ttctcaatgc catcagacag ccatgtttct tcatgctctg aggactgggt tggctaccag
 361 aggaaatgct actttatttc tactgtgaag aggagctgga cttcagccca aatgcttgt
 421 tctgaacatg gtgctactct tgctgtcatt gattctgaaa aggacatgaa ctttctaaaa
 481 cgatacgcag gtagagagga acactgggtt ggactgaaaa aggaacctgg tcacccatgg
 541 aagtggtcaa atggcaaaga atttaacaac tggttcaacg ttacagggtc tgacaagtgt
 601 gtttttctga aaaacacaga ggtcagcagc atggaatgtg agaagaattt atactggata
 661 tgtaacaaac cttacaaata taaggaaac atgttcactt attgactatt atagaatgga
 721 actcaaggaa atctgtgtca gtggatgctg ctctgtggtc cgaagtcttc catagagact
 781 ttgtgaaaaa aatttttata gtgtcttggg aattttcttc caaacagaac tatggaaaaa
 841 aaggaagaaa ttccaggaaa atctgcactg tgggctttta ttgccatgag ctagaagcat
 901 cacaggttga ccaataacca tgcccaagaa tgagaagaat gactatgcaa cctttggatg
 961 cactttatat tattttgaat ccagaaataa tgaaataact aggcgtggac ttactattta
1021 ttgctgaatg actaccaaca gtgagagccc ttcatgcatt tgcactactg gaaggagtta
1081 gatgttggta ctagatactg aatgtaaaca aaggaattat ggctggtaac ataggttttt
1141 agtctaattg aatcccttaa actcagggag catttataaa tggacaaatg cttatgaaac
1201 taagatttgt aatatttctc tcttttaga gaaatttgcc aatttacttt gttattttc
1261 cccaaaaaga atgggatgat cgtgtattta ttttttttact tcctcagctg tagacaggtc
1321 cttttcgatg gtacatattt ctttgccttt ataatctttt atacagtgtc ttacagagaa
1381 aagacataag caaagactat gaggaatatt tgcaagacat agaatagtgt tggaaaatgt
1441 gcaatatgtg atgtggcaaa tctctattag gaaatattct gtaatcttca gacctagaat
1501 aatactagtc ttataatagg tttgtgactt tcctaaatca attctattac gtgcaatact
1561 tcaatacttc atttaaaata tttttatgtg caataaaatg tatttgtttg tattttgtgt
1621 tcagtacaat tataagctgt ttttatatat gtgaataaaa agtagaataa acacaaaaaa
1681 aaaaaaaaaa aaaaaaaaa aa  (SEQ ID NO:1)
```

Fig. 23

```
  1 mmtkhkkcfi ivgvlittni itlivkltrd sqslcpydwi gfqnkcyyfs keegdwnssk
 61 yncstqhadl tiidnieemn flrrykcssd hwiglkmakn rtgqwvhgat ftksfgmrgs
121 egcaylsddg aatarcyter kwicrkrih    (SEQ ID NO:4)

1 ctgtgctgta aaaacaagag taacattttt atattaaagt taaataaagt tacaactttg
 61 aagagagttt ctgcaagaca tgacacaaag ctgctagcag aaaatcaaaa cgctgattaa
121 aagaagcacg gtatgatgac caaacataaa aagtgtttta taattgttgg tgttttaata
181 acaactaata ttattactct gatagttaaa ctaactcgag attctcagag tttatgcccc
241 tatgattgga ttggtttcca aaacaaatgc tattatttct ctaaagaaga aggagattgg
301 aattcaagta aatacaactg ttccactcaa catgccgacc taactataat tgacaacata
361 gaagaaatga attttcttag gcggtataaa tgcagttctg atcactggat tggactgaag
421 atggcaaaaa atcgaacagg acaatgggta catggagcta catttaccaa atcgtttggc
481 atgagaggga gtgaaggatg tgcctacctc agcgatgatg gtgcagcaac agctagatgt
541 tacaccgaaa gaaaatggat ttgcaggaaa agaatacact aagttaatgt ctaagataat
601 ggggaaaata gaaaataaca ttattaagtg taaaccagc aaagtacttt tttaattaaa
661 caaagttcga gttttgtacc tgtctggtta attctgctta cgtgtcaggc tacacataaa
721 agccacttca aagattggca aaaaaaaaaa aaaaaaaa   (SEQ ID NO:3)
```

Fig. 24

```
  1 mhdsnnvekd itpselpanp gclhskehsi katliwrlff limfltiivc gmvaalsair
 61 anchqepsvc lqaacpeswi gfqrkcfyfs ddtknwtssq rfcdsqdadl aqvesfqeln
121 fllrykgpsd hwiglsreqg qpwkwingte wtrqfpilga gecaylndkg assarhyter
181 kwicsksdih v    (SEQ ID NO:6)
```

```
  1 gaattccggc aaaatgcatg acagtaacaa tgtggagaaa gacattacac catctgaatt
 61 gcctgcaaac ccaggttgtc tgcattcaaa agagcattct attaaagcta ccttaatttg
121 gcgcttattt ttcttaatca tgtttctgac aatcatagtg tgtggaatgg ttgctgcttt
181 aagcgcaata agagctaact gccatcaaga gccatcagta tgtcttcaag ctgcatgccc
241 agaaagctgg attggttttc aaagaaagtg tttctatttt tctgatgaca ccaagaactg
301 gacatcaagt cagaggtttt gtgactcaca agatgctgat cttgctcagg ttgaaagctt
361 ccaggaactg aatttcctgt tgagatataa aggcccatct gatcactgga ttgggctgag
421 cagagaacaa ggccaaccat ggaaatggat aaatggtact gaatggacaa gacagtttcc
481 tatcctggga gcaggagagt gtgcctattt gaatgacaaa ggtgccagta gtgccaggca
541 ctacacagag aggaagtgga tttgttccaa atcagatata catgtctaga tgttacagca
601 aagccccaac taatctttag aagcatattg gaactgataa ctccatttta aaatgagcaa
661 agaatttatt tcttatacca acaggtatat gaaaatatgc tcaatatcac taataactgg
721 gaaaatacaa atcaaaatca tagtaaaata ttacctgttt tcatggtgct aatattacct
781 gttctcccac tgctaatgac atacccgaga atgagtaatt tataaataaa agagatttaa
841 ttgaaaaaaa    (SEQ ID NO:5)
```

Fig. 25

METHODS OF TREATING CANCER

RELATED APPLICATIONS

This application is a continuation of U.S. patent application Ser. No. 10/770,639, filed Feb. 2, 2004, which claims the benefit of priority to ES200302587, filed on Nov. 5, 2003, and ES200300252, filed Jan. 31, 2003, each of which are incorporated herein by reference in their entireties.

TECHNICAL FIELD OF THE INVENTION

This invention relates to the use of members of the NK gene complex family of type II oligomeric signal transmitting receptor proteins containing a C-type lectin-binding domain to modulate a subject's immune response.

BACKGROUND OF THE INVENTION

Immune-mediated diseases are an emerging field of pharmacological treatment that includes autoimmune diseases, which affect approximately 5% of the population (O'Shea et al., 2002), graft rejection, allergy, atherosclerosis, infectious diseases and tumoral processes that are one major cause of mortality in industrialized countries. Therefore, the regulation of the immune response is key for the treatment of the major causes of morbidity and mortality in our society.

CD69 is expressed early and transiently following leukocyte activation after an immune challenge (Cebrian et al., 1988; Hara et al., 1986; Testi et al., 1994) in all hematopoietic subsets except erythrocytes. Although, CD69 is detected in vivo on small subsets of T and B cells in peripheral lymphoid tissues (Sanchez-Mateos et al., 1989), CD69 is persistently expressed in leukocyte infiltrates of several chronic inflammatory diseases such as rheumatoid arthritis, and viral-chronic hepatitis (García-Monzón et al., 1990; Laffon et al., 1991), in leukocytes responsible for graft rejection (Mampaso et al., 1993), in leukocytes involved in the allergic response (Hartnell et al., 1993), in immune cells at the atherosclerotic lesion (Caspar-Bauguil et al., 1998), in tumor infiltrating lymphocytes (Coventry et al., 1996), or upon persistent infection (Zajac et al., 1998). Several reports suggest that CD69 is involved in activation of bone marrow-derived cells (Cebrian et al., 1988; Testi et al., 1994). Nevertheless, nearly normal hematopoietic cell development and T cell maturation occur in CD69$^{-/-}$ mice under physiological conditions (Lauzurica et al., 2000).

CD69, together with two other proteins, activation-induced C-type lectin (AICL) and Lectin-like transcript (LLT1), form part of the NK complex. (Hamann et al., 1997; Boles et al., 1999). Expression of all three of these proteins, CD69, AICL and LLT1, is upregulated at early time points of cellular activation. (Eichler et al., 2001).

Autoimmune diseases are characterized by the presence of abnormal and persistent leukocyte activation that contributes to disease pathogenesis. It is well established that cytokines have essential roles in the pathogenesis of autoimmune diseases (Falcone and Sarvetnick, 1999). Therefore, the targeting of these cytokines is currently the preferred strategy in the new treatments for autoimmune disease. In this regard, tumor necrosis factor (TNF) appears to be at the top of the pro-inflammatory cascade, and anti-TNF therapy has been revealed as a useful tool for the treatment of RA (Feldmann, 2002). In addition, other cytokines have demonstrated an opposite anti-inflammatory effect. Thus, administration of TGF-β1 has beneficial effects in several autoimmune diseases (Prud'homme and Piccirillo, 2000), depressing pro-inflammatory cytokine production in arthritis (Kuruvilla et al., 1991), allergic encephalomyelitis (Chen et al., 1994), colitis (Powrie et al., 1996), and autoimmune diabetes (Piccirillo et al., 1998).

The immune response against tumors behaves as "an effective extrinsic tumor-suppressor system" that involves the combined action of humoral and cellular mechanisms, in which lymphocytes and cytokines prevent primary tumor development (Dighe A S, 1994; Kaplan D H, 1998; Shankaran V, 2001; Smyth and Godfrey, 2000; Smyth et al., 2000; van den Broek M E, 1996). Cytokine action, at least in part directed at regulating tumor cell immunogenicity, is critical for the tumor suppressor function of the immune system. Advanced tumors and metastases down-regulate class I MHC expression, becoming susceptible to NK cell killing, and therefore, NK cells recognize and destroy cancer cells. In addition, NK cells secrete cytokines, such as TGF-β and IFN-γ that drive differentiation of activated CD4 T cells into Th1 helper effector cells. In this regard, IFNγ helps to prevent tumor formation, as increased spontaneous neoplasic diseases are developed in IFNRγR$^{-/-}$ mice (Dighe A S, 1994; Kaplan D H, 1998). In addition, TGF-β has an important immuno-suppressive role, thus inhibiting anti-tumor immune response. TGF-β prevents and/or suppresses immune responses, regulating production of proinflammatory cytokines, reviewed in (Letterio and Roberts, 1998) and the inhibitory effect of TGF-β in the cytokine network is dependent on both cell stage and cytokine milieu. TGF-β has been implicated in the modulation of anti-tumor effector mechanisms by altering activation, proliferation and cytotoxicity of immune cells, macrophages, NK and T cells (Gorelik and Flavell, 2000; Kehrl et al., 1986). Recently, it has been reported that blockade of TGF-β signaling in T cells enhances anti-tumor immunity by facilitating an expansion of tumor specific CD8$^+$ T cells (Gorelik and Flavell, 2001). In addition, other cytokines are important regulators of recruitment, proliferation, differentiation and survival of anti-tumor effector cells. MCP-1 produced by many cells activates cell recruitment, and animals that lack MCP-1 show diminished T cell responses (Allavena et al., 1994; Carr et al., 1994; Gu et al., 1997). Therefore, cytokines have essential roles in inducing anti-tumor immunity, and targeting cytokines provides effective therapy in human and several murine models (Gill P S, 1995).

However, the fibrogenic and other detrimental effects of TGF-β1 may limit its immunotherapeutic use in humans (Border and Ruoslahti, 1992). TGF-β has been implicated in several pathologic conditions and its systemic use has oncogenic potential, which may explain the increased number of tumors seen in patients treated with cyclosporin, a drug which enhances systemic TGF-β production (Hojo et al., 1999). Therefore, the local regulation of TGF-β1 should result in an effective treatment of chronic inflammatory diseases by avoiding the detrimental consequences of systemic TGF-β1.

Hence, CD69, AICL, and LLT1 may represent targets for immunotherapy in diseases whereby leukocytes express high levels of these activation markers. It follows that it would be desirable to develop specific antibodies to target such molecules for use in human therapy, e.g., in treating diseases associated with the presence of activated cells expressing one or more of these antigens.

Although murine monoclonal antibodies (mAbs) are relatively easy to produce, and some mouse mAbs to anti-human CD69 are now available, there are many restrictions for their therapeutic use in humans, due to their immunogenicity and to the resulting reduction in their efficacy and safety (Jakobovits, 1995). These restrictions could be overcome by the use of fully human mAbs, which would allow their repeated administration without immunogenic and/or allergic responses. Thus, the development of transgenic mice strains, engineered with unrearranged human immunoglobulin (Ig) genes, has become a good strategy for the generation of specific human mAbs.

SUMMARY OF THE INVENTION

The invention is based, in part, on the discovery that modulation of CD69, AICL and/or LLT1 can be used to modulate a subject's immune response and, thus can be used to treat a variety of disorders. CD69, AICL and LLT1 agonists, CD69, AICL and LLT1 antagonists and depletors of CD69-, AICL- and LLT1-expressing cells are all useful, as is described below. CD69, AICL and LLT1 and the nucleic acids encoding them are referred to herein as "early activation molecules".

Accordingly, in one aspect, the invention features methods of treating a subject, e.g., a subject having a disorder characterized by an unwanted immune response. The disorder can be characterized by a "normal" response, or by an immune response that is increased as compared with what is normally seen in a subject. Examples of such disorders are provided herein and include acute or chronic inflammatory disorders, and immune disorders, e.g., autoimmune disorders. The method includes administering an effective amount of one or more early activation molecule agonist to the subject. (Unless other wise indicated, the use of the term agonist, or antagonist, can refer to an agent which exerts an effect at the level of nucleic acid, protein, or both.)

Examples of early activation molecule agonists include, but are not limited to: CD69, AICL, and LLT1 polypeptides, peptides, peptidomimetics or functional fragments thereof; nucleic acids which encode a CD69, an AICL or a LLT1 polypeptide or functional fragments thereof, agents which increase the expression of endogenous CD69, AICL or LLT1, e.g., an agent which increases transcription of CD69, AICL or LLT1 (e.g., an agent which binds to an early activation molecule promoter and increases transcription), small molecules which bind to an early activation molecule and agonize its activity, an agonist anti-CD69 antibody molecule, an agonist anti-AICL antibody molecule and an agonist anti-LLT1 antibody molecule. Examples of small molecules include, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organometallic compounds) having a molecular weight less than about 5,000 grams per mole, organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of other early activation molecule agonists include, but are not limited to: agonist CD69 receptor (CD69R) polypeptides, peptides, peptidomimetics, agonist AICL receptor (AICL-R) polypeptides, peptides and peptidomimetics, agonist LLT1 receptor (LLT1-R) polypeptides, peptides and peptidomimetics, soluble forms of CD69R, soluble forms of AICL-R, soluble forms of LLT1-R, agonist CD69R, AICL-R, or LLT1-R fusion proteins, e.g., an early activation protein receptor-serum protein fusion protein (e.g., CD69R-immunoglobulin fusion proteins, CD69R-human serum albumin fusion proteins, AICL-R-immunoglobulin fusion proteins, AICL-R-human serum albumin fusion proteins, LLT1-R-immunoglobulin fusion proteins, LLT1-R-human serum albumin fusion proteins), or other forms of agonist early activation protein receptor fusion proteins designed to increase serum half-life and/or multivalency. Preferred agonists are anti-early activation protein antibody molecules (e.g., anti-CD69 antibody molecules, anti-AICL antibody molecules and anti-LLT1 antibody molecules), early activation proteins receptor polypeptides, e.g., CD69R fragments, AICL-R fragments, LLT1-R fragments, CD69R fusion proteins, AICL-R fusion proteins, and LLT1-R fusion proteins. Antibody molecules which increase an early activation molecule activity include, but are not limited to, antibody molecules which interact with, e.g., bind to, an early activation polypeptide and result in a change in interaction, e.g., binding activity, of the early activation polypeptide with an early activation polypeptide binding partner (e.g., the antibody molecule can affect the conformation of an epitope of the early activation polypeptide, thereby resulting in increased interaction, e.g., binding, by an early activation polypeptide binding partner to the epitope), an antibody which binds an early activation polypeptide and increases clustering of the protein (e.g., an IgM which binds an early activation polypeptide), and any CD69 antibody, AICL antibody or anti-LLT1 antibody, e.g., an art known antibody, which can act as an agonist.

In a preferred embodiment, the antibody is a human monoclonal antibody that specifically targets an early activation molecule, e.g., hAIM-29 specific for the human CD69 antigen.

In some embodiments, the subject has an inflammatory disease, e.g., an acute or chronic inflammatory disease. Examples of inflammatory diseases include, but are not limited to: acute lung injury, acute respiratory distress syndrome, arthritis (e.g., CIA), asthma, bronchitis, cystic fibrosis, autoimmune diabetes, encephalomyelitis, hepatitis (e.g., viral chronic hepatitis), inflammatory bowel disease, multiple sclerosis, reperfusion injury (e.g., myocardial), nephritis, pancreatitis, psoriasis, artery occlusion (e.g., retinal), stroke, systemic lupus erythematosus, transplantation (e.g., host mediated rejection of transplant, e.g., transplanted tissue such as hematopoietic stem cells or an organ, e.g., a kidney, or graft mediated host response, e.g., graft v. host disease), ultraviolet light induced injury, and/or vasculitis. The inflammatory disease may be acute or chronic, and is preferably mediated by leukocytes. In some embodiments, the inflammatory disease is associated with chronic inflammation, e.g., the disease is inflammatory bowel disease, such as Crohn's disease and ulcerative colitis, psoriasis, sarcoidosis and rheumatoid arthritis.

In a preferred embodiment, the method includes administering one or more early activation molecule agonist in combination with a second therapeutic agent, e.g., a therapeutic agent or agent for treating inflammation. The second agent can be an antibody or an agent other than an antibody.

The subject can be a mammal, e.g., a primate, preferably a higher primate, e.g., a human.

In some embodiments, the early activation molecule agonist can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes. In some embodiments, the early activation molecule agonist can be administered prior to or during a secondary immune response in the subject.

In a preferred embodiment, the early activation molecule agonist is administered on a repeated basis. E.g., the agonist can be administered 2, 4, 6, or more times. Administration can be repeated until improvement in subject condition is seen or expected. Administration of an antibody can be at a frequency of about once, every 5 to 7 days, 14 to 30 or 30 to 60 days. Administration of other compounds can be administered more frequently. For example, a small molecule can be administered one, two, three, four or more times a day.

In another aspect, the invention features methods of treating a subject, e.g., a subject having a disorder characterized by an unwanted immune response. The disorder can be characterized by an immune response that is increased as compared with what is normally seen in a subject. Examples of such disorders are provided herein and include acute or chronic inflammatory disorders, and immune disorders, e.g., autoimmune disorders. The method includes administering an effective amount of a depletor of an early activation polypeptide-expressing cell to the subject, e.g., a cell expressing one or more of CD69, AICL and LLT1.

Examples of early activation molecule depletors include, those described herein, but are not limited to, antibody molecules which bind CD69 and deplete CD69 expressing cells, e.g., an anti-human CD69 antibody analogous to the anti-mouse CD69 antibody 2.3 or any CD69 antibody, e.g., an art known antibody which can act as a depletor (or an antibody molecule based thereon, e.g., a fragment, chimeric, humanized, or deimmunized antibody), an antibody molecule which binds the epitope bound by such an antibody, an antibody molecule which competes for binding with such an antibody; antibody molecules which bind AICL and deplete AICL expressing cells, e.g., any AICL antibody, e.g., an art known antibody, which can act as a depletor (or an antibody molecule based thereon, e.g., a fragment, chimeric, humanized, or deimmunized antibody), an antibody molecule which binds the epitope bound by such an antibody, an antibody molecule which competes for binding with such an antibody; antibody molecules which bind LLT1 and deplete LLT1 expressing cells, e.g., any LLT1 antibody, e.g., an art known antibody which can act as a depletor (or an antibody molecule based thereon, e.g., a fragment, chimeric, humanized, or deimmunized antibody), an antibody molecule which binds the epitope bound by such an antibody, an antibody molecule which competes for binding with such an antibody; or an antibody molecule identified by a method described herein. In a preferred embodiment, the anti-human CD69 antibody is a human monoclonal antibody, e.g., hAIM-29. In another embodiment, a depleting anti-early activation polypeptide antibody molecule (e.g., a depleting anti-CD69 antibody molecule, a depleting anti-AICL antibody molecule or a depleting anti-LLT1 antibody molecule) can recruit an immune cell (e.g., by way of an Fc receptor or by recruitment of the complement system) and inactivate or kill the target cell, e.g., the early activation polypeptide-expressing cell. Thus, in another embodiment, a depleting anti-early activation polypeptide antibody can activate the classical complement pathway that leads to the lysis of the target cell (e.g., the CD69-, AICL-, and/or LLT1-expressing cell). In another embodiment, the depletor is an anti-early activation polypeptide antibody molecule which is coupled to a therapeutic, e.g., a protein, drug or isotope, which can inactivate or kill the target cell, e.g., the CD69-, AICL- and/or LLT1-expressing cell.

In some embodiments, the subject has an inflammatory disease, e.g., an acute or chronic inflammatory disease. Examples of inflammatory diseases include, but are not limited to: acute lung injury, acute respiratory distress syndrome, arthritis (e.g., CIA), asthma, bronchitis, cystic fibrosis, autoimmune diabetes, encephalomyelitis, hepatitis (e.g., viral chronic hepatitis), inflammatory bowel disease, multiple sclerosis, reperfusion injury (e.g., myocardial), nephritis, pancreatitis, psoriasis, artery occlusion (e.g., retinal), stroke, systemic lupus erythematosus, transplantation (e.g., host mediated rejection of transplant, e.g., transplanted tissue such as hematopoietic stem cells or an organ, e.g., a kidney, or graft mediated host response, e.g., graft v. host disease), ultraviolet light induced injury, and/or vasculitis. The inflammatory disease may be acute or chronic, and is preferably mediated by leukocytes. In some embodiments, the inflammatory disease is associated with chronic inflammation, e.g., the disease is inflammatory bowel disease, such as Crohn's disease and ulcerative colitis, psoriasis, sarcoidosis and rheumatoid arthritis.

In a preferred embodiment, the method includes administering one or more depletor of early activation polypeptide-expressing cells in combination with a second therapeutic agent, e.g., a therapeutic agent or agent for treating inflammation. The second agent can be an antibody or an agent other than an antibody.

The subject can be a mammal, e.g., a primate, preferably a higher primate, e.g., a human.

In some embodiments, the early activation molecule depletor can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes. In some embodiments, the early activation molecule depletor can be administered prior to or during a secondary immune response in the subject.

In a preferred embodiment, early activation molecule depletor is administered on a repeated basis. E.g., the depletor can be administered 2, 4, 6, or more times. Administration can be repeated until improvement in subject condition is seen or expected. Administration of an antibody can be can be at a frequency of about once, every 5 to 7 days, 14 to 30 or 30 to 60 days. Administration of other compounds can be administered more frequently. For example, a small molecule can be administered one, two, three, four or more times a day.

In another aspect, the invention features, methods of treating a subject, e.g., a subject in need of, or a subject that would benefit from, an increased or augmented immune response. The subject can have a disorder characterized by a decreased immune response, e.g., an immune response that is decreased as compared to what is seen in the absence of a disorder, e.g., the subject could have an immunodeficiency. In other embodiments, the subject does not have a decreased or compromised immune response but would never the less benefit from an increased or augmented immune response. For example, the subject could have a disorder characterized by unwanted cells or tissue or characterized by unwanted cell proliferation, such as cancer. The method can also be used to increase or augment an immune response in a subject, e.g., an immune response to an antigen (e.g., a vaccine). The method includes administering one or more early activation molecule antagonist (e.g., a CD69 antagonist, an AICL antagonist, an LLT1 antagonist or combinations thereof) to the subject.

Examples of early activation molecule antagonists include, but are not limited to, antisense of an early activation molecule (e.g., antisense of CD69, AICL or LLT1), RNAi targeted to an early activation molecule, an antagonist anti-CD69 antibody molecule, an antagonist anti-AICL antibody molecule, an antagonist anti-LLT1 antibody molecule, and other compounds identified by a method described herein, e.g., compounds that interact with one or more of CD69, AICL and LLT1 and decrease TGF-θ expression in a cell, and small molecules which bind to an early activation molecule and antagonize its activity. Examples of small molecules include, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organomettallic compounds) having a molecular weight less than about 5,000 grams per mole, organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of other early activation molecule antagonist include, but are not limited to: antagonist CD69 receptor (CD69R) polypeptides, peptides, peptidomimetics; antagonist AICL receptor (AICL-R) polypeptides, peptides, peptidomimetics; antagonist LLT1 receptor (LLT1-R) polypeptides, peptides, peptidomimetics; soluble forms of CD69R; soluble forms of AICL-R; soluble forms of LLT1-R; antagonist CD69R, AICL-R or LLT1-R fusion proteins, e.g., early activation polypeptide-serum protein fusion protein (e.g., CD69R-immunoglobulin fusion proteins, CD69R-human serum albumin fusion proteins, AICL-R-immunoglobulin fusion proteins, AICL-R-human serum albumin fusion proteins, LLT1-R-immunoglobulin fusion proteins, LLT1-R-human serum albumin fusion proteins), or other forms of antagonist early activation polypeptide receptor fusion proteins designed to increase serum half-life and/or multivalency. Antagonist anti-early activation polypeptide antibody molecules include, but are not limited to, antibody molecules that bind an early activation polypeptide and interfere with binding of the early activation polypeptide and an early activation polypeptide binding polypeptide and antibody molecules that bind an early activation polypeptide and decrease the level of the early activation polypeptide on a cell surface, e.g., by internalization of the early activation polypeptide. Antagonist anti-CD69 antibody molecules include, but are not limited to, antibody molecules which bind CD69 and interfere with binding of CD69 to a CD69 binding partner and antibody molecules which bind CD69 and decrease the level of CD69 on a cell surface. Examples of antagonist anti-CD69 antibody molecules include an anti-human CD69 antibody, e.g., an anti-human CD69 antibody analogous to the anti-mouse CD69 antibody 2.2 or an anti-CD69 antibody, e.g., an art known antibody, which can act as an antagonist (or an antibody molecule based thereon, e.g., a fragment, chimeric, humanized, or deimmunized antibody) or an antibody molecule which binds the epitope bound by such an antibody, an antibody molecule which competes for binding with such an antibody, or an antibody molecule which binds to or interferes with the binding of another antibody, receptor or ligand to one or more of amino acid residues Glu 140, Asp171, Glu 180, Glu 185, Glu 187, Phe 175, Met 184, Leu 190, Glu 185 and Lys188 of human CD69. In a preferred embodiment, the anti-human CD69 antibody is a human monoclonal antibody, e.g., hAIM-29. Antagonist anti-AICL antibody molecules include, but are not limited to, antibody molecules which bind AICL and interfere with binding of AICL to an AICL binding partner and antibody molecules which bind AICL and decrease the level of AICL on a cell surface. Examples of antagonist anti-AICL antibody molecules include an anti-human AICL antibody, e.g., an anti-AICL antibody, e.g., an art known antibody, which can act as an antagonist (or an antibody molecule based thereon, e.g., a fragment, chimeric, humanized, or deimmunized antibody) or an antibody molecule which binds the epitope bound by such an antibody, an antibody molecule which competes for binding with such an antibody, or an antibody molecule which binds to or interferes with the binding of another antibody, receptor or ligand to one or more of amino acid residues of 37 to 149 of human AICL. Antagonist anti-LLT1 antibody molecules include, but are not limited to, antibody molecules which bind LLT1 and interfere with binding of LLT1 to a LLT1 binding partner and antibody molecules which bind LLT1 and decrease the level of LLT1 on a cell surface. Examples of antagonist anti-LLT1 antibody molecules include an anti-human LLT1 antibody, e.g., an anti-LLT1 antibody, e.g., an art known antibody, which can act as an antagonist (or an antibody molecule based thereon, e.g., a fragment, chimeric, humanized, or deimmunized antibody) or an antibody molecule which binds the epitope bound by such an antibody, an antibody molecule which competes for binding with such an antibody, or an antibody molecule which binds to or interferes with the binding of another antibody, receptor or ligand to one or more of amino acid residues of 76 to 132 of human LLT1.

In some embodiments, the subject has a disease characterized by unwanted malignant or non-malignant cellular proliferation, e.g., cancer. Examples of cancers include, but are not limited to, biliary tract cancer; brain cancer; breast cancer; cervical cancer; choriocarcinoma; colon cancer; endometrial cancer; esophageal cancer; gastric cancer; intraepithelial neoplasms; leukemias (e.g., B-cell chronic lymphocytic leukemia, e.g., B-cell chronic lymphocytic leukemia lacking immunoglobulin mutations), lymphomas; liver cancer; lung cancer (e.g. small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas. In one embodiment, the cancer is not a CD69, AICL and/or LLT1 expressing cancer. In another embodiment, the cancer is B-cell chronic lymphocytic leukemia lacking immunoglobulin mutation and the subject is administered an early activation molecule antagonist, e.g., an AICL antagonist.

In a preferred embodiment, the method includes administering an early activation molecule antagonist in combination with a second agent, e.g., with one or more therapeutic agents, e.g., a therapeutic agent or agent for treating unwanted cell proliferation. The second agent can be an antibody or a non-antibody agent. Therapeutic agents include, for example, one or more of a chemotherapeutic agent, a radioisotope, and a cytotoxin. Examples of chemotherapeutic agents include taxol, cytochalasin B, gramicidin D, mitomycin, etoposide, tenoposide, vincristine, vinblastine, colchicin, busulfan, cisplatin, doxorubicin, daunorubicin, dihydroxy anthracin dione, mitoxantrone, mithramycin, chlorambucil, gemcitabine, actinomycin, procaine, tetracaine, lidocaine, propranolol, puromycin, maytansinoids and analogs or homologs thereof. Additional therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioisotopes can include alpha, beta and/or gamma emitters. Examples of radioisotopes include $^{212}$Bi, $^{213}$Bi, $^{131}$I, $^{211}$At, $^{186}$Re, $^{90}$Y and $^{117}$Lu. The early activation molecule antagonist can be administered prior to, concurrent with or after administration of the therapeutic agents.

In one embodiment, the subject has an immunodeficiency, e.g., an acquired immunodeficiency (e.g., AIDS), a hereditary immunodeficiency, or an immunodeficiency induced or caused by exposure to an environmental or medicinal agent (e.g., a chemotherapeutic agent or radiation treatment).

In another embodiment, the subject has a non-pathologic hyperproliferative disorder, e.g., fibrosis. The fibrotic disorder can be associated with one or more of: trauma, surgery, infection, environmental pollutants, tobacco, alcohol or other toxins. The disorder can be associated with, e.g., one or more of: overabundant wound repair (e.g., hypertrophic scars and keloids), renal fibrosis (proliferation of mesangial cells), liver fibrosis (proliferation of liver stellate cells). Examples of fibrotic disorders include: keloids, burns, hypertrophic scars or other skin disorders (e.g., local or systemic scleroderma, e.g., scleroderma systemic sclerosis), liver cirrhosis, kidney fibrosis (e.g., related to diabetes and/or hypertension), surgical adhesions (e.g., from gastrointestinal surgery or neurosurgery adhesions), vascular grafts, indiopathic pulmonary fibrosis, radiation-induced fibrosis, asbestos-related fibrosis (e.g., black or brown lung), fibrosis associated with viral hepatitis, macular degeneration, retinal and vitreal retinopathy, and fibrosis associated with acute respiratory syndrome. The fibrosis can be acute or chronic fibrosis. Examples of acute fibrosis include: accidental injury, infections, surgery, burns, radiation-induced fibrosis and chemotherapy induced fibrosis. Chronic fibrosis can be associated, e.g., with viral infection, diabetes, and hypertension.

The subject can be a mammal, e.g., a primate, preferably a higher primate, e.g., a human (e.g., a patient having an inflammatory disorder).

In some embodiments, the early activation molecule antagonist can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes. In a preferred embodiment the early activation molecule antagonist is administered on a repeated basis. E.g., the antagonist can be administered 2, 4, 6, or more times. Administration can be repeated until improvement in subject condition is seen or expected. Administration of an antibody can be can be at a frequency of about once, every 5 to 7 days, 14 to 30 or 30 to 60 days. Administration of other compounds can be administered more frequently. For example, a small molecule can be administered one, two, three, four or more times a day.

In another aspect, the invention features methods of enhancing the immune response to an antigen, e.g., a vaccine. The method includes administering to a subject an antigen, e.g., a vaccine, and/or DNA encoding an antigen, and an early activation molecule antagonist, to thereby enhance immune response to the antigen by the subject.

Examples of early activation molecule antagonists include those described herein.

In some embodiments, the early activation molecule antagonist is an anti-early activation polypeptide antibody molecule, e.g., an anti-CD69 antibody molecule, an anti-AICL antibody molecule, an anti-LLT1 antibody molecule (e.g., an antagonist anti-CD69 antibody molecule, an antagonist anti-AICL antibody molecule or an antagonist anti-LLT1 antibody molecule described herein). In a preferred embodiment, the anti-CD69 antibody is a human monoclonal antibody, e.g., hAIM-29.

Examples of doses of antigen that can be used include 100 μg of antigen for primary immunization and, at least 21 days later, 100 μg of antigen in a secondary immunization. The expected titers should be higher at least for Th1-type isotypes such as mouse IgG2a, IgG2b, and IgG3 or their analogous human isotypes.

Examples of vaccines can include, cancer vaccines (e.g., melanoma vaccines, sarcoma vaccines, breast cancer vaccines, prostate cancer vaccines, colorectal cancer vaccines, pancreatic cancer vaccines, and liver cancer vaccines), HIV vaccines, hepatitis vaccines (e.g., type A, B or C), malaria vaccines, herpes vaccines, papilloma vaccines (e.g., HPV-6, 11, 16, 18, 31, 33 and/or 45) and small pox vaccines.

The early activation molecule antagonist can be administered to the subject, prior to, concurrent with or after the administration of the antigen and/or a nucleic acid encoding the antigen.

In another aspect, the invention features methods of treating or preventing an early activation molecule-expressing cancer in a subject, e.g., a CD69-, AICL- and/or LLT1-expressing cancer in a subject. The method includes administering an early activation molecule depletor and/or an early activation molecule antagonist to the subject.

Examples of early activation molecule expressing cancers include: lymphomas (e.g., T-cell lymphomas (e.g., peripheral T-cell lymphomas (Dorfman et al. 2002, Hum. Pathol. 33:330-4) e.g., cutaneous T cell lymphoma (Berti et al., 1991. J. Invest. Dermatol. 96:718-23)), B-cell lymphomas, non-Hodgkin's lymphomas (e.g., T- or B-cell non-Hodgkin's lymphoma (Erlanson et al., 1998. Eur. J. Haematol. 60:125-32)), and lymphocytic leukemias (e.g., T- or B-cell chronic lymphocytic leukemia (Damle et al. 2002, Blood 99:4087-93), e.g., B-cell chronic lymphocytic leukemia lacking immunoglobulin mutations (Klein et al., 2001 J. Exp. Med. 11:1625; Rosenwald et al., 2001 J. Exp. Med. 11:1639)) and other tumors of hematopoietic origin (Tassone et al. 1996. Tissue Antigens 48:65-8).

Early activation molecule depletors include, those described herein, but are not limited to, antibody molecules which bind an early activation molecule and deplete early activation molecule-expressing cells. Examples of early activation molecule depletors include, but are not limited to, antibody molecules which bind CD69 and deplete CD69-expressing cells, e.g., an anti-human CD69 antibody analogous to the anti-mouse CD69 antibody 2.3 or any CD69 antibody, e.g., an art known antibody which can act as a depletor (or an antibody molecule based thereon, e.g., a fragment, chimeric, humanized, or deimmunized antibody), an antibody molecule which binds the epitope bound by such an antibody, an antibody molecule which competes for binding with such an antibody; antibody molecules which bind AICL and deplete AICL-expressing cells, e.g., any AICL antibody, e.g., an art known antibody which can act as a depletor (or an antibody molecule based thereon, e.g., a fragment, chimeric, humanized, or deimmunized antibody), an antibody molecule which binds the epitope bound by such an antibody, an antibody molecule which competes for binding with such an antibody; antibody molecules which bind LLT1 and deplete LLT1-expressing cells, e.g., any LLT1 antibody, e.g., an art known antibody which can act as a depletor (or an antibody molecule based thereon, e.g., a fragment, chimeric, humanized, or deimmunized antibody), an antibody molecule which binds the epitope bound by such an antibody, an antibody molecule which competes for binding with such an antibody; or an antibody molecule identified by a method described herein. In a preferred embodiment, the anti-human CD69 antibody is a human monoclonal antibody, e.g., hAIM-29. In another embodiment, a depleting anti-early activation polypeptide antibody molecule can recruit an immune cell (e.g., by way of an Fc receptor or by recruitment of the complement system) and inactivate or kill the target cell, e.g., the early activation polypeptide-expressing cell. Thus, in another embodiment, a depleting anti-early activation polypeptide antibody molecule can activate the classical complement pathway that leads to the lysis of the target cell (e.g., the CD69-expressing cell). In another embodiment, the depletor is an anti-early activation polypeptide antibody molecule which is coupled to a therapeutic, e.g., a protein, drug or isotope, which can inactivate or kill the target cell, e.g., the early activation polypeptide expressing cell.

In a preferred embodiment, the method includes administering an early activation molecule depletor in combination with a second agent, e.g., with one or more therapeutic agents, e.g., a therapeutic agent or agent for treating cancer. The second agent can be an antibody or a non-antibody agent. Therapeutic agents include, for example, one or more of a chemotherapeutic agent, a radioisotope, and a cytotoxin. Examples of chemotherapeutic agents include taxol, cytochalasin B, gramicidin D, mitomycin, etoposide, tenoposide, vincristine, vinblastine, colchicin, busulfan, cisplatin, doxorubicin, daunorubicin, dihydroxy anthracin dione, mitoxantrone, mithramycin, chlorambucil, gemcitabine, actinomycin, procaine, tetracaine, lidocaine, propranolol, puromycin, maytansinoids and analogs or homologs thereof. Additional therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioisotopes can include alpha, beta and/or gamma emitters. Examples of radioisotopes include $^{212}$Bi, $^{213}$Bi, $^{131}$I, $^{211}$At, $^{186}$Re, $^{90}$Y and $^{117}$Lu. The early activation molecule depletor can be administered prior to, concurrent with or after administration of the therapeutic agents.

The subject can be a mammal, e.g., a primate, preferably a higher primate, e.g., a human (e.g., a patient having an early activation polypeptide-expressing cancer).

In some embodiments, the early activation molecule depletor can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

In a preferred embodiment the early activation molecule depletor is administered on a repeated basis. E.g., the depletor can be administered 2, 4, 6, or more times. Administration can be repeated until improvement in subject condition is seen or expected. Administration of an antibody can be can be at a frequency of about once, every 5 to 7 days, 14 to 30 or 30 to 60 days. Administration of other compounds can be administered more frequently. For example, a small molecule can be administered one, two, three, four or more times a day.

The invention further includes compositions including monoclonal antibodies that bind an epitope presented by the amino acid of SEQ ID NO:2, or a fragment thereof. The epitope can be presented on the extracellular region of the protein, for example, but is an epitope other than that recognized by the antibody of TP1/55. In one embodiment, the monoclonal antibody can be a human antibody and possess an isotype of IgM/λ. The human monoclonal antibody can include, for example, hAIM-29, which is specifically targeted to human CD69 antigens. In a further aspect, the invention includes monoclonal antibodies that recognize native forms of CD69 molecules expressed, or over-expressed, on activated peripheral blood mononuclear cells (PBMC), or other such activated cells, e.g., inflammatory cyokines and cells producing autoimmune antibodies. Such antibodies do not recognize, however, naïve immune cells lacking CD69 expression. In one embodiment, monoclonal antibodies of the invention can cause an increase in intracellular calcium concentration when binding such cells. Such monoclonal antibodies can also enhance the phorbyl myristate acetate (PMA)-induced proliferative activities of PBMC, or other activated cell, expressing, or over-expressing, CD69 surface antigen.

Also included in the invention are kits for detecting an early activation molecule in a biological sample. The sample is preferably from a human subject believed to possess a disorder or condition characterized by an unwanted immune response. The biological sample can include, for example, biological fluid, e.g., blood or other suitable fluid, or tissue. In one embodiment, the kit can include a container having monoclonal antibodies contemplated by the invention, and instructions for using the monoclonal antibody for the purpose of binding to an early activation molecule to form an immunological complex, and detecting the complex such that the presence or absence of the complex correlates to the presence or absence of an early activation molecule in the biological sample. In another embodiment the kit can include hAIM-29, which is specific to human CD69 antigens, as the monoclonal antibody.

The invention also includes methods for treating a subject having a disorder or condition characterized by an unwanted immune response, whereby an effective amount of at least one monoclonal antibody contemplated by the instant invention is administered, alone or conjugated to a second therapeutic agent, to a subject in need thereof. In one embodiment the monoclonal antibody can be a human antibody specific against human CD69, e.g., hAIM-29. The second therapeutic agent can include, by way of example, any of the chemotherapeutic agents, radioisotopes, or cytotoxins previously described herein.

In another aspect, the invention features a method for identifying a compound which modulates an early activation molecule, e.g., a CD69, an AICL or an LLT1 agonist, a CD69, an AICL, or an LLT1 antagonist or a CD69, an AICL or an LLT1 depletor, to thereby modulate an immune response. The method includes: contacting a cell which expresses an early activation molecule with a compound (e.g., a compound which interacts with, e.g., binds to, the early activation molecule), and determining the effect of the compound on expression of the early activation molecule and/or an early activation molecule activity. Expression of an early activation molecule can be determined, e.g., by determining expression of a nucleic acid encoding an early activation polypeptide, expression of an early activation polypeptide, and/or expression of an early activation polypeptide on the surface of a cell.

In a preferred embodiment, the method includes: contacting an early activation polypeptide, e.g., CD69, AICL, or LLT1, or a soluble form of the early activation polypeptide (e.g., a soluble form of CD69, e.g., a CD69 polypeptide which lacks the transmembrane and/or cytoplasmic region of CD69; a soluble form of AICL, e.g., a AICL polypeptide which lacks the transmembrane and/or cytoplasmic region of AICL; a soluble form of LLT1, e.g., a soluble form of LLT1 which lacks the transmembrane and/or cytoplasmic region of LLT1), with a compound, and evaluating the ability of the compound to interact with, e.g., bind to, the early activation polypeptide or soluble early activation polypeptide.

A compound which increases an early activation molecule expression and/or activity (e.g., an early activation molecule agonist) can be identified as a compound which reduces immune response. In a preferred embodiment, the early activation molecule activity which is increased is expression of TGF-θ. In one embodiment, a compound can be evaluated for the ability to increase an early activation molecule expression and/or activity, by methods known in the art, including evaluating the early activation molecule expression and/or an early activation molecule activity of the cell, e.g., expression of TGF-θ, in the absence and presence of the compound. Preferably, the compound interacts with, e.g., binds to, the early activation molecule. Possible compounds include, e.g., small molecules, e.g., small molecules described herein, peptides, fusion proteins, e.g., CD69R fusion proteins, AICL-R fusion protein, and LLT1-R fusion proteins such as those described herein, antibody molecules, and nucleic acid molecules. Antibody molecules which increase an early activation molecule activity include, but are not limited to, antibody molecules, or intrabodies which interact with, e.g., bind to, the early activation polypeptide and result in a change in interaction, e.g., binding activity, of an early activation polypeptide binding partner (e.g., the antibody, intrabody or fragment thereof can affect the conformation of an epitope of the early activation polypeptide, thereby resulting in increased interaction, e.g., binding, by an early activation polypeptide binding partner to the epitope), an antibody molecule which binds the early activation polypeptide and increasing clustering of the polypeptide (e.g., an IgM which binds an early activation polypeptide), and any CD69, AICL or LLT1 antibody molecule, e.g., an art known antibody which can act as an agonist. In some embodiments, the cell-based assay measures an activity of the early activation polypeptide, e.g., increased expression of TGF-θ, MAPK activation, increased $Ca^{2+}$ signalling and/or increased dimer formation of an early activation polypeptide such as CD69, AICL or LLT1. Compounds which increase expression of TGF-θ and/or dimer formation can be selected as early activation molecule agonists. In other embodiments, the cell based assay measures modulation, e.g., an increase, of an early activation molecule expression. For example, an early activation polypeptide expression or nucleic acid (e.g., mRNA or cDNA) expression, in the presence of the compound can be evaluated and compared to expression of the early activation molecule in the cell prior to administration of the compound. An increase in the expression level is any statistically significant increase in an early activation molecule expression levels. Compounds selected can be confirmed as an agonist. In one embodiment, a compound which increases an early activation molecule expression and/or increases an early activation molecule activity, e.g., expression of TGF-θ, of the cell is selected, e.g., selected for further screening, e.g., by administering the compound to a subject, e.g., an animal model, e.g., an animal model for an inflammatory disease (e.g., chronic or acute inflammatory disease), and/or an animal model for an immune disorder, e.g., an autoimmune disorder. An example of an animal model for an inflammatory disease includes a mouse model of collagen-induced arthritis.

A compound which reduces an early activation molecule expression and/or activity can be identified as a compound which increases the immune response. In a preferred embodiment, the early activation molecule activity which is decreased is expression of TGF-θ and/or inhibition dimer formation of the early activation polypeptide, e.g., dimer formation of CD69, AICL, or LLT1. In one embodiment, a compound can be evaluated for the ability to decrease expression of an early activation molecule and/or activity, by methods known in the art, including evaluating expression of the early activation molecule (e.g., nucleic acid, polypeptide and/or cell surface expression) and/or an early activation molecule activity of the cell, e.g., expression of TGF-θ, in the absence and presence of the compound. Preferably, the compound interacts with, e.g., binds to, the early activation molecule. Possible compounds include, e.g., small molecules (e.g., small molecules described herein), peptides, fusion polypeptides (e.g., a CD69R fusion protein, an AICL-R fusion protein or an LLT1-R fusion protein described herein), antibody molecules, and nucleic acid molecules. Examples of antibody molecules include, but are not limited to, antibody molecules, or intrabodies which bind an early activation polypeptide and interfere with binding of the early activation polypeptide and an early activation binding polypeptide and antibody molecules which bind to an early activation polypeptide and decrease the level of the early activation polypeptide on a cell surface, e.g., by internalization. Examples of anti-CD69 antibody molecules include, e.g., an anti-human CD69 antibody, e.g., an anti-human CD69 antibody analogous to an anti-mouse CD69 antibody 2.2 or an anti-human CD69 antibody, e.g., an art known antibody, which can act as an antagonist (or antibody molecules based thereon), an antibody molecule which binds the epitope bound by such antibodies, an antibody molecule which competes for binding with such antibodies, an antibody molecule which binds or interferes with binding of another antibody, receptor or ligand to one or more of amino acid residues Glu 140, Asp171, Glu 180, Glu 185, Glu 187, Phe 175, Met 184, Leu 190, Glu 185 and Lys188 of human CD69, or other antibody described herein. Examples of anti-AICL antibody molecules include an anti-human AICL antibody, e.g., an anti-AICL antibody, e.g., an art known antibody which can act as an antagonist (or an antibody molecule based thereon, e.g., a fragment, chimeric, humanized, or deimmunized antibody) or an antibody molecule which binds the epitope bound by such an antibody, an antibody molecule which competes for binding with such an antibody, or an antibody molecule which binds to or interferes with the binding of another antibody, receptor or ligand to one or more of amino acid residues of 37 to 149 of human AICL, or other antibody described herein. Examples of anti-LLT1 antibody molecules include an anti-human LLT1 antibody, e.g., an anti-LLT1 antibody, e.g., an art known antibody which can act as an antagonist (or an antibody molecule based thereon, e.g., a fragment, chimeric, humanized, or deimmunized antibody) or an antibody molecule which binds the epitope bound by such an antibody, an antibody molecule which competes for binding with such an antibody, or an antibody molecule which binds to or interferes with the binding of another antibody, receptor or ligand to one or more of amino acid residues of 76 to 132 of human LLT1, or other antibody molecule described herein. In some embodiments, the cell-based assay measures an activity of an early activation molecule, e.g., decreased expression of TGF-θ, decreased MAPK, decreased $Ca^{2+}$ signaling and/or decreased dimer formation such as decreased CD69, AICL or LLT1 dimer formation. Compounds which decrease expression of TGF-θ and/or dimer formation can be selected as early activation molecule antagonists. In other embodiments, the cell based assay measures modulation, e.g., a decrease, of an early activation molecule expression. For example, early activation polypeptide expression or nucleic acid (e.g., mRNA or cDNA) expression, in the presence of the compound can be evaluated and compared to expression of the early activation molecule in the cell prior to administration of the compound. A decrease in the expression level is any statistically significant decrease in an early activation molecule expression levels. In other embodiments, the cell based assay measures modulation, e.g., decreased levels, of the early activation polypeptide on the cell surface, e.g., as compared to the levels of the early activation polypeptide on the cell surface prior to administration of the compound.

In one embodiment, a compound which inhibits expression of an early activation molecule and/or inhibits an early activation molecule activity, e.g., expression of TGF-θ, of the cell is selected, e.g., selected for further screening, e.g., by administering the compound to a subject, e.g., an animal model, e.g., an animal model for unwanted cellular proliferation (e.g., an animal model for cancer), an animal model for an immunodeficiency, and/or an animal model of vaccine efficacy.

In another aspect, the invention features a method of identifying a compound which modulates immune response. The method includes: screening for a compound that interacts with, e.g., binds to, an early activation polypeptide or an early activation nucleic acid (e.g., the regulatory region for an early activation gene), and determining the effect of the compound on expression of the early activation molecule and/or an early activation molecule activity, e.g., TGF-θ expression and/or dimer formation, e.g., CD69, AICL or LLT1 dimer formation.

In one embodiment, the interaction between the compound and the early activation polypeptide is evaluated in vitro, e.g., using an isolated early activation polypeptide, e.g., a soluble form of an early activation polypeptide, e.g., a soluble CD69, a soluble AICL or a soluble LLT1 described herein. The early activation polypeptide and/or compound can be in solution (e.g., a micelle) or bound to a solid support, e.g., a column, bead, well or dish, or a chip (e.g., a microarray). In some embodiments, the method is repeated one or more times such that, e.g., a library of test compounds can be evaluated.

In another embodiment, the interaction between the compound and an early activation molecule is evaluated using a cell-based assay.

In a preferred embodiment, a compound which interacts with, e.g., binds to, the early activation molecule, is contacted with a cell which expresses the early activation molecule to determine the effect of the compound on expression of the early activation molecule and/or activity.

In one embodiment, the method includes identifying a compound which interacts with the early activation molecule and increases expression of the early activation molecule and/or an early activation molecule activity, e.g., increases TGF-θ expression, MAPK activation, increased $Ca^{2+}$ signalling and/or dimer formation to thereby identify the compound as a candidate for decreasing immune response. In a preferred embodiment, the early activation molecule activity which is increased is expression of TGF-θ. In one embodiment, a compound can be evaluated for the ability to increase expression of an early activation molecule and/or activity, by methods known in the art, including evaluating expression of an early activation molecule and/or an early activation molecule activity of the cell, e.g., expression of TGF-θ, in the absence and presence of the compound. Possible compounds include, e.g., small organic molecules (e.g., small molecules described herein), peptides, fusion peptides (e.g., a CD69R fusion protein, an AICL-R fusion protein, or a LLT1-R fusion protein, e.g., as described herein), antibody molecules, and nucleic acid molecules. Antibodies which increase an early activation molecule activity include, but are not limited to, antibody molecules or intrabodies which interact with, e.g., bind to, an early activation polypeptide and result in a change in interaction, e.g., binding activity, of an early activation polypeptide binding partner (e.g., the antibody molecule or intrabody can affect the conformation of an epitope of the early activation polypeptide, thereby resulting in increased interaction, e.g., binding, by an early activation polypeptide binding partner to the epitope), an antibody molecule which binds an early activation polypeptide and increases clustering of the early activation polypeptide (e.g., an IgM which binds an early activation polypeptide), and any CD69 antibody molecule, AICL antibody molecule or LLT1 antibody molecule, e.g., from an art known antibody which can act as an agonist. In some embodiments, the cell-based assay measures an activity of an early activation molecule, e.g., increased expression of TGF-θ, increased MAPK, increased $Ca^{2+}$ signalling and/or increased dimer formation of the early activation polypeptide. Compounds which increase expression of TGF-θ, increased MAPK, increased $Ca^{2+}$ signalling and/or CD69 dimer formation can be selected as early activation molecule agonists. In other embodiments, the cell based assay measures modulation, e.g., an increase, of expression of an early activation molecule. For example, an early activation polypeptide expression or nucleic acid (e.g., mRNA or cDNA) expression, in the presence of the compound can be evaluated and compared to expression the early activation molecule in the cell prior to administration of the compound. An increase in the expression level is any statistically significant increase in the expression levels of an early activation molecule.

In one embodiment, a compound which increased expression of an early activation molecule and/or increases an early activation molecule activity, e.g., expression of TGF-θ, of the cell is selected, e.g., selected for further screening, e.g., by administering the compound to a subject, e.g., an animal model, e.g., an animal model for an inflammatory disease (e.g., chronic or acute inflammatory disease), and/or an animal model for an immune disorder, e.g., an autoimmune disorder. An example of an animal model for an inflammatory disease includes a mouse model of collagen-induced arthritis.

In another embodiment, the method includes identifying a compound which interacts with an early activation molecule and decreases expression of the early activation molecule and/or an early activation molecule activity, e.g., decreases TGF-θ expression, decreases MAPK, decreased $Ca^{2+}$ signalling and/or dimer formation, e.g., CD69, AICL or LLT1 dimer formation, to thereby identify the compound as a candidate for increasing immune response. Expression of an early activation molecule can be determined, e.g., by determining expression of a nucleic acid encoding an early activation polypeptide, expression of an early activation polypeptide, and/or expression of an early activation polypeptide on the surface of a cell. In a preferred embodiment, the early activation molecule activity which is decreased is expression of TGF-θ. In one embodiment, a compound can be evaluated for the ability to decrease expression of the early activation molecule and/or activity, by methods known in the art, including evaluating expression of the early activation molecule and/or an early activation molecule activity of the cell, e.g., expression of TGF-θ, in the absence and presence of the compound. Possible compounds include, e.g., small molecules (e.g., small molecules described herein), peptides, fusion polypeptides (e.g., CD69R fusion polypeptides, AICL-R fusion polypeptides, and LLT1-R fusion polypeptides, e.g., as described herein), antibody molecules, and nucleic acid molecules. Examples of antibodies include, but are not limited to, antibody molecules or intrabodies which bind an early activation polypeptide and interfere with binding of the early activation polypeptide and an early activation binding polypeptide and antibody molecules which bind to an early activation polypeptide and decrease the level of the early activation polypeptide on the cell surface. Examples of anti-CD69 antibody molecules include, e.g., an anti-human CD69 antibody molecule, e.g., an anti-human CD69 antibody molecule analogous to an anti-mouse CD69 antibody 2.2, or an anti-human CD69 antibody molecule, e.g., an art known antibody, an antibody molecule which binds the epitope bound by such antibodies, an antibody molecule which competes for binding with such antibodies, an antibody molecule which interferes with binding to one or more of amino acid residues Glu 140, Asp171, Glu 180, Glu 185, Glu 187, Phe 175, Met 184, Leu 190, Glu 185 and Lys188 of human CD69, or other antibody described herein. Anti-AICL antibody molecules include, e.g., an anti-human AICL antibody, e.g., an art known anti-AICL antibody which can act as an antagonist (or an antibody molecule based thereon, e.g., a fragment, chimeric, humanized, or deimmunized antibody) or an antibody molecule which binds the epitope bound by such an antibody, an antibody molecule which competes for binding with such an antibody, or an antibody molecule which binds to or interferes with the binding of another antibody, receptor or ligand to one or more of amino acid residues of 37 to 149 of human AICL, or other antibody described herein. Anti-LLT1 antibody molecules include, e.g., an anti-human LLT1 antibody, e.g., an anti-LLT1 antibody, e.g., an art known antibody which can act as an antagonist (or an antibody molecule based thereon, e.g., a fragment, chimeric, humanized, or deimmunized antibody) or an antibody molecule which binds the epitope bound by such an antibody, an antibody molecule which competes for binding with such an antibody, or an antibody molecule which binds to or interferes with the binding of another antibody, receptor or ligand to one or more of amino acid residues of 76 to 132 of human LLT1, or an antibody molecule described herein. In some embodiments, the cell-based assay measures an activity of the early activation molecule, e.g., decreased expression of TGF-θ, decreased MAPK decreased $Ca^{2+}$ signalling and/or decreased dimer formation, e.g., CD69, AICL or LLT1 dimer formation. Compounds which decrease expression of TGF-θ and/or dimer formation can be selected as early activation molecule antagonists. In other embodiments, the cell based assay measures modulation, e.g., a decrease, of expression of an early activation molecule. For example, the early activation polypeptide expression or nucleic acid (e.g., mRNA or cDNA) expression, in the presence of the compound can be evaluated and compared to expression of the early activation molecule in the cell prior to administration of the compound. A decrease in the expression level is any statistically significant decrease in expression levels of the early activation molecule. In other embodiments, the cell based assay measures modulation, e.g., decreased levels, of the early activation polypeptide on the cell surface, e.g., as compared to the levels of the early activation polypeptide on the cell surface prior to administration of the compound.

In one embodiment, a compound which inhibits expression of an early activation molecule and/or inhibits an early activation molecule activity, e.g., expression of TGF-θ, of the cell is selected, e.g., selected for further screening, e.g., by administering the compound to a subject, e.g., an animal model, e.g., an animal model for unwanted cellular proliferation (e.g., an animal model for cancer), an animal model for immunodeficiency and/or an animal model of vaccine efficacy.

In another aspect, the invention features a method of identifying a compound which modulates immune response. The method includes: providing a compound which modulates expression of an early activation molecule and/or an early activation molecule activity, and administering the compound to a subject, e.g., an animal model.

In one embodiment, the compound is a compound which increases expression of an early activation molecule and/or an early activation molecule activity, e.g., increases expression of TGF-θ and/or increases dimer formation (e.g., CD69, AICL or LLT1 dimer formation), and the compound is administered to a subject, e.g., an animal model for an inflammatory disease (e.g., chronic or acute inflammatory disease), and/or an animal model for an immune disorder, e.g., an autoimmune disorder, and compounds which reduce one or more symptoms of the disorder are selected. An example of an animal model for an inflammatory disease includes a mouse model of collagen-induced arthritis.

In another embodiment, the compound is a compound which decreases expression of an early activation molecule and/or an early activation molecule activity, e.g., decreases expression of TGF-θ and/or decreases dimer formation (e.g., CD69, AICL or LLT1 dimer formation), and the compound is administered to a subject, e.g., an animal model for unwanted cellular proliferation (e.g., an animal model for cancer), an animal model for immunodeficiency and/or an animal model for vaccine efficacy, and compounds which reduce one or more symptoms of the disorder are selected.

The compound can be a compound identified by a method described herein or can be other compounds known to interact with an early activation molecule.

In another aspect, the invention features, a method of making a decision, e.g., a medical or financial decision. The method includes: generating or receiving data or information on the treatment of a subject for a disorder described herein; and using the data or information to make the decision, e.g., selecting between a first outcome and a second outcome.

In a preferred embodiment, the data is response to an administration of an early activation molecule agonist, antagonist or depletor (e.g., a CD69, AICL or LLT1 agonist, antagonist or depletor).

In a preferred embodiment, the decision is made by comparing the data to a reference standard and making the decision based on the relationship of the data to the reference. For example, the data can be a value or other term for subject response, and if the value or other term has a preselected relationship to the reference standard, e.g., if the value or term in the data is greater than a reference standard, selecting a first outcome and if the data is less than a reference standard selecting a second outcome. An outcome can be providing or not providing service or treatment, or paying for or not paying for all or part of a service or treatment.

In a preferred embodiment, the first outcome is suggesting or providing a first course of medical treatment, e.g., any treatment described herein, e.g., an additional administration of an early activation molecule agonist, antagonist, or depletor, and the second course is suggesting that the treatment not be given or not providing the treatment.

In a preferred embodiment the first outcome includes or results in the authorization or transfer of funds to pay for a service or treatment provided to a subject and the second outcome includes or results in the refusal to pay for a service or treatment provided to a subject. For example, an entity, e.g., a hospital, care giver, government entity, or an insurance company or other entity which pays for, or reimburses medical expenses, can use the outcome of a method described herein to determine whether a party, e.g., a party other than the subject patient, will pay for services or treatment provided to the patient. For example, a first entity, e.g., an insurance company, can use the outcome to determine whether to provide financial payment to, or on behalf of, a patient, e.g., whether to reimburse a third party, e.g., a vendor of goods or services, a hospital, physician, or other care-giver, for a service or treatment provided to a patient. For example, a first entity, e.g., an insurance company, can use the outcome of a method described herein to determine whether to continue, discontinue, enroll an individual in an insurance plan or program, e.g., a health insurance or life insurance plan or program.

In another aspect, the invention features a method of providing a database, e.g., a database useful for establishing a reference value referred to herein or for otherwise evaluating one or more subjects. The method includes: generating or receiving data, e.g., response to administration of an early activation molecule agonist, antagonist, or depletor (e.g., a CD69, an AICL, or a LLT1 agonist, antagonist or depletor) in the treatment of a disorder, e.g., a disorder described herein; and entering the data into the database.

In a preferred embodiment one or more of, an indicator (e.g., a value) for the disease state of a patient and a patient identifier are entered into the database.

In a preferred embodiment the database includes a plurality of entries, each one of which includes one or more of: data (data on response to administration of an early activation molecule agonist, antagonist, or depletor in the treatment of a disorder, e.g., a disorder described herein); an indicator for the disease state of a patient and a patient identifier.

In another aspect, the invention features a method of evaluating a patient which includes: comparing data from the patient (data on response to administration of an early activation molecule agonist, antagonist, or depletor in the treatment of a disorder, e.g., a disorder described herein, with data from a database described herein.

In another aspect, the invention features a method of constructing a reference standard which includes: including data from a database described herein in the standard. For example, one can take values from a database, perform a mathematical operation on them and use the result as a reference in arriving at a reference standard, e.g., taking an average of a plurality of values selected from the database and use the average as the standard.

In another aspect, the invention features a method of enhancing the production of an antibody to an antigen. The method includes administering an antigen to an animal; and administering an early activation molecule antagonist to the animal.

The animal can be, e.g., a mammal, e.g., a mouse, rat, goat, sheep, pig, cow or horse.

In one embodiment, the antigen is homologous to the animal, e.g., the antigen is from the same species as the species of animal to which it is administered, e.g., the antigen is a murine antigen administered to a mouse. In another embodiment, the antigen is heterologous, e.g., the antigen is from a species other than species of the animal to which it is administered, e.g., the antigen is a human antigen administered to a mouse.

In another embodiment, the method further includes isolating an immune cell from the animal, e.g., to produce a monoclonal antibody.

The invention is based, in part, on the discovery that modulation of any of the early activation molecules CD69, AICL and LLT1 play a role in immune reactivity. While not wishing to be bound by theory, this may be affected through the regulation of TGF-β1 synthesis. CD69, AICL and LLT1 are structurally similar receptors localized to the NK gene complex and expressed in most cells of hematopoietic origin (Boles et al., 1999). All three proteins have at least one C-type lectin domain with significant sequence similarity to each other. Upregulated levels of CD69, AICL and LLT1, unlike other lectin-like proteins associated with the NK gene complex, are seen at early time points of cellular activation. (Eichler et al., 2001).

Two different animal models of disease were analysed to determine the role of CD69 in the regulation of the immune response. First, the inhibitory role of CD69 and targeting of CD69 was evaluated in murine collagen-induced arthritis (CIA). CIA is a widely accepted experimental model of inflammatory joint disease, mainly rheumatoid arthritis (RA) (Feldmann et al., 1996). CIA provides a model for the study of autoimmunity and can be extended to other diseases where the immune response against self is exacerbated. It was found that CD69 plays an inhibitory role through the regulation of TGF-θ in the CIA. The second model, a tumor model, represents the opposite approach, where the goal is to enhance the immune response in order to suppress tumor growth and metastasis. Therefore, it constitutes an experimental system to test effective therapy that can be extended to infectious diseases and immunodeficiency syndromes in reestablishing an efficacious immune response. The use of CD69 in this strategy has been analysed in murine induced tumor and metastasis models that have lost expression of MHC class I genes. It was found that monoclonal antibodies (mAbs) specific for CD69 provide effective therapy in immune competent (wt) and immune compromised (SCID&RAG1$^{-/-}$) tumor-bearing mice. Like CD69, AICL and LLT1 are expressed at low levels in leukocytes, and are strongly and transiently upregulated. (Homann et al., 1997; Eichler et al., 2001). In addition, the AICL has been shown to be upregulated in certain cancers, namely B-CLL in unmutated immunoglobulin lines (Klein et al., 2001 J. Exp. Med. 11:1625; Rosenwald et al., 2001 J. Exp. Med. 11:1639). This can result in increased expression of TGF-θ, thereby producing an immunosuppressive microenvironment in subjects having this disorder. The elucidation of the role of CD69 as a negative modulator of immune reactivity provides for interesting and novel approaches for the therapy of cancer, chronic inflammation and other immune-mediated diseases (immunodeficiencies, autoimmune diseases, allograft transplants, and the like) by targeting CD69, AICL and/or LLT1. In addition, since CD69, AICL and LLT1 are selectively expressed by activated leukocytes infiltrating inflamed tissues and mediating tumor responses, the pharmacological stimulation of TGFβ1 synthesis through CD69, AICL and/or LLT1 can have a localized effect, thus avoiding the detrimental consequences of a systemic TGF-β1 up-regulation or delivery. Moreover, CD69, AICL and LLT1 are suitable markers for activated tissue leukocytes. Depletion of this activated subset using specific early activation molecule reagents can inhibit the active immune/inflammatory response. Therefore, the antagonism of an early activation molecule, e.g., by inhibiting TGF-θ release, may allow a locally enhanced immune response due to an increased recruitment and survival of highly activated immune effector cells (suitable for an enhanced response to vaccines, immunodeficiency therapy, etc).

The description of immunoregulatory molecules that enable a selective and local activation or inhibition of TGF-θ1 synthesis is therefore a novel approach to the treatment of immune-mediated diseases. In addition, early activation molecules can be used as a specific marker of the leukocyte population that is actively producing pro-inflammatory cytokines at inflammatory sites. The depletion of this deleterious population through targeting of CD69, AICL and/or LLT1, would allow the control of the downstream pro-inflammatory effectors. These new possible approaches through the inducible leukocyte receptors CD69, AICL and LLT1 are described herein.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entirety.

DESCRIPTION OF THE FIGURES

FIG. 23 depicts the amino acid sequence (SEQ ID NO:2) of human CD69 and the nucleic acid sequence (SEQ ID NO:1) encoding human CD69.

FIG. 24 depicts the amino acid sequence (SEQ ID NO:4) of human AICL and the nucleic acid sequence (SEQ ID NO:3) encoding human AICL.

FIG. 25 depicts the amino acid sequence (SEQ ID NO:6) of human LLT1 and the nucleic acid sequence (SEQ ID NO:5) encoding human LLT1.

DETAILED DESCRIPTION OF THE INVENTION

Figure 1A:
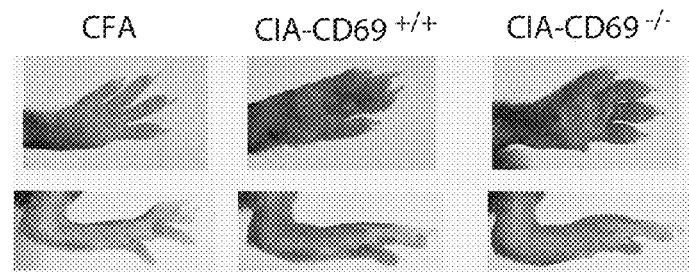
FIG. 1. Exacerbated CIA in $CD69^{-/-}$ mice. A, CFA treated control mice (left panels) are compared with representative pictures of the most severe cases of CIA in $CD69^{+/+}$ mice and $CD69^{-/-}$ mice (middle and right panels, respectively). B, incidence of arthritis (as percentage of diseased mice), and severity of clinical signs in $CD69^{+/+}$ (●), $CD69^{+/-}$ (▲), and $CD69^{-/-}$ (■) mice evaluated as described in Methods. Results correspond to arithmetic mean±s.d. from three separate experiments (18 mice/group/experiment). *, P<0.01 versus $CD69^{+/+}$ (Student's t test).

As provided above, an inhibitory role for CD69 in immune reactivity has been demonstrated using an experimental model of murine collagen-induced arthritis (CIA). CD69-deficient mice showed a higher incidence and severity of CIA with exacerbated B and T immune responses to type II collagen (CII). TGFθ1 and TGFθ2, which have a protective role in CIA, were reduced in $CD69^{-/-}$ mice inflammatory foci, correlating with an increase in proinflammatory cytokines interleukin (IL)-1 and RANTES. Local injection of a blocking anti-TGFβ antibody in CII-challenged wild type mice also increased CIA severity and proinflammatory cytokine mRNA levels in $CD69^{+/+}$ mice, but not $CD69^{-/-}$ mice. In addition, engagement of CD69 directly induces total and active TGF-β1 production in activated mouse T lymphocytes, mouse synovial cells, human synovial mononuclear cells from chronic arthropathies and Jurkat_stable transfectants of human CD69 but not the parental CD69 negative cell line. Thus, CD69 is a negative modulator of autoimmune reactivity and inflammation through the synthesis of TGFθ, a cytokine that in turn down regulates the production of different proinflammatory mediators.

Further, an inhibitory role of CD69 was demonstrated in vivo by analyzing the susceptibility of $CD69^{-/-}$ mice to tumors. $CD69^{-/-}$ mice challenged with tumors, showed strongly reduced tumor growth and prolonged survival compared with wildtype mice. This potent anti-tumor response correlates with a diminished production of TGF-β, an increase in inflammatory cytokines and the chemokine MCP-1, and was associated with increased recruitment of lymphoid effector cells and diminished apoptosis. The resistance of $CD69^{-/-}$ mice to tumor growth was NK and T lymphocyte-mediated and persisted in immuno-compromised CD69-1-RAG-negative mice. Moreover, TGF-β blockade in wildtype mice increased the anti-tumor response, directly implicating the diminished production of TGF-β found in $CD69^{-/-}$ mice as a basis of their enhanced anti-tumor immunity. In addition, engagement of CD69 induced extracellular signal-regulated kinase (ERK) activation and TGF-β production by T cells. Blockade of ERK by the specific pharmacological inhibitor PD98059 inhibited TGF-β production, directly linking CD69 signaling with TGF-β regulation.

Furthermore, in vivo treatment with the antagonist 2.2 anti-CD69 mAb was demonstrated to enhance the anti-tumor response in wildtype mice and in immune compromised SCID and RAG-deficient mice. Therefore, in vivo treatment with anti-CD69 monoclonal antibodies was demonstrated as a novel approach for enhancement of the immune response in manipulating tumor immunity that may be extended to infectious diseases and immune deficiency syndromes to restore immune responses.

In vivo treatment with anti-CD69 antibodies results in different effects depending on the anti-CD69 used; the antagonist 2.2 anti-CD69 antibody enhances immune response, resulting in increased CIA severity and tumor rejection. The depleting 2.3 anti-CD69 deletes CD69+ activated effector leukocytes, resulting in attenuated CIA. In addition, this depleting 2.3 anti-CD69 antibody may directly reject CD69+ tumors.

Significantly, a human monoclonal antibody (mAb), designated hAIM-29, has been produced, and specifically recognizes human CD69 on the surface of activated-human leukocytes (Molina et al., 2003). Experiments show that hAIM-29 activates intracellular calcium influx without Ig crosslinking and enhances phorbol myristate acetate (PMA)-induced cell proliferation, in a manner similar to other mouse anti-CD69 antibodies.

Like CD69, AICL and LLT1 are expressed at low levels in leukocytes and are strongly and transiently upregulated (Hamann et al., 1997; Eichler et al., 2001). Therefore, AICL and LLT1, like CD69, may regulate leukocyte TGFθ release.

The role of early activation polypeptides as negative modulators of immune reactivity provides for the treatment of chronic inflammation and other immune-mediated diseases by targeting these polypeptides. In addition, since CD69, AICL and LLT1 are selectively expressed in activated leukocytes infiltrating inflamed tissues, the pharmacological stimulation of TGF-$\beta$1 synthesis through CD69, AICL and/or LLT1 may have a localized effect, thus avoiding the detrimental consequences of a systemic TGF-$\beta$1 up-regulation or delivery.

The current invention provides procedures for the modulation of the immune response by the targeting of CD69, AICL and/or LLT1 through different procedures.

One specific aim/goal of this invention is the regulation of the immune response based on the targeting of an early activation molecule with substances that promote early activation molecule signaling or interaction with its putative ligand(s) or receptor(s), which are identified as early activation molecule agonists. The second aim is the modulation of immune response through an early activation molecule using substances that inhibit or block early activation molecule signaling, including those that inhibit early activation molecule expression, block early activation molecule binding to its receptors or ligands or induce early activation polypeptide down-modulation from a cell surface, identified as early activation molecule antagonists. The third aim is the immune regulation through the depletion of cells expressing an early activation molecule using substances that deplete CD69+, AICL+ and/or LLT1+ cells, identified as early activation molecule depletors.

Other specific aims of this invention include methods for discovering, identifying, or otherwise evaluating an agent for use as an agonist, antagonist or depletor of CD69+, AICL+ and/or LLT1+ cells. These methods can use as all or part of the process of the evaluation of: $Ca^{2+}$ signaling, activation of MAPK, production of TGF-$\beta$, induction of apoptosis mediators, and cell lysis. In addition, examples of some of these substances are specifically identified herein, such as the use of antibodies anti-early activation polypeptide antibody molecules or substances directly or indirectly derived from these antibodies. Moreover, putative ligands or receptors of an early activation polypeptide identified by the use of affinity chromatography with early activation molecule-related constructs or products, or whose agonist, antagonist or depleting activity on the early activation molecule is identified by any of the methods indicated are aims of this invention.

Another specific aim of this invention is the use of substances that can modulate the immune response directly or indirectly through an early activation molecule in the treatment of immune-mediated diseases. Autoimmune or tumoral processes are influenced by the absence or presence of early activation molecules and the treatment with substances that act through the early activation molecules. Thus, methods of the invention can be used to treat a number of other immune-mediated diseases, such as:

Autoimmune diseases, including rheumatoid arthritis and other types of chronic or acute arthritis or arthropathies with an immune component, systemic lupus erythematosus, scleroderma, Sjögren syndrome, autoimmune diabetes, thyroiditis, and other organ-specific immune diseases, including psoriasis. Also included are neurologic diseases, including multiple sclerosis, myasthenia gravis, and other neurologic immune-mediated diseases. Also included are gastrointestinal diseases, including Crohn's disease, colitis, celiac disease, hepatitis, and other immune-mediated diseases.

Cardiovascular diseases, including atherosclerosis, cardiomyopathy, rheumatic fever, endocarditis, vasculitis, and other immune-mediated cardiovascular diseases.

Respiratory diseases, including emphysema, respiratory airways infections, and other immune-mediated respiratory diseases.

Allergic processes and hypersensitivity-reactions (type I, II, III, and IV), including asthma, rhinitis, and other immune-mediated hypersensitivity reactions.

Transplant or graft rejection, including organ transplants, tissue graft, or blood transfusion. Also included is graft versus host disease, e.g., as occurs during bone marrow transplant.

Oncologic diseases, including leukemia, lymphoproliferative diseases, solid tumors and all other types of unwanted cell proliferation including non-malignant and malignant disorders, e.g., all other forms of cancer.

Infectious diseases, including bacteria, virus, fungal or parasitic infections, septic shock syndromes and other immunopathological responses to infectious agents.

Inherited immuno-deficiency diseases and acquired immuno-deficiency syndromes, and immuno-suppression syndromes by radiotherapy and chemotherapy treatments.

Degenerative processes as neurodegenerative processes that implicate immune competent cells as microglia.

Control administration of antigen used to manipulate the nature of antigen-specific response.

Gene therapy

In addition, some immune-mediated processes can be helped by an intervention through an early activation molecule, such as immunosuppression that can be applied to a variety of immune-mediated processes, including those previously indicated, or immuno-enhancers that can be applied to vaccination, as well as protective immunity injecting DNA encoding microbial antigens or tumor antigens, or other processes for the treatment of immune-mediated diseases, including those previously indicated.

Since the TGF-$\beta$ cytokine and other mediators of CD69, AICL and LLT1 signaling have a pleiotropic effect, all the diseases above suggested may be covered for the described effect of these early activation molecules in immune regulation, and the specific aims are not limited to the following predictions, that are based in the examples indicated below. The agonist strategy through an early activation molecule would predict a higher production of TGF-$\beta$, with its consequent effects on immune modulation that have been extensively described (Letterio and Roberts, 1997; Prud'homme and Piccirillo, 2000). The immunosuppressor effect of TGF-$\beta$ could be useful for the treatment of immune diseases where the activation of the immune system is exacerbated, such as autoimmune diseases, transplant rejection, and others from the previous list. The antagonist approach would act through the opposite pathway, being used for treatment of diseases or processes that need to enhance the immune system, such as tumor rejection, infection treatment or its prevention as vaccination. The depleting strategy would eliminate CD69+, AICL+ and/or LLT1+ cells, which are the cells locally activated in response to antigenic stimulus and mediate the immune response. Therefore, the expected consequence would be the amelioration of diseases associated with exacerbation of immune response, such as autoimmune diseases, transplant rejection, and others from the previous list.

Early Activation Polypeptides

The terms "early activation proteins" and "early activation polypeptides" refer to CD69, AICL, LLT1 and fragments thereof. The term "protein" and "polypeptide" are used interchangeably herein.

CD69

As used herein, "CD69", also known as "very early activation" protein, "activation inducer molecule", and "gp 34/28", refers to mammalian CD69, preferably human CD69 protein. Accordingly, the term "human CD69" refers to a polypeptide which has or is homologous to (e.g., at least about 85%, 90%, 95% identical to) an amino acid sequence (SEQ ID NO:2) as shown in Lopez-Cabrera (1993) *J. Exp. Med.* 178 (2), 537-547; or which is encoded by: (a) a nucleic acid sequence encoding a human CD69 (e.g., a nucleic acid sequence (SEQ ID NO: 1) encoding human CD69 as provided in Lopez-Cabrera (1993) *J. Exp. Med.* 178 (2): 537-547) (see FIG. 23); (b) a nucleic acid sequence degenerate to a naturally occurring human CD69 sequence; (c) a nucleic acid sequence homologous to (e.g., at least about 85%, 90%, 95% identical to) the naturally occurring human CD69 nucleic acid sequence; or (d) a nucleic acid sequence that hybridizes to one of the foregoing nucleic acid sequences under stringent conditions, e.g., highly stringent conditions. A preferred CD69 is a naturally occurring variant or allele of CD69.

AICL

As used herein, "AICL", also known as "activation-induced C-type lectin" refers to mammalian AICL, preferably human AICL protein. Accordingly, the term "human AICL" refers to a polypeptide which has or is homologous to (e.g., at least about 85%, 90%, 95% identical to) an amino acid sequence (SEQ ID NO:4) as shown in Hamann et al. (1997) *Immunogenetics* 45:295-300; or which is encoded by: (a) a nucleic acid sequence encoding a human AICL (e.g., a nucleic acid sequence (SEQ ID NO:3) encoding human AICL as provided in Hamann et al. (1997) *Immunology* 45:295-300 (see FIG. 24); (b) a nucleic acid sequence degenerate to a naturally occurring human AICL sequence; (c) a nucleic acid sequence homologous to (e.g., at least about 85%, 90%, 95% identical to) the naturally occurring human AICL nucleic acid sequence; or (d) a nucleic acid sequence that hybridizes to one of the foregoing nucleic acid sequences under stringent conditions, e.g., highly stringent conditions. A preferred AICL is a naturally occurring variant or allele of AICL.

LLT1

As used herein, "LLT1", also known as "lectin-like transcript" refers to mammalian LLT1, preferably human LLT1 protein. Accordingly, the term "human LLT1" refers to a polypeptide which has or is homologous to (e.g., at least about 85%, 90%, 95% identical to) an amino acid sequence (SEQ ID NO:6) as shown in Boles et al. (1999) *Immunogenetics* 50:1-7; or which is encoded by: (a) a nucleic acid sequence encoding a human LLT1 (e.g., a nucleic acid sequence (SEQ ID NO:5) encoding human LLT1 as provided in Boles et al. (1999) *Immunogenetics* 50:1-7 (see FIG. 25); (b) a nucleic acid sequence degenerate to a naturally occurring human LLT1 sequence; (c) a nucleic acid sequence homologous to (e.g., at least about 85%, 90%, 95% identical to) the naturally occurring human LLT1 nucleic acid sequence; or (d) a nucleic acid sequence that hybridizes to one of the foregoing nucleic acid sequences under stringent conditions, e.g., highly stringent conditions. A preferred LLT1 is a naturally occurring variant or allele of LLT1.

Anti-Early Activation Polypeptide Antibody Molecules

An "anti-early activation polypeptide antibody molecule" is an antibody molecule that interacts with (e.g., binds to) an early activation polypeptide, preferably a human early activation protein. Preferably, anti-early activation polypeptide antibody molecules bind to the extracellular domain of the early activation polypeptide (i.e., an epitope of the early activation polypeptide located outside of a cell).

In some aspects, the anti-early activation polypeptide antibody molecule can be an anti-CD69 antibody molecule, e.g., an anti-human CD69 antibody molecule. Examples of monoclonal antibodies to human CD69 include, but are not limited to, an anti-human CD69 antibody molecule analogous to an anti-mouse antibody 2.2, an anti-human CD69 antibody molecule analogous to an anti-mouse CD69 antibody 2.3, or an anti-human CD69 antibody, e.g., an art known antibody, which can act as an agonist, an antagonist or a depletor of CD69, or antibody molecules having epitopes which overlap the epitope of such an antibody, or which compete with such an antibody for binding. Examples of art known anti-human CD69 antibodies include: TP1/8, TP1/22, TP 1/28, TP 1/33, TP 1/55 (as described, e.g., in Cebrian et al. (1988) J. Exp. Med. 168:1621-37); CH/4, CH/1, CH/2, FAB/1 (as described, e.g., in Sánchez-Mateos et al. (1991) Eur. J. Immunol. 21:2317-25); L78, MLR3, FN61, FN50 (as described in, e.g., Schwarting, R. et al. (Eds) Leukocyte Typing IV, Springer-Verlag, New York, 1989, p. 428); MLR3 (as described, e.g., in Corte, G et al. (1981) Eur. J. Immunol. 11:162-164; EA 1 (as described, e.g., in Hara, T (1986) J. Exp. Med. 164:1988-2005); Leu 23 (as described, e.g., in Lanier, L L et al. (1988) J. Exp. Med. 167:1572-1585); and C1.18, E16.5 (as described, e.g., in Gerosa, F (1991) Mol. Immunol. 28:159-168. Non-limiting examples of antibody molecules which can be used in the invention include: hAIM-29; an antibody molecule which interacts with, e.g., binds to, an epitope which includes one or more residues of the neck of a CD69 polypeptide (e.g., one or more residues from residues 62 to 84 of human CD69); an antibody molecule which interacts with, e.g., binds to, an epitope which includes one or more residues of the NK domain (or carbohydrate recognition domain (CRD)) of a CD69 polypeptide (e.g., one or more residues from residues 82 to 199 of human CD69); an antibody molecule which interacts with, e.g., binds to, an epitope which includes one or more residues from the intracellular domain of a CD69 polypeptide (e.g., one or more residues from 1 to 40 of human CD69); an antibody molecule which interacts with, e.g., binds to an epitope, which when bound modulates, e.g., enhances or reduces, the interaction of CD69 cytoplasmic and/or transmembrane regions with a downstream effector, which activity can be determined by the methods described herein (e.g., production of TGF-θ, MAPK activation, or $Ca^{2+}$ signaling); an antibody molecule which interacts with, e.g., binds, an epitope (e.g., a conformational or linear epitope), which epitope when bound modulates, e.g., enhances or reduces, CD69 dimer formation (e.g., an epitope which includes residue Cys68 of human CD69 or a residue proximally located near Cys68); an antibody molecule which can modulate cell surface expression of CD69, e.g., an antibody molecule which can down-modulate CD69 from a cell surface; an antibody molecule which can modulate binding of a CD69 ligand or receptor, e.g., an antibody which can inhibit, e.g., competitively inhibit, or enhance binding of a ligand or a receptor to CD69; an antibody molecule which interacts with, e.g., binds, or which can inhibit or enhance binding of a ligand or receptor to, one or more of amino acid residues Glu 140, Asp171, Glu 180, Glu 185, Glu 187, Phe 175, Met 184, Leu 190, Glu 185 and Lys188 of human CD69).

In other embodiments, the anti-early activation polypeptide antibody molecule can be an anti-AICL antibody molecule, e.g., an anti-human AICL antibody molecule. Examples of monoclonal antibodies to human AICL include, but are not limited to, an art known anti-human AICL antibody which can act as an agonist, an antagonist or a depletor of AICL, or antibody molecules having epitopes which overlap the epitope of such an antibody, or which compete with such an antibody for binding. Examples of antibody molecules which can be used in the invention include: an antibody molecule which interacts with, e.g., binds to, an epitope which includes one or more residues of the neck of an AICL polypeptide (e.g., one or more residues from residues 26 to 36 of human AICL); an antibody molecule which interacts with, e.g., binds to, an epitope which includes one or more residues of the NK domain (or carbohydrate recognition domain (CRD)) of an AICL polypeptide (e.g., one or more residues from residues 37 to 149 of human AICL); an antibody molecule which interacts with, e.g., binds to, an epitope which includes one or more residues from the intracellular domain of an AICL polypeptide (e.g., one or more residues from 1 to 7 of human AICL); an antibody molecule which interacts with, e.g., binds to an epitope, which when bound modulates, e.g., enhances or reduces, the interaction of AICL cytoplasmic and/or transmembrane regions with a downstream effector, which activity can be determined by the methods described herein (e.g., production of TGF-θ, MAPK activation, or $Ca^{2+}$ signaling); an antibody molecule which interacts with, e.g., binds, an epitope (e.g., a conformational or linear epitope); an antibody molecule which can modulate cell surface expression of AICL, e.g., an antibody molecule which can down modulate AICL from a cell surface; an antibody molecule which can modulate binding of an AICL ligand or receptor, e.g., an antibody which can inhibit, e.g., competitively inhibit, or enhance binding of a ligand or a receptor to AICL.

In yet other embodiments, the anti-early activation polypeptide antibody molecule can be an anti-LLT1 antibody molecule, e.g., an anti-human LLT1 antibody molecule. Examples of monoclonal antibodies to human LLT1 include, but are not limited to, an art known anti-human LLT1 antibody which can act as an agonist, an antagonist or a depletor of LLT1, or antibody molecules having epitopes which overlap the epitope of such an antibody, or which compete with such an antibody for binding. Examples of antibody molecules which can be used in the invention include: an antibody molecule which interacts with, e.g., binds to, an epitope which includes one or more residues of the neck of n LLT1 polypeptide (e.g., one or more residues from residues 60 to 75 of human LLT1); an antibody molecule which interacts with, e.g., binds to, an epitope which includes one or more residues of the NK domain (or carbohydrate recognition domain (CRD)) of a LLT1 polypeptide (e.g., one or more residues from residues 76 to 132 of human LLT1); an antibody molecule which interacts with, e.g., binds to, an epitope which includes one or more residues from the intracellular domain of a LLT1 polypeptide (e.g., one or more residues from 1 to 30 of human LLT1); an antibody molecule which interacts with, e.g., binds to an epitope, which when bound modulates, e.g., enhances or reduces, the interaction of LLT1 cytoplasmic and/or transmembrane regions with a downstream effector, which activity can be determined by the methods described herein (e.g., production of TGF-θ, MAPK activation, or $Ca^{2+}$ signaling); an antibody molecule which interacts with, e.g., binds, an epitope (e.g., a conformational or linear epitope), which epitope when bound modulates, e.g., enhances or reduces, LLT1 dimer formation (e.g., an epitope which includes residue Cys63 of human LLT1 or a residue proximally located near Cys63); an antibody molecule which interacts with, e.g., binds, an epitope (e.g., a conformational or linear epitope); an antibody molecule which can modulate cell surface expression of LLT1, e.g., an antibody molecule which can down modulate LLT1 from a cell surface; an antibody molecule which can modulate binding of a LLT1 ligand or a LLT1 receptor, e.g., an antibody which can inhibit, e.g., competitively inhibit, or enhance binding of a ligand or a receptor to LLT1.

In one embodiment, the anti-early activation polypeptide antibody molecule binds all or part of the epitope of an antibody described herein, e.g., an art known anti-human CD69 antibody, an art known anti-human AICL antibody, or an art known anti-LLT1 antibody which can act as an agonist, an antagonist or a depletor, or an anti-human early activation polypeptide antibody analogous to an anti-mouse early activation polypeptide antibody, e.g., an anti-mouse CD69 antibody (e.g., antibody 2.2, 2.3, or H1.2F3 (described, e.g., in Yokoyama et al. (1988) J. Immunol. 141:369-376). An anti-CD69 antibody can bind one or more residues of the epitopes described in Sanchez-Mateos (1991) or compete for binding with an antibody which binds one of the described epitopes. The anti-early activation polypeptide antibody molecule can inhibit, e.g., competitively inhibit, the binding of an antibody described herein, e.g., an art-known anti-human early activation polypeptide antibody described herein, to a human early activation polypeptide. An anti-early activation polypeptide antibody molecule may bind to an epitope, e.g., a conformational or a linear epitope, which epitope when bound prevents binding of an antibody described herein, e.g., an art known anti-human early activation polypeptide antibody described herein. The epitope can be in close proximity spatially or functionally-associated, e.g., an overlapping or adjacent epitope in linear sequence or conformationally to the one recognized by an antibody described herein, e.g., an art known anti-human early activation polypeptide antibody described herein.

In a preferred embodiment, the interaction, e.g., binding, between an anti-early activation polypeptide antibody molecule and an early activation polypeptide occurs with high affinity (e.g., affinity constant of at least about $10^9$ $M^{-1}$ or better) and specificity. Preferably, the anti-early activation polypeptide antibody molecule modulates immune response, e.g., is an early activation molecule agonist, an early activation molecule antagonist or an early activation molecule depleting antibody.

As used herein, "specific binding" refers to the property of the binding agent, preferably the antibody, to: (1) to bind to an early activation polypeptide, e.g., human early activation polypeptide, with an affinity of at least $1\times10^7$ $M^{-1}$, and (2) preferentially bind to the early activation polypeptide, e.g., human early activation polypeptide, with an affinity that is at least two-fold, 50-fold, 100-fold, 1000-fold, or more greater than its affinity for binding to a non-specific antigen (e.g., BSA, casein) other than the early activation polypeptide.

As can be seen from the disclosure herein, many types of anti-early activation polypeptide antibody molecules, e.g., antibodies, or antigen-binding fragments thereof, are useful in the methods of this invention. The antibody molecules can be of the various isotypes, including: IgG (e.g., IgG1, IgG2 (e.g., IgG2a, IgG2b), IgG3, IgG4), IgM, i.e., IgM/λ, IgA1, IgA2, IgD, or IgE. A preferred antibody molecule is an IgG isotype. The antibody molecules can be full-length (e.g., an IgG1 or IgG4 antibody) or can include only an antigen-binding fragment (e.g., a Fab, F(ab')$_2$, Fv or a single chain Fv fragment). The antibody is preferably an engineered antibody molecule, e.g., a fully human or a humanized antibody.

Antibodies, or other agents described herein, can be evaluated for the ability to agonize, antagonize or deplete CD69, AICL or LLT1.

A depletor anti-early activation polypeptide antibody is one which, upon administration to an animal, either alone or conjugated to a toxin, reduces the absolute number of early activation polypeptide+ cells, e.g. CD69+, AICL+ and/or LLT1+ tumor cells; e.g., CD69+, AICL+ and/or LLT1+ leukocytes at chronic inflammatory infiltrates. It will usually act through direct lysis of these cells (as opposed to, e.g., transient sequestration of cells in an organ compartment such as bone marrow or liver).

An antagonist anti-early activation polypeptide antibody is one which, upon administration to an animal, induces CD69+, AICL+ and/or LLT1+ cells to decrease their production of TGF-beta cytokine, e.g., by blocking endogenous signaling induced by engagement of CD69, AICL and/or LLT1 by one or more of its natural ligands or receptors (e.g. by blocking CD69, AICL or LLT1 interaction with its natural ligands or receptors) referred to herein as "a blocking antagonist". Other early activation polypeptide antagonists include, e.g., "a down-modulating antagonist" which decreases the level of an early activation polypeptide on the cell surface, e.g., by binding to an early activation polypeptide and internalizing the polypeptide.

An agonist anti-early activation polypeptide antibody is one which, upon administration to an animal, induces CD69+, AICL+ and/or LLT1+ cells to increase their production of TGF-beta cytokine, e.g., by enhancing signaling in the absence of binding to a natural ligand or receptor, or over and above the endogenous signaling induced by engagement of CD69, AICL or LLT1 by one or more of its natural ligands or receptors.

Various in vitro methods can be used, e.g., in conjunction with whole animal assays, to evaluated candidates for activity as a depletor, antagonist, or agonist. An in vitro assay may not be indicative of in vivo activity in every case but never the less can be useful in screening strategies.

Early Activation Molecule Depletors

An in vitro early activation polypeptide depletor antibody is one which, upon incubation with cells expressing the early activation polypeptide, reduces the absolute number of those cells. This can be effected through their direct lysis, e.g. via complement-dependent, Fc-Receptor-dependent, or toxin-dependent mechanisms. Thus, an early activation polypeptide depletor can kill cells expressing the early activation polypeptide in in vitro killing assays. Isotype can play an important role in whether an anti-early activation polypeptide antibody will function as a depletor by way of a complement-based mechanism. If an antibody is able to bind complement, it will probably behave as a depletor. Most naturally occurring antibodies have a relatively high affinity for complement and will thus be depletors. This is less likely in the case of murine IgG1 and human IgG4, which have low affinity for complement. In addition, antibodies can be engineered to reduce or increase affinity for complement. A mouse, or other, anti-mouse early activation polypeptide depletor antibody can kill mouse cells expressing the early activation polypeptide in vitro in the presence of complement. Target early activation polypeptide expressing cells useful for testing such antibodies include, e.g., murine leukemias, e.g., EL4 thymoma cell line for CD69. For example, a mouse, or other, anti-human CD69 depletor antibody, (e.g., hAIM-29 mAb), can kill human CD69-expressing cells, e.g., CD69 expressing human T lymphocytes from rheumatoid arthritis synovial fluid, CD69 expressing human leukemias, or stable transfectants of CD69, e.g., Jurkat leukemia cells which stably express CD69. This antibody will not kill (or will kill at a much lower level) control cells which do not express CD69, e.g., parental Jurkat leukemia cells that do not express CD69. Thus, the ability of an antibody to function as a depletor can be assayed, in vitro, for its ability to lyse target cells expressing an early activation polypeptide and control cells that do not express the early activation polypeptide. A candidate depletor will lyse the cells expressing the early activation polypeptide but not control cells that do not express the early activation polypeptide (or will lyse them to a much lesser extent). In one example, cell lysis can be monitored in an assay in which target (and control) cells are loaded with $CR^{51}$ and incubated with the antibody in the presence of fresh baby rabbit complement, typically for 2 h at 37° C. Afterwards, supernatant is recovered and the level of cell lysis evaluated by the amount of $CR^{51}$ released into the supernatant. Lysis is indicated by release of $CR^{51}$ by lysed cells.

Early Activation Molecule Agonists

An in vitro agonist anti-early activation polypeptide antibody is one which, upon incubation with CD69+, AICL+ and/or LLT1+ cells, increases their production of TGF-beta cytokine, e.g., by enhancing signaling in the absence of binding to a natural ligand or receptor, or by enhancing signaling over and above the endogenous signaling induced by engagement of CD69, AICL or LLT1 by one or more of its natural ligands or receptors, present in the in vitro culture system. Thus, one can perform an in vitro screen for agonists by incubating a candidate agonist with a cell expressing the early activation polypeptide and evaluating its effect on TGF-θ production, e.g., as compared with a control cell, e.g., a cell that does not express the early activation polypeptide. For example, an anti-mouse CD69 antibody can be evaluated for the ability to behave as an in vitro agonist by evaluating its ability to promote TGF-θ production by ConA-activated CD69 expressing splenocytes. An anti-human CD69 antibody, such as hAIM-29 mAb, can be evaluated for the ability to mediate TGF-θ synthesis by Jurkat cells stably transfected with CD69. An agonist will promote TGF-θ production in cells expressing the early activation polypeptide but not in a control line, preferably the parental line that does not express the early activation polypeptide. Agonism may require addition of a second crosslinking antibody which cross links the candidate agonists. An agonist should not act as a depletor.

Early Activation Molecule Antagonist

An in vitro antagonist anti-early activation polypeptide antibody is one which, upon incubation with CD69+, AICL+ and/or LLT1+ cells, decreases their production of TGF-θ cytokine, e.g., by blocking endogenous signaling induced by engagement of CD69, AICL or LLT1 by one or more of its natural ligands or receptors, present in the in vitro culture system. Thus, one can perform an in vitro screen for antagonists by incubating a candidate antagonist with a cell expressing the early activation polypeptide and evaluating its effect on TGF-θ production, e.g., as compared with a control cell, e.g., a cell that does not express the early activation polypeptide. For example, an anti-mouse CD69 antibody can be evaluated for the ability to behave as an in vitro antagonist by evaluating its ability to inhibit or reduce TGF-θ production by ConA-activated CD69 expressing splenocytes. An anti-human CD69 antibody, such as hAIM-29 mAb, can be evaluated for the ability to mediate TGF-θ synthesis by Jurkat cells stably transfected with CD69. An antagonist will inhibit TGF-θ production in cells expressing the early activation polypeptide but not in a control line, preferably the parental line that does not express the early activation polypeptide. An in vitro antagonist can also be a down modulating antagonist, e.g., an in vitro down modulating antagonist anti-early activation polypeptide antibody. An in vitro antagonist can be screened for by incubating a candidate antagonist with a cell expressing the early activation polypeptide and evaluating whether the early activation polypeptide disappears from the cell surface. For example, a murine anti-early activation polypeptide antibody can be evaluated for its ability to down modulate an early activation polypeptide by using a reagent capable of detecting the presence of the murine anti-early activation polypeptide antibody, e.g., an anti-mouse polyclonal reagent. If the reagent does not detect the candidate, then the antagonist can be identified as a down modulating antagonist. An antagonist should not act as a depletor.

In addition an antagonist can have one or more of the following properties:
1) it blocks binding of pure early activation polypeptide to its purified receptor or ligand, to partially purified preparations such as membrane fractions from cells, which normally respond to the early activation polypeptide, e.g., which express an early activation polypeptide receptor, or to whole cells which normally respond to the early activation polypeptide, e.g., which express an early activation polypeptide receptor;
2) it blocks the binding of a cell expressing the early activation polypeptide to purified early activation polypeptide receptor;
3) it blocks binding of a cell expressing the early activation polypeptide to a cell expressing early activation polypeptide receptor (e.g., cells which normally respond to the early activation polypeptide) or to partially purified preparations such as membrane fractions from cells, which normally respond to the early activation polypeptide, e.g., which express an early activation polypeptide receptor. E.g., the candidate antagonist blocks binding of preparations containing a putative CD69R to a human CD69 stable transfectant of Jurkat cells (but not with the parental CD69-cell line);
4) it blocks binding of agonist monoclonal antibodies to a cell expressing the early activation polypeptide, thus preventing TGF-θ production by the agonist antibody;
5) it decreases the level of an early activation polypeptide on the cell surface, e.g., by binding to an early activation polypeptide and internalizing the polypeptide.

Antibody Molecules

As used herein, the term antibody molecule, refers to a molecule which includes a sufficient number of complementarity determining regions (CDRs), preferably 6, presented in a framework which allows binding to the cognate antigen of the CDRs. Thus, the term includes, full length antibodies (including naturally occurring antibodies and engineered antibodies), and antigen binding fragments of naturally occurring or engineered antibodies. The term includes various types of antibodies or antibody molecules including monospecific, monoclonal, recombinant, human, non-human, e.g., murine. Also included are single chain antibodies, intrabodies, and bi-valent antibodies. Also included are chimeric, CDR-grafted, humanized, deimmunized, as well as other antibody molecules which have been engineered to reduce immunogenicity, e.g., those having CDRs derived from a non-human source, e.g., derived from an nonhuman animal such as a mouse, and or derived from random or partially random generation of sequences, e.g., a by use of a phage display method. Such non-human can be inserted into human, humanized, or other frameworks which are less antigenic when administered to a human.

Thus, an antibody molecule can have: CDRs from a non-human source, e.g., from a non-human antibody, e.g., from a mouse immunoglobulin or another non-human immunoglobulin, from a consensus sequence, or from a sequence generated by phage display, or any other method of generating diversity; and having a framework that is less antigenic in a human than a non-human framework, e.g., in the case of CDRs from a non-human immunoglobulin, less antigenic than the non-human framework from which the non-human CDRs were taken. The framework of the immunoglobulin can, e.g., be human, humanized non-human, e.g., a mouse, framework modified to decrease antigenicity in humans, or a synthetic framework, e.g., a consensus sequence, or from an in vitro method of generating diversity.

Preferred antibody molecules can include at least one, and preferably two, heavy (H) chain variable regions (abbreviated herein as VH) or antigen binding fragments thereof, and at least one and preferably two light (L) chain variable regions (abbreviated herein as VL) or antigen binding fragments thereof. The VH and VL regions are subdivided into regions of hypervariability, termed "complementarity determining regions" ("CDR"), interspersed with regions that are more conserved, termed "framework regions" (FR). The extent of the framework region and CDRs has been precisely defined (see, e.g., Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, which are incorporated herein by reference). Preferably, each VH and VL of an antibody molecule is composed of three CDRs and four FRs, arranged from amino-terminus to carboxy-terminus in the following order: FR1, CDR1, FR2, CDR2, FR3, CDR3, FR4. The CDRs and FRs can be from different sources.

The VH or VL chain of an antibody molecule can include all or part of a heavy or light chain constant region. In one embodiment, the antibody molecule is a tetramer of two heavy immunoglobulin chains and two light immunoglobulin chains, wherein the heavy and light immunoglobulin chains are inter-connected by, e.g., disulfide bonds. The full length heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody molecule to host tissues or factors, including various cells of the immune system (e.g., effector cells) and the first component (C1q) of the classical complement system. Antibody molecules can include IgA, IgG, IgE, IgD, IgM (as well as subtypes thereof), wherein the light chains may be of types kappa or lambda.

As discussed above, "antigen-binding fragments" of an antibody molecule are within the term antibody molecule. An antigen-binding fragment, as used herein, can refer to a portion of an antibody which specifically binds to the early activation polypeptide (e.g., human early activation polypeptide). Examples of binding fragments include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) one or more isolated complementarity determining regions (CDRs) having sufficient framework to specifically bind, e.g., an antigen binding portion of a variable region.

Antibody fragments may also be produced by chemical methods, e.g., by cleaving an intact antibody with a protease, such as pepsin or papain, and optionally treating the cleaved product with a reducing agent. Alternatively, useful fragments may be produced by using host cells transformed with truncated heavy and/or light chain genes.

An antigen binding portion of a light chain variable region and an antigen binding portion of a heavy chain variable region, e.g., the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

The term "monospecific antibody or antibody molecule" refers to an antibody or antibody molecule that displays a single binding specificity and affinity for a particular target, e.g., epitope. This term includes a "monoclonal antibody" or "monoclonal antibody composition,".

The term "recombinant" antibody or antibody molecule, as used herein, refers to antibodies or antibody molecules that are prepared, expressed, created or isolated by recombinant means, such as antibody molecules expressed using a recombinant expression vector transfected into a host cell, antibody molecules isolated from a recombinant, combinatorial antibody library, antibody molecules isolated from an animal (e.g., a mouse) that is transgenic for human immunoglobulin genes or antibody molecules prepared, expressed, created or isolated by any other means that involves splicing of human immunoglobulin gene sequences to other DNA sequences. Such recombinant antibody molecules include humanized, CDR grafted, chimeric, deimmunized, in vitro generated (e.g., by phage display) antibodies, and may optionally include constant regions derived from human germline immunoglobulin sequences.

Monoclonal, chimeric and humanized antibodies, which have been modified by, e.g., deleting, adding, or substituting other portions of the antibody, e.g., the constant region, are also within the scope of the invention. For example, an antibody can be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, placental transport, among others.

A preferred monoclonal antibody, for example, can involve use of the five-feature BABκ,λ mouse strain, carrying a human Ig transloci in its germ line (Magadán et al., 2002; Nicholson et al., 1999), in which a human mAb, hAIM-29, directed against the early human activation marker CD69, can be generated.

In one embodiment, the constant region of the antibody can be replaced by another constant region from, e.g., a different species. This replacement can be carried out using molecular biology techniques. For example, the nucleic acid encoding the VL or VH region of an antibody can be converted to a full-length light or heavy chain gene, respectively, by operatively linking the VH or VL-encoding nucleic acid to another nucleic acid encoding the light or heavy chain constant regions. The sequences of human light and heavy chain constant region genes are known in the art. Preferably, the constant region is human, but constant regions from other species, e.g., rodent (e.g., mouse or rat), primate, camel, rabbit, can also be used. Constant regions from these species are known in the art (see e.g., Kabat, E. A., et al. (1991) *Sequences of Proteins of Immunological Interest, Fifth Edition*, U.S. Department of Health and Human Services, NIH Publication No. 91-3242).

Methods for altering an antibody constant region are known in the art. Antibodies with altered function, e.g. altered affinity for an effector ligand, such as FcR on a cell, or the C1q component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar types of alterations could be described, which if applied to immunoglobulins of murine or other species, would reduce or eliminate these functions.

Production of Anti-Early Activation Polypeptide Antibodies

Useful immunogens for making anti-early activation polypeptide antibody molecules include cells which express the early activation polypeptide, membrane preparations from cells expressing the early activation polypeptide, early activation polypeptide containing vesicles or micelles, early activation polypeptides or fragments of the early activation polypeptide, e.g., isolated or purified early activation polypeptide, e.g., a human early activation polypeptide, e.g., a biochemically isolated early activation polypeptide, or a portion thereof, or a recombinantly produced early activation polypeptide or fragments there, e.g., the extracellular or intracellular domain of an early activation polypeptide, or a fusion protein containing an early activation polypeptide or any of the fragments or constructs described herein. The antigen is preferably a human antigen. A soluble early activation polypeptide can be obtained by, e.g., recombinant production of soluble the polypeptide (e.g., an early activation polypeptide lacking all or a part of the transmembrane and/or intracellular domains of the early activation polypeptide), or by lysis of a cell expressing the early activation polypeptide. Techniques for generating antibodies to CD69 are described in Sanchez-Mateos et al. (1991) *Eur. J. Immunol.* 21:2317-2325, the contents of which is expressly incorporated by reference. These techniques as well as other techniques known in the art can be used to generate antibodies to any of CD69, AICL and LLT1.

Fragments of CD69 which include residues about 62-84 or portions thereof of SEQ ID NO:2, fragments of AICL which include about residues 26 to 36 or portions thereof of SEQ ID NO:4, or fragments of LLT1 which includes about residues 60 to 75 or portions thereof of SEQ ID NO:6, can be used to make antibodies against neck regions of each or the early activation polypeptides, respectively, e.g., the fragments can be used as immunogens or used to characterize the specificity of an antibody. Similarly, fragments of CD69 which include residues 82 to 199, or portions thereof of SEQ ID NO:2, fragments of AICL which include residues 37 to 149, or portions thereof of SEQ ID NO:4, or fragments of LLT1 which include residues 76 to 132, or portions thereof of SEQ ID NO:6, can be used to make an antibody against the NK domain of an early activation protein; fragments of CD69 which include residues 62 to 199 or portions thereof of SEQ ID NO:2, fragments of AICL which include residues 26 to 149 or portions thereof of SEQ ID NO:4, or fragments of LLT1 which include residues 60 to 132 or portions thereof of SEQ ID NO:6, can be used to make an antibody against an extracellular region of the early activation polypeptide protein; fragments of CD69 which include residues about 1 to 40 or portions thereof of SEQ ID NO:2, fragments of AICL which include residues about 1 to 7 of SEQ ID NO:4, or fragments of LLT1 which include residues about 1 to 30 or portions thereof of SEQ ID NO:6, can be used to make an antibody against an intracellular region of the early activation protein.

Antibody molecules reactive with, or specific for, any region or domain of CD69, AICL or LLT1, particularly an extracellular region or domain of CD69, AICL or LLT1, can be made and tested for suitability for use in the invention.

Antibodies which bind only a native early activation protein, only denatured or otherwise non-native early activation protein, or which bind both, are within the invention. Antibodies with linear or conformational epitopes are within the invention. Conformational epitopes can sometimes be identified by identifying antibodies which bind to native but not denatured early activation protein.

As described in more detail below, antibody molecules (preferably, monoclonal antibodies from differing organisms, e.g., rodent, sheep, human) against the early activation polypeptide can be produced using art-recognized methods. Once the antibody molecules are obtained, they can be tested for suitability for use in the invention, e.g., to determine if the antibody molecule is an agonist, antagonist, or depleting antibody.

Monoclonal antibodies can be produced by a variety of techniques, including conventional monoclonal antibody methodology e.g., the standard somatic cell hybridization technique of Kohler and Milstein, Nature 256: 495 (1975). See generally, Harlow, E. and Lane, D. (1988) Antibodies: A Laboratory Manual, Cold Spring Harbor Laboratory Press, Cold Spring Harbor, N.Y. Although somatic cell hybridization procedures are preferred, in principle, other techniques for producing monoclonal antibody can be employed e.g., viral or oncogenic transformation of B lymphocytes. The preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

An antibody can be obtained from a non-human source and the variable regions, and in particular the CDRs, can be sequenced, and used to make antibody molecules, e.g., humanized antibodies, useful in the invention. The location of the CDRs and framework residues can be determined (see, e.g., Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference).

An antibody or an immunoglobulin chain can be humanized by methods known in the art. Once the murine antibodies are obtained, the variable regions can be sequenced. The location of the CDRs and framework residues can be determined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). The light and heavy chain variable regions can, optionally, be ligated to corresponding constant regions.

Murine anti-early activation polypeptide antibodies can be sequenced using art-recognized techniques.

Humanized or CDR-grafted antibody molecules or immunoglobulins can be produced by CDR-grafting or CDR substitution, wherein one, two, or all CDRs of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference.

Winter describes a CDR-grafting method that may be used to prepare the humanized antibodies of the present invention (UK Patent Application GB 2188638A, filed on Mar. 26, 1987; Winter U.S. Pat. No. 5,225,539), the contents of which are expressly incorporated by reference. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, Science 229:1202-1207, by Oi et al., 1986, BioTechniques 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

Humanized antibodies in which specific amino acids have been substituted, deleted or added, are thus within the invention. In particular, preferred humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the contents of which are hereby incorporated by reference. The acceptor framework can be a mature human antibody framework sequence or a consensus sequence. As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

Other techniques for humanizing immunoglobulin chains, including antibodies, are described in Padlan et al. EP 519596 A1, published on Dec. 23, 1992.

The anti-early activation polypeptide antibody molecule may also be modified in other ways to decrease immunogenicity, e.g., by specific deletion of human T cell epitopes or "deimmunization" by the methods disclosed in WO 98/52976 and WO 00/34317, the contents of which are specifically incorporated by reference herein.

In some embodiments, the anti-early activation polypeptide antibody molecule includes a light or a heavy chain variable region having at least one, two and, preferably, three CDRs substantially identical to a CDR from a non-human anti-early activation polypeptide light or heavy chain variable region, respectively. In one preferred embodiment, the modified antibody or antigen-binding fragment thereof includes all six CDRs from the same non-human anti-early activation polypeptide antibody, e.g., an art known anti-human CD69, AICL or LLT1 antibody molecule, e.g., the panel of anti-CD69 antibody molecules described in Sanchez-Mateos (1991) Eur. J. Immunol. 21:2317-2325.

The light or heavy chain immunoglobulin of the modified anti-early activation polypeptide antibody or antigen-binding fragment thereof can further include a light chain or a heavy chain variable framework sequence from a light chain or heavy chain variable framework present in a human or a non-human, e.g., rodent, antibody.

Human monoclonal antibodies (mAbs) directed against human proteins can be generated using transgenic mice carrying the human immunoglobulin genes rather than the mouse system. Such transgenic mice can include mice that carry a portion of the human immunoglobulin heavy and light chain genes. For example, the five-feature BABκ,λ transgenic mouse strain carries transgenes of human μ heavy and κ and λ light chains in an inactivated endogenous IgH and IgK background (Magadán et al., 2002; Nicholson et al., 1999). The immunization of these transloci mice allows the generation of an immune response that induces the production and secretion of human IgM (HuIgM) Abs against a wide variety of human and non-human antigens (Ags) (Magadán et al., 2002). Molina et al. (2003) have successfully used these mice to generate a HuIgM mAb, hAIM-29, which specifically binds to the human CD69 antigen.

Similarly, in the HuMAb Mouse®, available from Medarex and GenMab, mouse genes for creating antibodies are inactivated and replaced with many of the key gene sequences from unarranged human antibody genes coding for heavy and light chains. Another mouse available is the XenoMouse® from Abgenix which has approximately 80% of the human heavy chain antibody genes and a significant amount of the human light chain genes. Other transgenic mice are available for generating human antibodies which contain complete sets of the variable and constant genes found in the corresponding natural human immunoglobulin loci. These mice, also referred to as Kirin TC Mice™ are available from Medarex. The Kirin TC Mice™ are "transchromosomic," meaning that the mouse genes for creating antibodies have been inactivated and have been replaced by the human chromosomes containing all of the human antibody genes, including all heavy chain classes that encode all isotypes (IgG1-4, IgA1-2, IgD, IgM and IgE). Also available from Medarex, is the KM-mouse®, a crossbred mouse that combines the characteristics of the HuMAb-Mouse with Kirin's TC Mouse. The KM-mouse, like the Kirin TC mouse, retains the capability to produce all human antibody isotypes. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326). The procedures for the isolation of human mAbs are identical to those used for conventional mouse immunization and hybridoma production (reviewed in Brüggemann and Taussig, 1997; Brüggemann and Neuberger, 1996; Jakobovits, 1995).

Chimeric antibodies, including chimeric immunoglobulin chains, can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

Also within the term are in vitro generated species where all or part of the variable region, e.g., one or more or all CDRs, is generated in a non-immune cell selection, e.g., an in vitro phage display, protein chip or any other method in which candidate sequences can be tested for their ability to bind to an antigen. E.g., combinatorial antibody display methods, have been developed to identify and isolate antibody fragments having a particular antigen specificity, and can be utilized to produce an antibody molecule.

Once displayed on the surface of a display package (e.g., filamentous phage), the antibody library is screened with the antigen, or peptide fragment thereof, to identify and isolate packages that express an antibody having specificity for the antigen. Nucleic acid encoding the selected antibody can be recovered from the display package (e.g., from the phage genome) and subcloned into other expression vectors by standard recombinant DNA techniques.

Specific antibodies with high affinities for a surface protein can be made according to methods known to those in the art, e.g., methods involving screening of libraries (Ladner, R. C., et al., U.S. Pat. No. 5,233,409; Ladner, R. C., et al., U.S. Pat. No. 5,403,484). Further, the methods of these libraries can be used in screens to obtain binding determinants that are mimetics of the structural determinants of antibodies.

An antigen-binding region can also be obtained by screening various types of combinatorial libraries with a desired binding activity, and to identify the active species, by methods that have been described.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allows the creation of large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages.

Anti-early activation polypeptide antibody molecules useful in the present invention can be recombinant antibodies produced by host cells transformed, e.g., with DNA encoding immunoglobulin light and heavy chains of a desired antibody. Recombinant antibody molecules may be produced by known genetic engineering techniques. For example, recombinant antibodies may be produced by cloning a nucleotide sequence, e.g., a cDNA or genomic DNA sequence, encoding the immunoglobulin light and heavy chains of the desired antibody from a hybridoma cell that produces an antibody useful in this invention. The nucleotide sequence encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding may be renaturable according to well known methods (Kim and Baldwin, "Specific Intermediates in the Folding Reactions of Small Proteins and the Mechanism of Protein Folding", *Ann. Rev. Biochem.* 51, pp. 459-89 (1982)). It is possible that the host cells will produce portions of intact antibodies, such as light chain dimers or heavy chain dimers, which also are antibody homologs according to the present invention.

It will be understood that variations on the above procedure are useful in the present invention. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for binding the early activation polypeptide, e.g., the constant region may be modified by, for example, deleting specific amino acids. The molecules expressed from such truncated DNA molecules are useful in the methods of this invention. In addition, bifunctional antibodies may be produced in which one heavy and one light chain are anti-early activation polypeptide antibody and the other heavy and light chain are specific for an antigen other than that early activation polypeptide, or another epitope of that early activation polypeptide.

Antibody Molecule Conjugates

Antibody molecules of the invention can be conjugated, covalently or non-covalently, to other moieties, e.g., labels or therapeutic agents, e.g., toxins (e.g., protein (e.g., diphtheria or ricin) or chemical toxins), therapeutic isotopes, or other therapeutic moieties.

Accordingly, an anti-early activation polypeptide antibody molecule can be derivatized or linked to another functional molecule (e.g., another peptide or protein). The antibodies and antibody portions of the invention are intended to include derivatized and otherwise modified forms of the antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized (or labeled) to include fluorescent compounds, various enzymes, prosthetic groups, luminescent materials, bioluminescent materials, fluorescent emitting metal atoms, e.g., europium (Eu), and other lanthamides, and radioactive materials (described below). Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

An anti-early activation polypeptide antibody or antigen-binding fragment thereof may be conjugated to another molecular entity, typically a label or a therapeutic (e.g., a cytotoxic or cytostatic) agent or moiety.

A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

An anti-early activation polypeptide antibody or antigen-binding fragment thereof may be conjugated to another molecular entity, e.g., a moiety which modulates immunogenicity and/or half life. In one embodiment, the molecular entity is polyethylene glycol (PEG) or derivatives thereof. PEGylation is a chemical conjugation method which can reduce potential immunogenicity and/or extends half life. Various methods of PEGylating an antibody are known. See, e.g., Bhandra et al. (2002) Pharmazie 57(1):5-29.

Other Early Activation Polypeptide Binding Agents

An "early activation polypeptide binding agent" is an agent which interacts with (e.g., binds to) an early activation polypeptide, preferably a human early activation polypeptide. Preferably, the interaction, e.g., binding, occurs with high affinity, e.g., affinity constant of at least $10^7$ $M^{-1}$, preferably, between $10^8$ $M^{-1}$ and $10^{10}$ $M^{-1}$, or about $10^9$ $M^{-1}$, and specificity. Early activation polypeptide binding agents can be CD69, AICL or LLT1 agonists, antagonists or depletors. Examples of early activation polypeptide binding agents include anti-early activation polypeptide antibodies (e.g., antibodies as described above) as well as small molecules or peptidomimetics.

Useful in the methods of this invention are early activation polypeptide mimetic agents. These agents, which include peptides, semi-peptidic compounds or non-peptidic compounds (e.g., small organic molecules), are inhibitors of an early activation molecule activity.

In preferred embodiments, the agent is a member of a combinatorial library, e.g., a peptide or organic combinatorial library, or a natural product library. In a preferred embodiment, a plurality of test compounds, e.g., library members, includes at least 10, $10^2$, $10^3$, $10^4$, $10^5$, $10^6$, $10^7$, or $10^8$ compounds. In a preferred embodiment, the plurality of test compounds, e.g., library members, share a structural or functional characteristic.

In one embodiment, the invention provides libraries of early activation polypeptide binding agents. The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. *Acc. Chem. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds of the invention can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allow to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen-binding site. It will be appreciated that a wide variety of peptidic, peptidomimetic, or non-peptidic compounds can be readily generated in this way.

The "split-pool" strategy results in a library of peptides, e.g., inhibitors, which can be used to prepare a library of test compounds of the invention. In another illustrative synthesis, a "diversomer library" is created by the method of Hobbs DeWitt et al. (*Proc. Natl. Acad. Sci. U.S.A.* 90:6909 (1993)). Other synthesis methods, including the "tea-bag" technique of Houghten (see, e.g., Houghten et al., *Nature* 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., *J Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are described below.

In one embodiment, compounds of the invention can be screened for the ability to interact with an early activation polypeptide by assaying the activity of each compound to bind directly to the polypeptide, e.g., by incubating the test compound with an early activation polypeptide and a lysate, in one well of a multiwell plate, such as a standard 96-well microtiter plate. In this embodiment, the activity of each individual compound can be determined. A well or wells having no test compound can be used as a control. After incubation, the activity of each test compound can be determined by assaying each well. Thus, the activities of a plurality of test compounds can be determined in parallel.

In still another embodiment, large numbers of test compounds can be simultaneously tested for binding activity. For example, test compounds can be synthesized on solid resin beads in a "one bead-one compound" synthesis; the compounds can be immobilized on the resin support through a photolabile linker. A plurality of beads (e.g., as many as 100,000 beads or more) can then be combined with yeast cells and sprayed into a plurality of "nano-droplets", in which each droplet includes a single bead (and, therefore, a single test compound). Exposure of the nano-droplets to UV light then results in cleavage of the compounds from the beads. It will be appreciated that this assay format allows the screening of large libraries of test compounds in a rapid format.

Combinatorial libraries of compounds can be synthesized with "tags" to encode the identity of each member of the library (see, e.g., W. C. Still et al., U.S. Pat. No. 5,565,324 and PCT Publication Nos. WO 94/08051 and WO 95/28640). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels. Such a tagging scheme can be useful, e.g., in the "nano-droplet" screening assay described above, to identify compounds released from the beads.

In preferred embodiments, the libraries of compounds of the invention contain at least 30 compounds, more preferably at least 100 compounds, and still more preferably at least 500 compounds. In preferred embodiments, the libraries of compounds of the invention contain fewer than $10^9$ compounds, more preferably fewer than $10^8$ compounds, and still more preferably fewer than $10^7$ compounds.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to early activation proteins or early activation nucleic acids, have a stimulatory or inhibitory effect on, for example, early activation molecule expression or an early activation molecule activity. Compounds thus identified can be used to modulate the activity of target gene products (e.g., early activation molecule genes) in a therapeutic protocol, to elaborate the biological function of the target gene product, or to identify compounds that disrupt normal target gene interactions.

In one embodiment, the invention provides assays for screening candidate or test compounds that are substrates of an early activation protein or polypeptide or a biologically active portion thereof. In another embodiment, the invention provides assays for screening candidate or test compounds that bind to or modulate an activity of an early activation protein or polypeptide or a biologically active portion thereof, e.g., compounds that modulate signaling of an early activation protein or polypeptide.

Assaying an early activation protein activity in the presence of inhibitors can be used to determine the nature of the signaling activity. The assay can include additional controls and steps to insure that the observed activity results from an early activation polypeptide. For example, control samples, e.g., samples produced from cells transformed with a control vector instead of a vector overexpressing an early activation nucleic acid, can be tested in parallel. The activity can also be tracked in chromatography fractions, e.g., to determine if the activity and the early activation polypeptide co-purify. Additional assays and conditions are described, e.g., in Yamaoka et al. (1998) *J Biol Chem* 273:11895-11901, and Thien-Khai et al. (1997) *J Biol Chem* 272:31315-31320.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses an early activation protein or biologically active portion thereof is contacted with a test compound, and the ability of the test compound to modulate an early activation molecule activity is determined. Determining the ability of the test compound to modulate early activation molecule activity can be accomplished by monitoring, for example, sensing environmental stimuli, e.g., an early activation polypeptide ligand, a small molecules; sensing biological messengers, e.g., TGF-θ. The cell, for example, can be of mammalian origin, e.g., human.

The ability of the test compound to modulate early activation polypeptide binding to a compound, e.g., an early activation molecule substrate, or to bind to the early activation polypeptide can also be evaluated. This can be accomplished, for example, by coupling the compound, e.g., the substrate, with a radioisotope or enzymatic label such that binding of the compound, e.g., the substrate, to the early activation polypeptide can be determined by detecting the labeled compound, e.g., substrate, in a complex. Alternatively, the early activation polypeptide could be coupled with a radioisotope or enzymatic label to monitor the ability of a test compound to modulate binding of the early activation polypeptide to a substrate of the early activation polypeptide in a complex. For example, compounds (e.g., substrates of the early activation polypeptide) can be labeled with $^{125}$I, $^{35}$S, $^{14}$C, or $^3$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a substrate of an early activation polypeptide) to interact with the early activation polypeptide with or without the labeling of any of the interactants can be evaluated. For example, a microphysiometer can be used to detect the interaction of a compound with the early activation polypeptide without the labeling of either the compound or the early activation polypeptide. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and the early activation polypeptide.

In yet another embodiment, a cell-free assay is provided in which an early activation protein or biologically active portion thereof is contacted with a test compound and the ability of the test compound to bind to the early activation protein or biologically active portion thereof is evaluated. Preferred biologically active portions of the early activation proteins to be used in assays of the present invention include fragments which participate in interactions with non-early activation molecules, e.g., fragments with high surface probability scores.

Soluble and/or membrane-bound forms of isolated proteins (e.g., CD69, AICL or LLT1 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the CD69 protein to bind to a target molecule can be accomplished using real-time Biomolecular Interaction Analysis (BIA) (see, e.g., Sjolander, S. and Urbaniczky, C. (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BLAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either the early activation polypeptide, an anti-early activation polypeptide antibody or its target molecule to facilitate separation of complexed from uncomplexed forms of one or both of the proteins, as well as to accommodate automation of the assay. Binding of a test compound to an early activation protein, or interaction of an early activation protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/early activation polypeptide fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the early activation protein and either the non-adsorbed target protein or the early activation protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of early activation polypeptide binding or activity determined using standard techniques.

Other techniques for immobilizing either an early activation protein or a target molecule on matrices include using conjugation of biotin and streptavidin. Biotinylated early activation protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with the early activation protein or target molecules but which do not interfere with binding of the early activation protein to its target molecule. Such antibodies can be derivatized to the wells of the plate, and unbound target or the early activation protein trapped in the wells by antibody conjugation. Methods for detecting such complexes, in addition to those described above for the GST-immobilized complexes, include immunodetection of complexes using antibodies reactive with the early activation protein or target molecule, as well as enzyme-linked assays which rely on detecting an enzymatic activity associated with the early activation protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11: 141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the early activation protein or biologically active portion thereof with a known compound which binds the early activation protein to form an assay mixture, contacting the assay mixture with a test compound, and determining the ability of the test compound to interact with an early activation protein, wherein determining the ability of the test compound to interact with an early activation protein includes determining the ability of the test compound to preferentially bind to the early activation protein or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the early activation genes herein identified. In an alternative embodiment, the invention provides methods for determining the ability of the test compound to modulate the activity of an early activation protein through modulation of the activity of a downstream effector of an early activation target molecule. For example, the activity of the effector molecule on an appropriate target can be determined, or the binding of the effector to an appropriate target can be determined. In preferred embodiments, the activity of TGF-θ can be determined.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the early activation proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268: 12046-12054; Bartel et al. (1993) Biotechniques 14:920-924; Iwabuchi et al. (1993) Oncogene 8:1693-1696; and Brent WO94/10300), to identify other proteins, which bind to or interact with the early activation protein ("early activation protein-binding proteins" or "early activation protein-bp") and are involved in early activation molecule activity, e.g., expression of TGF-θ. Such early activation protein-bps can be activators or inhibitors of signals by the early activation proteins or early activation polypeptide targets as, for example, downstream elements of an early activation polypeptide-mediated signaling pathway.

The two-hybrid system is based on the modular nature of most transcription factors, which consist of separable DNA-binding and activation domains. Briefly, the assay utilizes two different DNA constructs. In one construct, the gene that codes for an early activation protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: early activation protein can be the fused to the activator domain.) If the "bait" and the "prey" proteins are able to interact, in vivo, forming an early activation polypeptide-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the early activation protein.

In another embodiment, modulators of early activation molecule expression are identified. For example, a cell or cell free mixture is contacted with a candidate compound and the expression of the early activation mRNA or protein evaluated relative to the level of expression of the early activation mRNA or protein in the absence of the candidate compound. When expression of the early activation mRNA or protein is greater in the presence of the candidate compound than in its absence, the candidate compound is identified as a stimulator of the early activation mRNA or protein expression (i.e., an early activation molecule agonist). Alternatively, when expression of the early activation mRNA or protein is less (statistically significantly less) in the presence of the candidate compound than in its absence, the candidate compound is identified as an inhibitor of the early activation mRNA or protein expression (i.e., an early activation molecule antagonist). The level of the early activation mRNA or protein expression can be determined by methods known for detecting mRNA or protein expression.

In another aspect, the invention pertains to a combination of two or more of the assays described herein. For example, a modulating agent can be identified using a cell-based or a cell free assay, and the ability of the agent to modulate the activity of an early activation protein can be confirmed in vivo, e.g., in an animal such as an animal model for cancer.

This invention further pertains to novel agents identified by the above-described screening assays. Accordingly, it is within the scope of this invention to further use an agent identified as described herein (e.g., an early activation molecule modulating agent, an antisense nucleic acid molecule, an early activation protein-specific antibody, or another early activation molecule-binding partner) in an appropriate animal model to determine the efficacy, toxicity, side effects, or mechanism of action, of treatment with such an agent. Furthermore, novel agents identified by the above-described screening assays can be used for treatments as described herein.

Substantially Identical or Homologous

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), J. Mol. Biol. 48:444-453, algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a homology limitation of the invention) are a Blossum 62 scoring matrix with a gap penalty of 12, a gap extend penalty of 4, and a frameshift gap penalty of 5.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the binding agent polypeptides of the invention may have additional conservative or non-essential amino acid substitutions, which do not have a substantial effect on the polypeptide functions. Whether or not a particular substitution will be tolerated, i.e., will not adversely affect desired biological properties, such as binding activity can be determined as described in Bowie, J U et al. (1990) *Science* 247:1306-1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

Pharmaceutical Compositions

In another aspect, the present invention provides compositions, e.g., pharmaceutically acceptable compositions, which include an early activation molecule binding agent, e.g., an anti-early activation polypeptide antibody, as described herein, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. The carrier is suitable for intravenous, intramuscular, subcutaneous, parenteral, spinal or epidermal administration (e.g., by injection or infusion). Depending on the route of administration, the active compound, i.e., the early activation molecule binding agent may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The composition may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection (e.g., by needleless injection). In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The early activation molecule binding agents can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In some embodiments, pharmaceutical compositions of early activation molecule binding agents, alone or in combination with other agent, can be delivered or administered topically or by transdermal patches. In those embodiments where the binding agent is a small molecule, oral administration can be used. Additionally, the compositions can be delivered parenterally, especially for treatment of arthritis, such as psoriatic arthritis, and for direct injection of skin lesions. Parenteral therapy is typically intra-dermal, intra-articular, intramuscular or intravenous. Early activation molecule binding agents can be applied, in a cream or oil based carrier, directly. Alternatively, an aerosol can be used topically. These compounds can also be orally administered.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163, 5,383,851, 5,312,335, 5,064,413, 4,941,880, 4,790,824, or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicaments through the skin; U.S. Pat. No. 4,447, 233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other implants, delivery systems, and modules are known to those skilled in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. In one embodiment, the anti-early activation polypeptide antibody is administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of a binding agent. A "therapeutically effective amount" refers to an amount effective, at dosages and for periods of time necessary, to achieve the desired therapeutic result. A therapeutically effective amount of the early activation molecule binding agent may vary according to factors such as the disease state, age, sex, and weight of the individual, and the ability of the antibody or antibody portion to elicit a desired response in the individual. A therapeutically effective amount is also one in which any toxic or detrimental effects of the early activation molecule binding agent is outweighed by the therapeutically beneficial effects. A "therapeutically effective dosage" preferably inhibits a measurable parameter, relative to untreated subjects. The ability of a compound to inhibit a measurable parameter can be evaluated in an animal model system predictive of efficacy in human. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Uses

The early activation molecule agonists, antagonists and depletors described herein or identified by a method described herein can be used to treat a subject having a disorder characterized by enhanced or decreased immune response. For example, early activation molecule antagonists can be used to treat a subject having a disorder characterized by a decreased immune response or a subject that does not have a decreased or compromised immune system but would nevertheless benefit from an increased or augmented immune response. Such disorders include disorders characterized by unwanted cell proliferation such as cancer, or an immunodeficiency. The methods include administering to a subject, e.g., a subject having a disorder characterized by decreased immune response, a therapeutically effective amount of an early activation molecule antagonist. In other embodiments, the methods can be used to prevent such disorders by administering a prophylactically effective amount of an early activation molecule antagonist.

Thus, in some aspects, the early activation molecule antagonists can be used to treat or prevent unwanted cellular proliferation such as cancer in a subject by inhibiting the growth or proliferation of the hyperproliferative cell and/or by inducing killing of the hyperproliferative cell. The early activation molecule antagonist can decrease the expression and/or activity of the early activation molecule, thereby enhancing tumor immunity in a subject. For example in subjects having cancer, e.g., lymphocytic leukemia, e.g., B cell chronic leukemia lacking immunoglobulin mutations, AICL is upregulated. (Klein et al. (2001) J. Exp. Med. 11:1625; Rosenwald et al. (2001) J. Exp. Med. 11:1639). An AICL antagonist, e.g., a blocking or down-modulating AICL antagonist, can be used to decrease expression or activation of AICL, thereby enhancing tumor immunity in such subjects. While not wishing to be bound by theory, it is believed that by antagonizing an early activation polypeptide, TGF-θ synthesis is inhibited. Since TGF-θ can act as an immunosuppressant, by inhibiting TGF-θ, immune cells can continue to inhibit the growth or proliferation of hyperproliferative cells. In addition, an early activation molecule depletor can be used to treat or prevent early activation molecule expressing-cancers. For example, an AICL depletor can be used to inhibit growth or proliferation of hyperproliferative AICL expressing cells in subjects having lymphocytic leukemia, e.g., B cell chronic leukemia lacking immunoglobulin mutation. As used herein, "inhibiting the growth or proliferation" of the hyperproliferative cell, e.g., neoplastic cell, refers to slowing, interrupting, arresting or stopping its growth and metastases, and does not necessarily indicate a total elimination of the neoplastic growth. As used herein, "inducing the killing" of the hyperproliferative cell, e.g., neoplastic cell, refers to the partial or complete elimination of such cells, and does not necessarily indicate a total elimination of the neoplastic growth.

The terms "induce", "inhibit", "potentiate", "elevate", "increase", "decrease" or the like, e.g., which denote quantitative differences between two states, refer to at least statistically significant differences between the two states. For example, "an amount effective to inhibit growth of hyperproliferative cells" means that the rate of growth of the cells will at least statistically significantly different from the untreated cells. Such terms are applied herein to, for example, rates of cell proliferation.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Thus, in one aspect, an antagonist to an early activation molecule can be used to treat or prevent a disorder characterized by non-pathologic hyperproliferation, e.g., a fibrotic disorder. The fibrotic disorder can be associated with one or more of: trauma, surgery, infection, environmental pollutants, tobacco, alcohol or other toxins. The disorder can be associated with, e.g., one or more of: overabundant wound repair (e.g., hypertrophic scars and keloids), renal fibrosis (proliferation of mesangial cells), liver fibrosis (proliferation of liver stellate cells). Examples of fibrotic disorders include: keloids, burns, hypertrophic scars or other skin disorders (e.g., local or systemic scleroderma, e.g., scleroderma systemic sclerosis), liver cirrhosis, kidney fibrosis (e.g., related to diabetes and/or hypertension), surgical adhesions (e.g., from gastrointestinal surgery or neurosurgery adhesions), vascular grafts, indiopathic pulmonary fibrosis, radiation-induced fibrosis, asbestos-related fibrosis (e.g., black or brown lung), fibrosis associated with viral hepatitis, macular degeneration, retinal and vitreal retinopathy, and fibrosis associated with acute respiratory syndrome. The fibrosis can be acute or chronic fibrosis. Examples of acute fibrosis include: accidental injury, infections, surgery, burns, radiation-induced fibrosis and chemotherapy induced fibrosis. Chronic fibrosis can be associated, e.g., with viral infection, diabetes, and hypertension.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

Further examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma. Many such neoplastic conditions can progress to a metastatic state, e.g., resulting in tumor cells moving to new locations and forming metastatic tumors.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol/Hemotol.* 11:267-97); lymphoid malignancies include, but are not limited to acute lymphoblastic leukemia (ALL) which includes B-lineage ALL and T-lineage ALL, chronic lymphocytic leukemia (CLL) (e.g., T- or B-cell chronic lymphocytic leukemia, e.g., B-cell chronic lymphocytic leukemia with or without immunoglobulin mutation), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The early activation molecule antagonist can be administered in combination with one or more therapeutic agents, e.g., a therapeutic agent or agent for treating or preventing unwanted cell proliferation. The therapeutic agents include, for example, one or more of a chemotherapeutic agent, a radioisotope, and a cytotoxin. Examples of chemotherapeutic agents include taxol, cytochalasin B, gramicidin D, mitomycin, etoposide, tenoposide, vincristine, vinblastine, colchicin, busulfan, cisplatin, doxorubicin, daunorubicin, dihydroxy anthracin dione, mitoxantrone, mithramycin, chlorambucil, gemcitabine, actinomycin, procaine, tetracaine, lidocaine, propranolol, puromycin, maytansinoids and analogs or homologs thereof. Additional therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioisotopes can include alpha, beta and/or gamma emitters. Examples of radioisotopes include $^{212}$Bi, $^{213}$Bi, $^{131}$I, $^{211}$At, $^{186}$Re, $^{90}$Y and $^{117}$Lu. The early activation molecule antagonist and the therapeutic agents can be administered simultaneously or sequentially. In addition, the early activation molecule antagonists can be administered in conjunction with other cancer treatment modalities such as a surgery to remove all of part of the cancerous tissue or the organ containing the cancerous tissue.

As used herein, the terms "cytotoxic agent", "anticancer agent" and "antitumor agent" are used interchangeably herein and refer to agents that have the property of inhibiting the growth or proliferation (e.g., a cytostatic agent), or inducing the killing, of hyperproliferative cells. Preferably, the cytotoxic agent inhibits the development or progression of a neoplasm, particularly a solid tumor, a soft tissue tumor, a metastatic lesion, a lymphoma, or a leukemia.

As used herein, a "therapeutically effective amount" of an agent, alone or in combination with, a cytotoxic agent refers to an amount of such agents which in combination is effective, upon single- or multiple-dose administration to the subject, e.g., a patient, at inhibiting the growth or proliferation, or inducing the killing, of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

As used herein, "a prophylactically effective amount" of an agent, alone or in combination with, a cytotoxic agent refers to an amount of such agents which in combination is effective, upon single or multiple dose administration to the subject, e.g., a patient, in preventing or delaying the occurrence of the onset or recurrence of a disorder, e.g., a neoplastic disorder.

When administered to a patient undergoing cancer treatment, the early activation molecule antagonist may be administered in cocktails containing the other anti-cancer agents. They may also be administered in cocktails containing agents that treat the side effects of radiation therapy, such as antiemetics, radiation protectants, etc.

Early activation molecule agonists and depletors of cells expressing an early activation polypeptide can be used to treat a subject having a disorder characterized by an increased, e.g., exacerbated, immune response. Such disorders include acute or chronic inflammatory disorders, and immune disorders, e.g., autoimmune disorders. The methods include administering to a subject, e.g., a subject having a disorder characterized by increased immune response, a therapeutically effective amount of an early activation molecule agonist and/or a depletor of cells expressing an early activation polypeptide. In other embodiments, the methods can be used to prevent such disorders by administering a prophylactically effective amount of an early activation molecule agonist.

Inflammatory diseases such as acute lung injury, acute respiratory distress syndrome, arthritis (e.g., CIA), asthma, bronchitis, cystic fibrosis, hepatitis, inflammatory bowel disease, multiple sclerosis, reperfusion injury (e.g., myocardial), nephritis, pancreatitis, psoriasis, artery occlusion (e.g., retinal), stroke, systemic lupus erythematosus, transplantation, ultraviolet light induced injury, and/or vasculitis may be treated using the invention. The inflammatory disease may be acute or chronic, and is preferably mediated by leukocytes (reviewed in Weissmann et al., Ann. N.Y. Acad. Sci. 389:11-24, 1982; Janoff, A., Annu. Rev. Med. 36:207-216, 1985; Hart et al., J. Rheumatol. 16:1184-1191, 1989; Doring, Am. J. Respir. Crit. Care Med. 150:S114-S117, 1994; Demling, Annu. Rev. Med. 46:193-202, 1995). Diseases with symptoms of chronic inflammation include, but are not limited to, inflammatory bowel diseases, such as Crohn's disease and ulcerative colitis, psoriasis, sarcoidosis and rheumatoid arthritis.

The early activation molecule agonist can be administered alone or in combination with one or more therapeutic agents, e.g., a therapeutic agent or agent for treating inflammation.

The early activation molecule antagonists described herein or identified by a method described herein can also be used to enhance an immune response to an antigen, e.g., a vaccine, or a nucleic acid encoding the antigen, e.g., vaccine. The methods include administering to a subject an antigen, e.g., a vaccine, and/or DNA encoding an antigen and an early activation molecule antagonist, to thereby enhance immune response to the antigen by the subject.

Examples of vaccines can include, cancer vaccines, HIV vaccines, hepatitis vaccines, malaria vaccines, herpes vaccines, papilloma vaccines, influenza vaccines, and small pox vaccines. Various cancer vaccines have been developed which can be administered with an early activation molecule antagonist described herein. Examples of such cancer vaccines include, but are not limited to, autologous tumor cell vaccines; allogeneic tumor cell vaccines; gangliosides (e.g., for melanoma or sarcoma); CEA (e.g., for colorectal cancer, other gastrointestinal malignancies, pancreatic and breast cancer); PSA (e.g., for prostate cancer); MART-1 100, tyrosinase (e.g., for melanoma); p53 (for various p53 expressing cancers); alpha-fetoprotein (AFP) (e.g., for liver cancers such as hepatomas).

The early activation molecule antagonist can be administered to the subject, prior to, concurrent with or after the administration of the antigen.

The dose levels can be determined based upon the antigen used. In addition, the timing of dosing and the adjuvant used, if any, can be determined by methods known in the art.

EXAMPLES

To ascertain the functional in vivo role of CD69 in autoimmune reactivity and inflammation, the behavior of CIA in CD69 deficient B6 mice was analyzed. An exacerbated form of CIA was observed in CD69$^{-/-}$ mice that correlated with collagen type II (CII) specific T and B cell responses, an increase in some inflammatory mediators, and diminished local TGF-θ synthesis. Local blockade of TGF-θ increased severity in wildtype but not CD69 deficient mice. In addition, in vitro engagement of CD69 induced the production of TGF-θ1. These results strongly suggest that CD69 is a negative regulator of autoimmune reactivity through TGF-θ synthesis. Also, an enhanced NK-dependent anti-tumor response in CD69$^{-/-}$ mice is described. The influence of CD69 deficiency on the anti-tumor response leads to a higher protection and rejection of MHC class I-tumor cells as compared to wt mice. This potent anti-tumor response was dependent on the tumor-host microenvironment, correlating with a diminished production of TGF-β, an increase in inflammatory cytokines and the chemokine MCP-1, and was associated with increased recruitment of lymphoid effector cells and diminished apoptosis. The enhanced anti-tumor response was NK cell- and T lymphocyte-mediated and persisted in immuno-compromised CD69$^{-/-}$ RAG-negative mice. Moreover, in vivo treatment with an anti-TGF-β mAb induced an enhanced tumor response. In addition, engagement of CD69 induced extracellular signal-regulated kinase (ERK) activation and TGF-β production by T cells. Blockade of ERK by PD98059 inhibits TGF-β production, directly linking CD69 signaling with TGF-β regulation. Furthermore it is demonstrated that, in vivo treatment with the antagonist 2.2 anti-CD69 mAb induced enhanced anti-tumor response in wildtype mice and in immuno-compromised SCID and RAG-deficient mice challenged with MHC class-I negative cells.

These results indicate that CD69 is a negative regulator of immune reactivity through TGF-β1 synthesis. In vivo treatment with anti-CD69 antibodies results in different effects depending on the anti-CD69 used. The antagonist 2.2 anti-CD69 mAb enhances the immune response, resulting in increased CIA severity and a more efficacious tumor rejection. The depleting 2.3 anti-CD69 antibody deletes CD69+ activated effector leukocytes, resulting in attenuated CIA. In addition, this antibody may directly eliminate CD69+ tumors.

With regard to the use of transgenic mice for the production of a human monoclonal antibody specific for the human CD69 antigen, Molina et al. (2003) describe in detail, and provide materials and methods for, the isolation and characterization of hAIM-29 mAb (IgM/λ), which, based on its high specificity to the human CD69 antigen and by some of its functional properties, can have therapeutic uses in treating or preventing diseases associated with the presence of activated cells expressing CD69 antigen.

The following examples are useful to illustrate the invention and should not be considered as limiting of the claims covered by this invention:

Example 1

CD69-Deficient Mice Develop an Exacerbated CIA

Figure 1B:
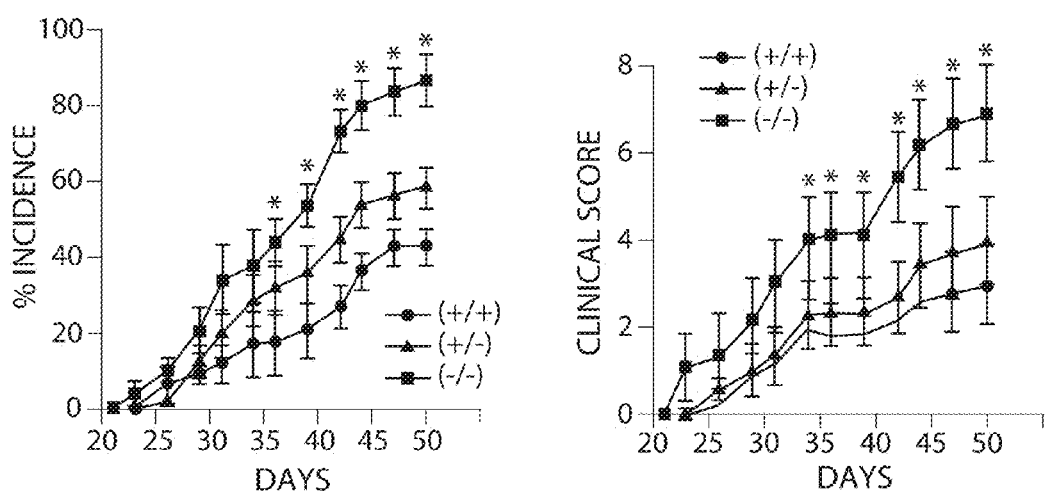

To explore the role of CD69 in a model of chronic autoimmune arthritis, interbred B6 WT and CD69$^{-/-}$ mice (Lauzurica et al., 2000) were compared for incidence and severity of CIA induced by intradermal immunization with CII in CFA, which elicits a moderate arthritis in B6 mice (Campbell et al., 2000). CD69-deficient mice developed an exacerbated form of CIA, with severe swelling of the footpad, ankle/wrist joints and digits (FIG. 1a), and significantly higher incidence and severity compared to WT mice (FIG. 1b). Furthermore, CD69$^{+/-}$ mice, which express intermediate levels of CD69 (Lauzurica et al., 2000), showed a higher incidence and severity of CIA than WT mice, but significantly lower than CD69$^{-/-}$ mice (FIG. 1b).

Figure 2A:
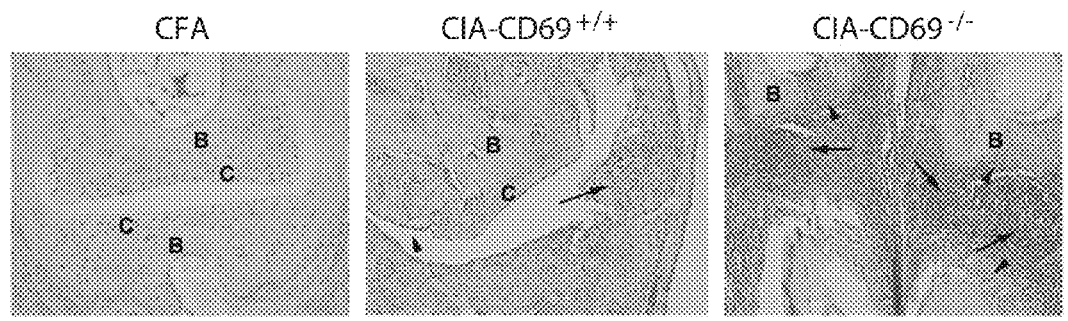
FIG. 2. A. Representative section of joint histopathology on whole paws of control (CFA, left, 100×), and CII-immunized $CD69^{+/+}$ (middle panel, 100×) and $CD69^{-/-}$ (right panel, 60×) mice. Arrowheads indicate cartilage and bone erosions, and arrows indicate leukocyte infiltrates and pannus. B. scoring of inflammation, cartilage damage, pannus formation, and bone erosion of paws from $CD69^{+/+}$ (□) and $CD69^{-/-}$ (■) mice as described in Methods. Results are expressed as the arithmetic mean±s.d. of the percentage of joints ascribed to each severity group from three independent experiments (8 mice/group/experiment)*, P<0.01 vs. $CD69^{+/+}$ (Mann-Whitney U test).
Figure 2B:
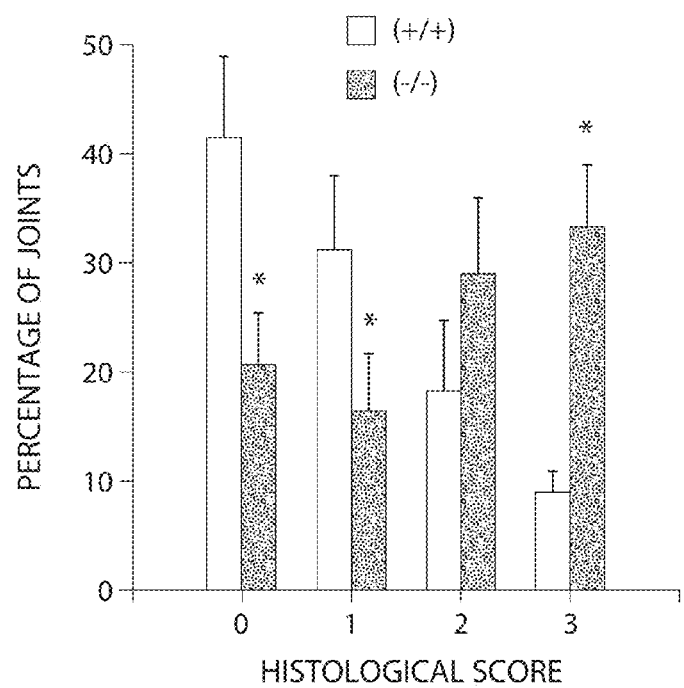

To further evaluate arthritis, hematoxylin and eosin-stained sections of paws from CD69$^{-/-}$ and WT mice with different grades of CIA were assessed by histological analyses. These studies paralleled the results shown for clinical evaluation, with a significantly higher percentage of joints with severe pathology observed in CD69$^{-/-}$ mice compared to WT mice (FIG. 2A). Joints from CD69-deficient mice more frequently showed widespread infiltration of inflammatory cells, with pannus tissue extending from marginal zones to cartilage and through the medulla of subchondral bone (FIGS. 2A, and B). In late stage disease, there was destruction of articular cartilage and bone, with loss of normal joint architecture. Therefore, these results showed a clear-cut inverse correlation between CIA severity and expression of CD69, suggesting in vivo inhibitory role for CD69 in CIA development.

Example 2

Enhanced Collagen type II-Specific Immune Response in CD69$^{-/-}$ Mice

Figure 3A:
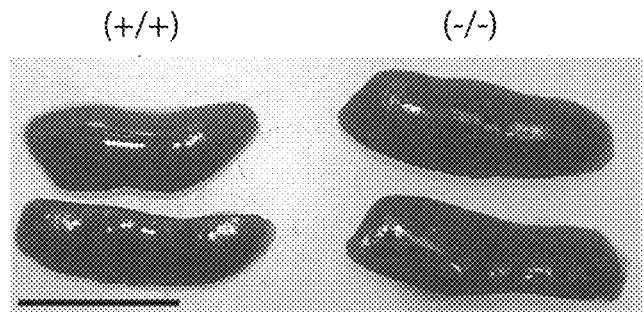
FIG. 3. Enhanced CII-specific immune response in $CD69^{-/-}$ mice. a, enlarged spleens of $CD69^{-/-}$ compared to $CD69^{+/+}$ mice. Horizontal bar=1 cm. b, spleen weight and cell number (arithmetic mean±s.d.) from CFA control and CII-immunized (CIA) $CD69^{+/+}$ (□) and $CD69^{-/-}$ (■) mice are shown. *, P<0.01, compared with WT immunized mice (Student's t test). c, proliferation of spleen (Sp) and lymph node (LN) cells from CII-immunized $CD69^{+/+}$ (□) and $CD69^{-/-}$ (■) mice stimulated with different concentrations of inactivated CII (x-axis). Data correspond to the arithmetic mean±s.d. of $^3$H-TdR uptake in three independent experiments. *, P<0.01 versus $CD69^{+/+}$ (Mann-Whitney U test). d, Increment of CII-specific Th1-dependent isotypes in $CD69^{+/+}$ mice. CII-specific IgG1 and IgG2b (1/20000 serum dilution), IgG2c and IgG3 (1/5000 serum dilution), and IgM and IgA (1/200 serum dilution) antibody levels in sera collected at sacrifice (50 d) of CFA-treated control or CII-immunized (CIA) $CD69^{+/+}$ (□) and $CD69^{-/-}$ (■) mice. Data are represented as the arithmetic mean±s.d. of absorbance units at 495 nm in three separate experiments (10 mice/group/experiment). *, P<0.01 versus CD69+/+(Student's t test).
Figure 3B:
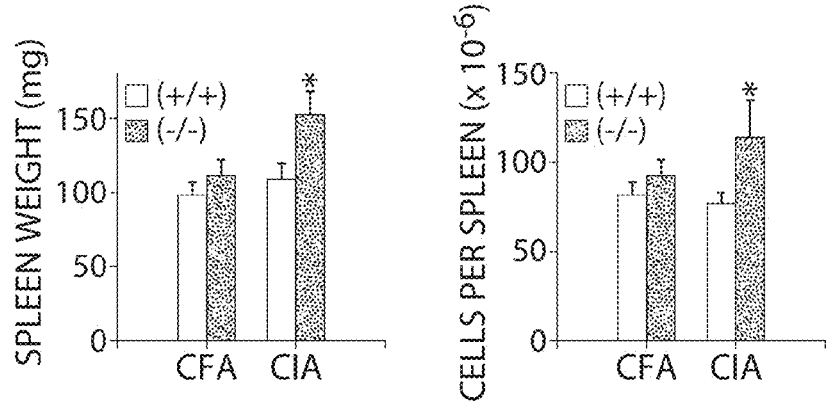

These results strongly suggested that CII triggers exacerbated immune response in CD69$^{-/-}$ mice. Accordingly, the spleen was significantly enlarged in CD69$^{-/-}$ CII-challenged mice (about 1.4 fold heavier, p<0.001, t test) compared to WT mice at 13 wk of age, suggesting a higher activation of the immune system in arthritic CD69-/- mice (FIG. 3A, B). The increase in spleen weight correlated with an increased cellularity (FIG. 3B). Next, we ascertained whether this increment in cellularity was due to a difference in any subpopulation of immune cells present in the spleen. The proportion of T cells, B cells, macrophages, and NK cells as well as CD4/CD8 ratio, naïve/effector-memory cells (CD62L/CD44) and the CD45low CD25+ CD4+ regulatory T cells were analyzed. The proportion of these subsets was conserved between WT and CD69$^{-/-}$ mice either in the absence of any stimulation or after CII challenge (not shown).

Figure 3C:
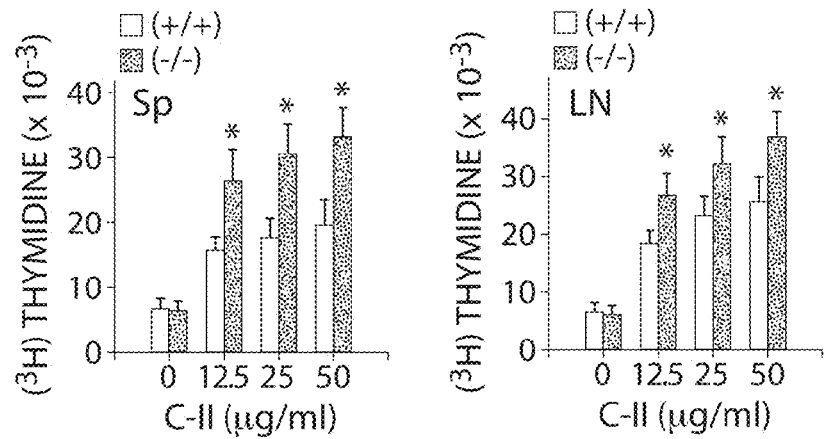

To assess lymphocytes reactivity, the CII-specific proliferative response of lymphocytes from spleen and lymph nodes were analyzed. Lymphocytes from CD69−/− mice proliferated to a significantly higher extent than WT mice at the different doses of CII tested (FIG. 3C), indicating an inhibitory influence of CD69 in the CII-specific proliferation of immune cells form CII-challenged mice.

Figure 3D:
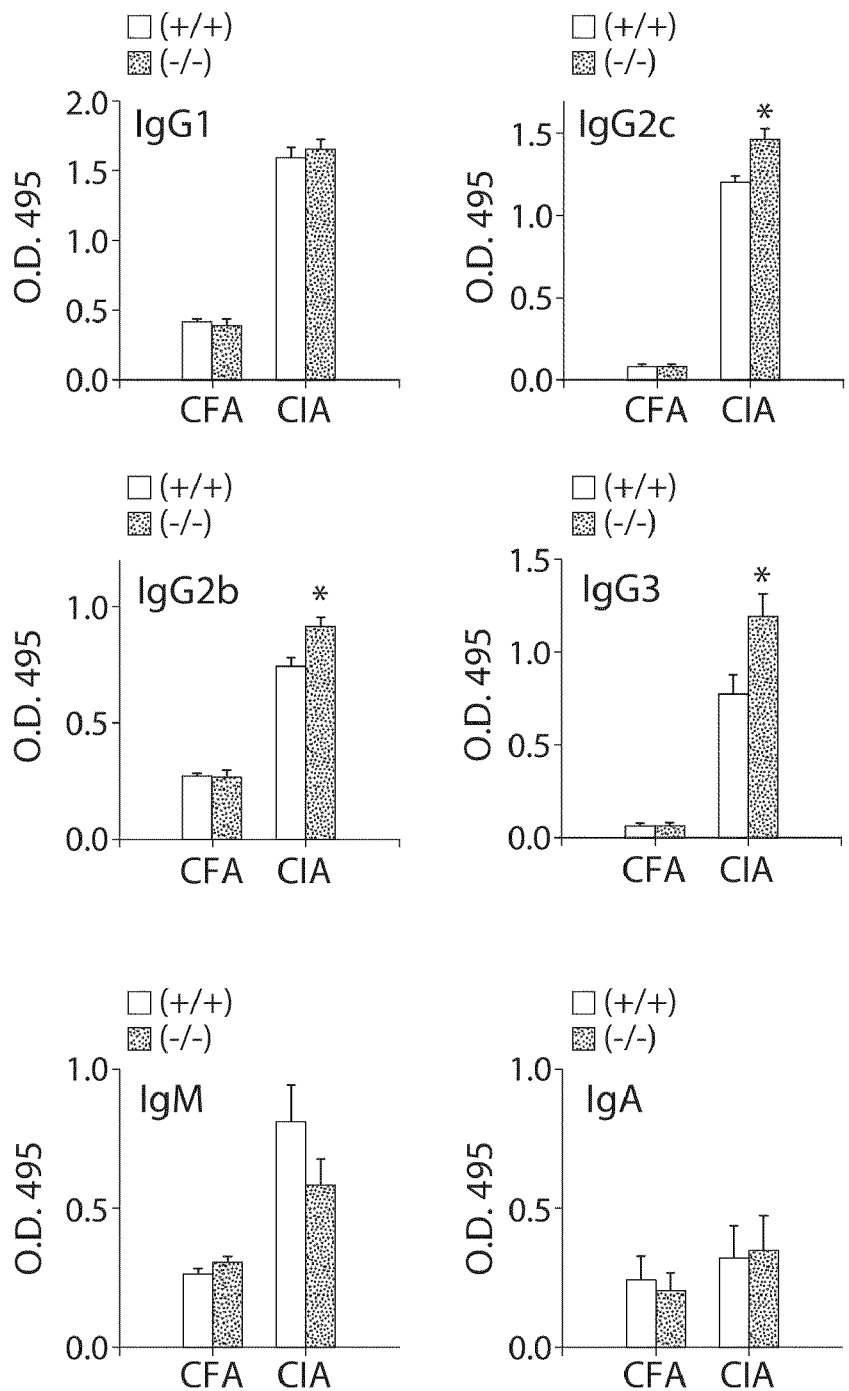

The humoral response to CII was also investigated. Analysis of serum concentration of anti-CII isotypes showed significantly augmented levels of the Th1-dependent isotypes IgG2c, which is equivalent in B6 mice to IgG2a, and IgG2b (FIG. 3D). A significant increment in IgG3 was also found, indicating B cell hyperresponsivness in CD69−/− mice, while the reduction in IgM would suggest enhanced shift to IgG. The Th-2 dependent IgG1 was not significantly different, and CII did not induce a significant IgA response. Altogether, these results suggest a stronger T and B cell immune reactivity in CD69-deficient mice.

Example 3

CD69-Deficient Mice show a Diminished Local TGF-β1 Production

Figure 4:
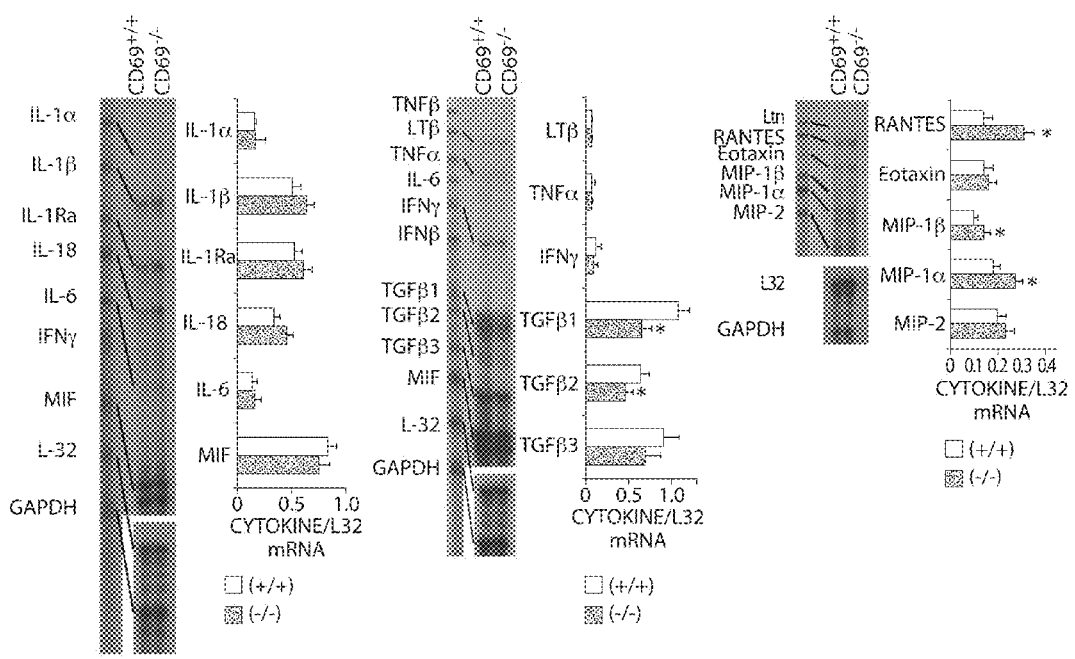
FIG. 4. Local cytokine mRNA analysis in CII-immunized $CD69^{-/-}$ mice. mRNA analysis of CIA $CD69^{+/+}$ (□) and $CD69^{-/-}$ (■) mouse hind paws. Each lane corresponds to the mRNA pool of 6 mice per group, and each bar represents similar experiments (6 mice/group/experiment). Results are expressed in arbitrary densitometric units normalized for L-32 expression in each sample (arithmetic mean±s.d. of four separate experiments). *, P<0.01 versus $CD69^{+/+}$ (Mann-Whitney U test).
Figure 5A:
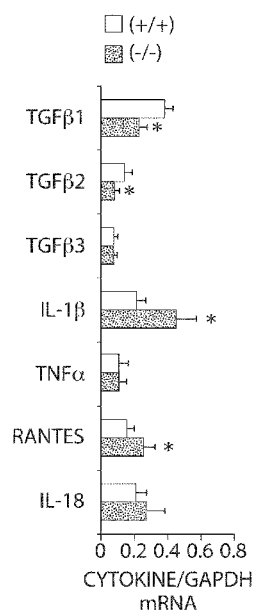
FIG. 5. Local cytokine analysis in joints and purified leukocyte synovial cells from CII-immunized $CD69^{-/-}$ mice. A, Real-time quantitative RT-PCR analysis of mRNA from $CD69^{+/+}$ (□) and $CD69^{-/-}$ (■) mouse hind paws. Each bar represents the arithmetic mean±s.d. of 12 mice per group in two independent experiments. Results for each cytokine are normalized to GAPDH expression measured in parallel in each sample. *, P<0.01 versus $CD69^{+/+}$ (Mann-Whitney U test). B, Levels of active and total TGF-β1, IL-1β, TNF-α, and RANTES in synovial washouts from CIA $CD69^{+/+}$ (□) and $CD69^{-/-}$ (■) mice. Data correspond to the arithmetic mean±s.d. of three independent experiments (6 mice/group/ experiment). *, P<0.01 versus $CD69^{+/+}$ (Mann-Whitney U test). C, quantitative RT-PCR analysis of mRNA from $CD69^{+/+}$ (□) and $CD69^{-/-}$ (■) purified subsets of synovial cells. Each bar represents the arithmetic mean±s.d. of 12 mice per group in two independent experiments. Results of each cytokine are normalized to GAPDH expression measured in parallel in each sample. *, P<0.01 versus $CD69^{+/+}$ (Mann-Whitney U test).

A wide array of cytokines are involved in inflammation and development of arthritis (O'Shea, J. J., et al. 2002. *Nat. Rev. Immunol.* 2:37-45; Feldmann, M., et al. 1996. *Ann. Rev. Immunol.* 14:397-440. Campbell, I. K., et al. 2001. *J. Clin. Invest.* 107:1519-27.). Since the joints are the most relevant site of cytokine production in arthritis, we tested how CD69 deficiency could affect the profile of cytokine expression in joints of mice with CIA. Rnase protection assays showed that CD69 deficiency enhances mRNA expression of some inflammatory mediators such as IL-1β, RANTES, MIP-1$_\chi$, and MIP-1β (FIG. 4). However, the most significant difference was the reduction in mRNA levels of the anti-inflammatory cytokines TGF-β and β2 in CD69$^{-/-}$ mice (FIG. 4). Real time quantitative RT-PCR analyses confirmed the reduction in joint mRNA for TGF-β1 and β2, and the increase in IL-1β and RANTES (FIG. 5A).

Figure 5B:
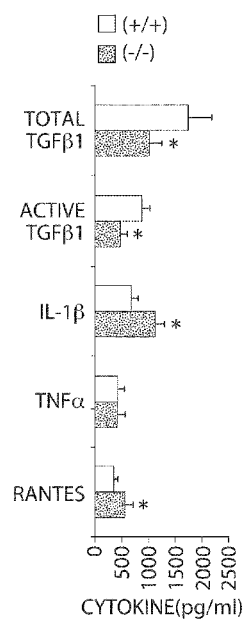

Next, the levels of active and total TGF-β1 protein, directly produced by activated leukocytes (Kehrl, J. H., et al. 1986. *J Exp Med.* 163:1037-50.), and other cytokines in washouts of joint tissue from CIA-challenged mice at sacrifice, were detected. In contrast to the unchanged systemic levels of TGF-β1 (not shown), active and total TGF-β1 levels in synovial washouts were significantly reduced in CD69-deficient mice (FIG. 5B.). In contrast, pro-inflammatory cytokines such as IL-1β and RANTES were increased in synovial washouts form CD69$^{-/-}$ mice respect to WT, whereas TNF-α levels remained locally unchanged (FIG. 5B). Since TGF-β1 is considered an anti-inflammatory cytokine with a predominant protective role in CIA (Kuruvilla, A. P., et al. 1991. *Proc. Natl. Acad. Sci. USA.* 88:2918-2921), these results suggest that deficient local production of this cytokine may account for the enhanced inflammatory response observed in CD69$^{-/-}$ mice through the augmented production of IL-1β and different chemokines, thus altering the balance between pro- and anti-inflammatory cytokines at synovium (O'Shea, J. J., et al. 2002. *Nat. Rev. Immunol.* 2:37-45).

Figure 5C:
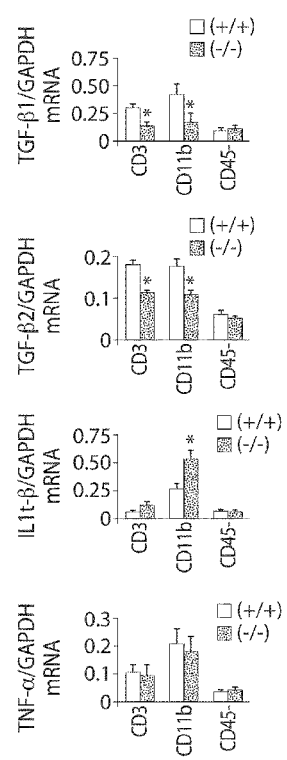

To ascertain the cell population responsible for the pattern of cytokine expression seen in CD69$^{-/-}$ mice, purified synovial cells from CIA-challenged mice were analyzed. Synovial cells were mainly CD11b+ macrophages (66.3±29.4%), with some CD3+ cells (9.6±5.3%), and non-leukocyte CD45- cells (24.1+14.8%). The three subsets were isolated and quantitative RT-PCR revealed that both CD3+ and CD11b+ leukocytes contributed to TGF-β decrease in CD69-deficient mice. Nevertheless, the CD11b+ subset was responsible for the subsequent higher proinflammatory response mediated by IL-1β (FIG. 5C), likely playing a crucial role in the perpetuation of synovitis.

Example 4

Blockade of TGF-β Increases CIA Severity in WT but not in CD69-Deficient Mice

Figure 6A:
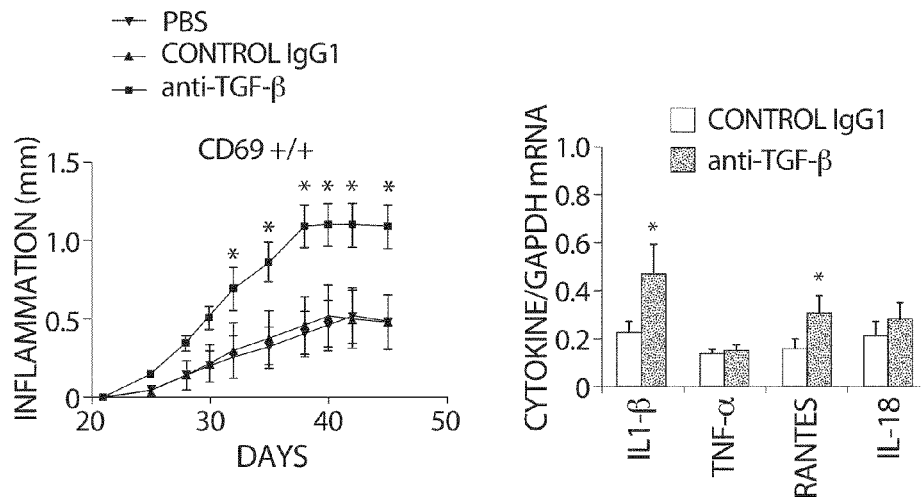
FIG. 6. Effect of a blocking anti-TGF-β in WT and CD69-deficient mice. a, left panel: $CD69^{+/+}$ mice were treated from day 21 ($2^{nd}$ immunization) with the blocking anti-TGF-β (■), the isotype control IgG1 (σ), or the carrier (τ). Paw inflammation measured with a precision caliper is expressed as mm of inflammation with respect to day 21. Results express the arithmetic mean±s.d. of 12 mice per group in two independent experiments. Right panel: analysis by quantitative real-time RT-PCR of mRNA from paws treated with isotype control antibody (□) or with anti-TGF-β(■). Each bar represents the arithmetic mean±s.d. of 12 mice per group in two independent experiments. Results of each cytokine are normalized to GAPDH expression measured in parallel in each sample. *, P<0.01 versus control antibody (Mann-Whitney U test). b, $CD69^{-/-}$ mice were treated as in a, paw inflammation measured (left panel) and mRNA determined (right panel) as above.

The protective effects of TGF-1 in CIA could explain by themselves the deregulation of the balance of some pro-inflammatory and chemotactic cytokines (O'Shea, J. J., et al. 2002. *Nat. Rev. Immunol.* 2:37-45; Kuruvilla, A. P., et al. 1991. *Proc. Natl. Acad. Sci. USA.* 88:2918-2921; Brandes, M. E., et al. 1991. *J. Clin. Invest.* 87:1108-1113.). These results would explain the higher infiltration of leukocytes and inflammatory responses in joints from CD69 deficient mice. To establish a functional link between TGF-β activity and CIA severity, a blocking anti-TGF-β (Dasch, J. R., et al. 1989. *J. Immunol.* 142:1536-41) was locally injected in paws from CIA WT mice. TGF-β blockade induced a significant increase in paw inflammation, compared to control antibody or carrier (FIG. 6A). Joint mRNA analysis by quantitative RT-PCR showed a significant increase in IL-1β and RANTES, but not in TNF-α and IL-18 (FIG. 6A). These results indicated that TGF-β blockade in CIA WT mice results in a similar phenotype to that seen in CD69-deficient mice.

Figure 6B:
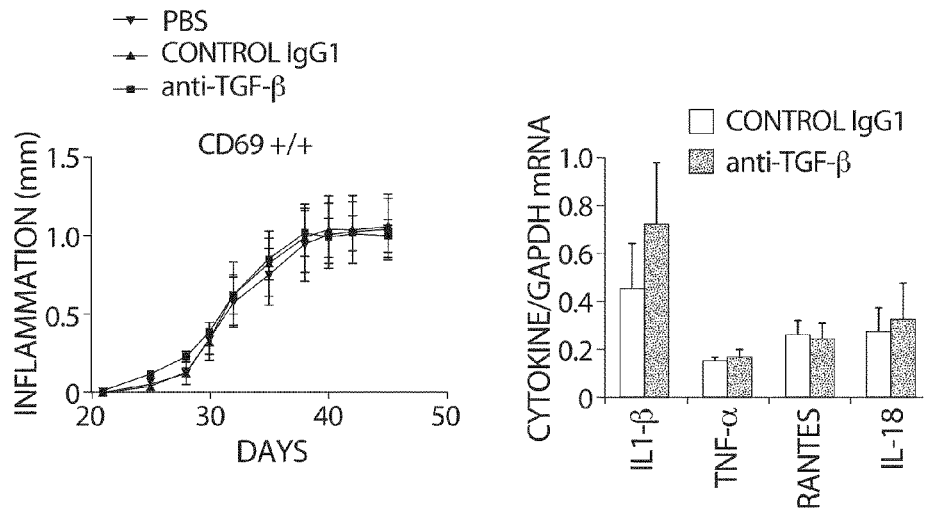

In contrast, local injection of anti-TGF-β in CIA CD69$^{-/-}$ mice did not further enhance paw inflammation (FIG. 6B). Accordingly, mRNA analyses showed no significant modification in the mRNA levels for pro-inflammatory cytokines. These findings reveal that TGF-β blockade and CD69 deficiency do not cooperate to increase CIA severity, suggesting their inter-dependence.

Example 5

Induction of TGF-β1 Production by CD69 Engagement

Figure 7A:
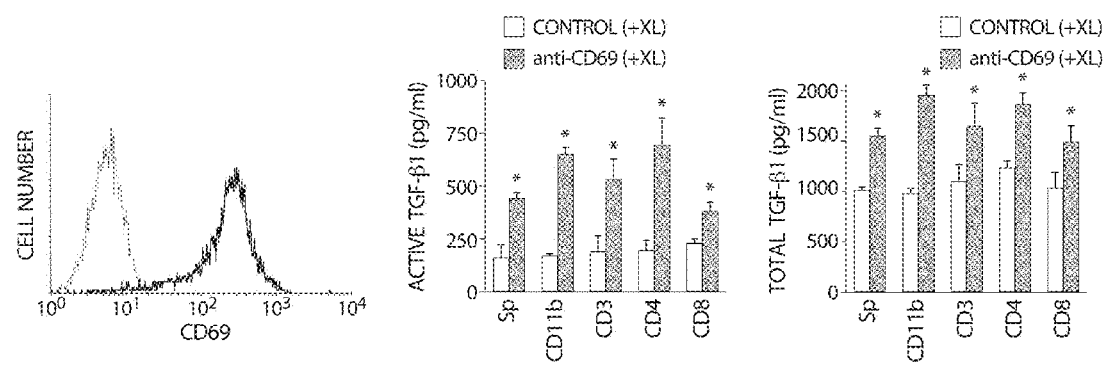
FIG. 7. CD69 engagement induces TGF-β1 secretion in mouse splenocytes and synovial leukocytes from CIA mice A, Con-A stimulated splenocytes were stained for CD69 (thick line, left panel) and an isotype-matched antibody (dotted line, left panel). Activated splenocytes were then purified in different subsets and treated with an anti-mouse CD69 (■), or an isotype-matched control antibody (□), and a cross-linking secondary antibody was added. Active and total TGF-β1 was determined (right panels). B, mouse synovial cells from CIA mice were stained for CD11b and CD69 (middle panel), or isotype control Abs (left panel). Synovial cells were treated as in A, and active and total TGF-β1 determined (right panels). Results in A and B are expressed as the arithmetic mean±SD of four independent experiments. *, p<0.01 versus control antibody (Mann Whittney U test).
Figure 7B:
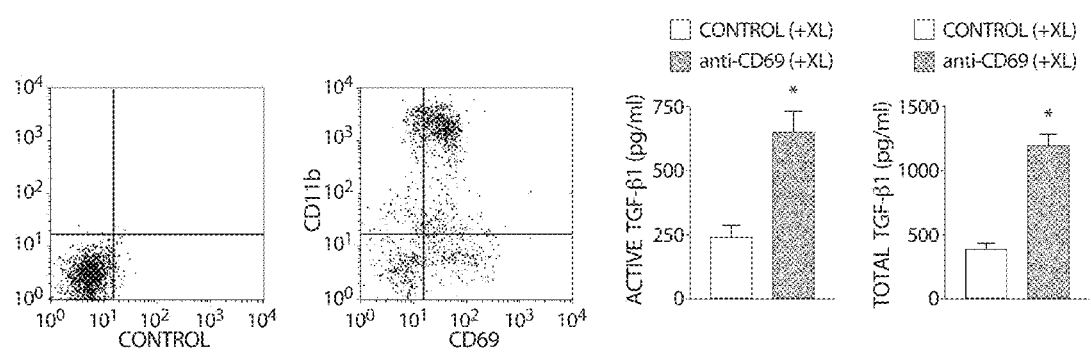

To analyze whether CD69 is able to regulate TGF-β synthesis, we examined production of TGF-β1 following CD69 engagement in ConA-activated mouse splenocytes (FIG. 7A). CD69 cross-linking markedly induced total and active TGF-β1 production in different leukocyte cell subsets (FIG. 7A), concurring with data on NK cells and anti-CD3 activated splenocytes (Esplugues, E. et al. 2003. *J. Exp. Med.* 197: 1093-1106.). Moreover, CD69 cross-linking triggered TGF-β1 production in infiltrating synovial cells from WT mice with CIA, most of them CD11b+ cells bearing CD69 (FIG. 7B). In contrast, we did not detect any differences in synthesis of TNF-α, RANTES, or IL-1β following CD69 cross linking (not shown).

Figure 8A:
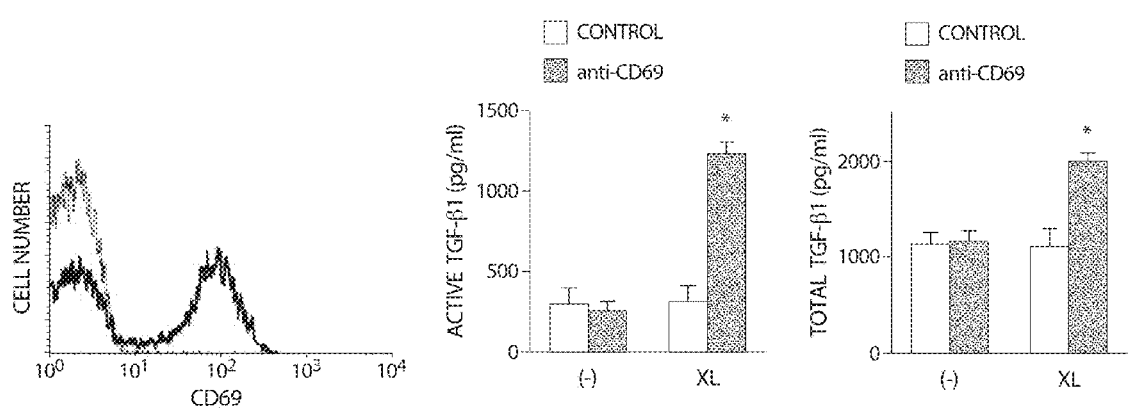
FIG. 8. CD69 crosslinking induces TGFθ1 production in human synovial leukocytes and in human CD69 T cell stable trasfectants. A, human synovial leukocytes from patients with rheumatoid arthritis were stained for CD69 (thick line, left panel), and isotype-matched antibody (dotted line, left panel). Synovial leukocytes were treated with anti-human CD69(■), or an isotype-matched control antibody (□) in the presence (XL) or absence (−) of a cross-linking secondary Ab, and active and total TGF-β1 determined (right panel). *, P<0.01 versus control antibody (Mann-Whitney U test). These results are representative of similar data obtained on synovial leukocytes from patients with reactive arthritis or ankylosing spondylitis. B, Jurkat human T cell leukemic cell line (dotted line, left panel), and CD69 stable transfectants (thick line, left panel) were stained for CD69. Production of TGFθ1 but not TNF-1 by CD69 engagement (right panel). The human T lymphoblastoid cell line Jurkat (JK) (η) and the stable transfectant expressing CD69 (JK-CD69)(■) were treated for 24 hours with cross linked anti-CD69 antibody. Results in A and B are expressed as the arithmetic mean±SD of four independent experiments. *, p<0.01 respect to the parental JK cell line (Mann Whittney U test).

To ascertain whether these results could be extended to humans, we analyzed TGF-β1 production in CD69+ synovial mononuclear cells from patients with inflammatory joint disease (FIG. 8A). Cross-linked, but not soluble, anti-CD69 induced TGF-β1 synthesis independently of further co-stimulus (FIG. 8A), whereas no differences were found for other cytokines, such as TNF-α or IL-6 (not shown). In CD69-mediated TGFβ1 production assays, increased active TGF-β1 correlated with total TGF-β1 synthesis (FIGS. 7 and 8). These results demonstrate that, both in mice (FIG. 7) and humans (FIG. 8), there is a direct link between CD69 engagement and TGF-β1 synthesis, and may explain the higher TGF-β1 levels found in CD69$^{+/+}$ mice compared to CD69$^{-/-}$ mice.

Figure 8B:
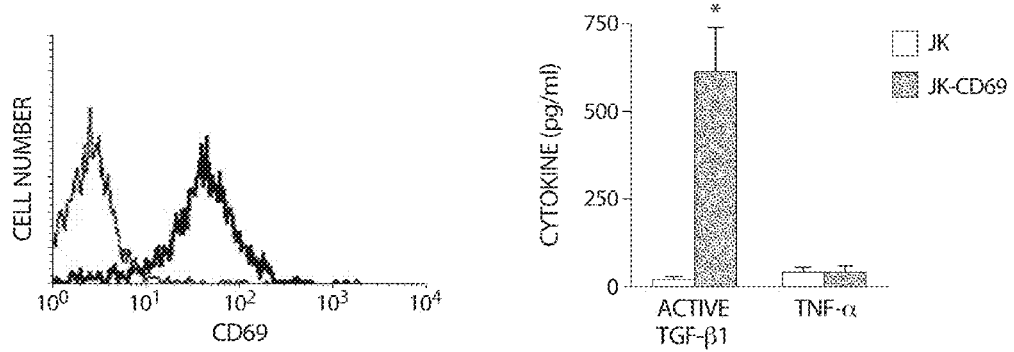

To establish a direct connection between CD69 cross-linking and TGF-β1 production we took advantage of Jurkat T cells stably transfected with human CD69 (JK-CD69). The CD69 expressing JK-CD69 produced significant active TGF-β after cross-linking with anti-CD69 antibodies, in contrast to the absence of TGF-β synthesis in the parental CD69 negative Jurkat T cell line (FIG. 8B). In addition, our data showed that cross-linking of CD69 failed to induce TNF-α production (FIG. 8B). Taken together, these results establish that CD69, a receptor expressed following activation, down-regulates the autoimmune response and the inflammatory reaction through direct secretion of active TGF-β at inflammatory foci.

Example 6

In Vivo Treatment of CIA with Anti-CD69 Antibody

The effect of in vivo treatment with anti-CD69 antibody has been analyzed using two different anti-CD69 antibodies, mAb 2.2 and mAb 2.3, in the CIA model in DBA1 wild type mice.

MAb 2.2 behaves in vitro as a non-depletor antibody. An IgG1, it is unable to bind complement and does not lyse CD69 expressing cells in an in vitro chromium assay (not shown). Furthermore, mAb 2.2 does not induce TGF-b synthesis in vitro in the absence of crosslinking (Esplugues et al. 2003. J. Exp. Med. 197:1093; Sancho et al. 2003. J. Clin. Invest. 112:872).

Figure 22:
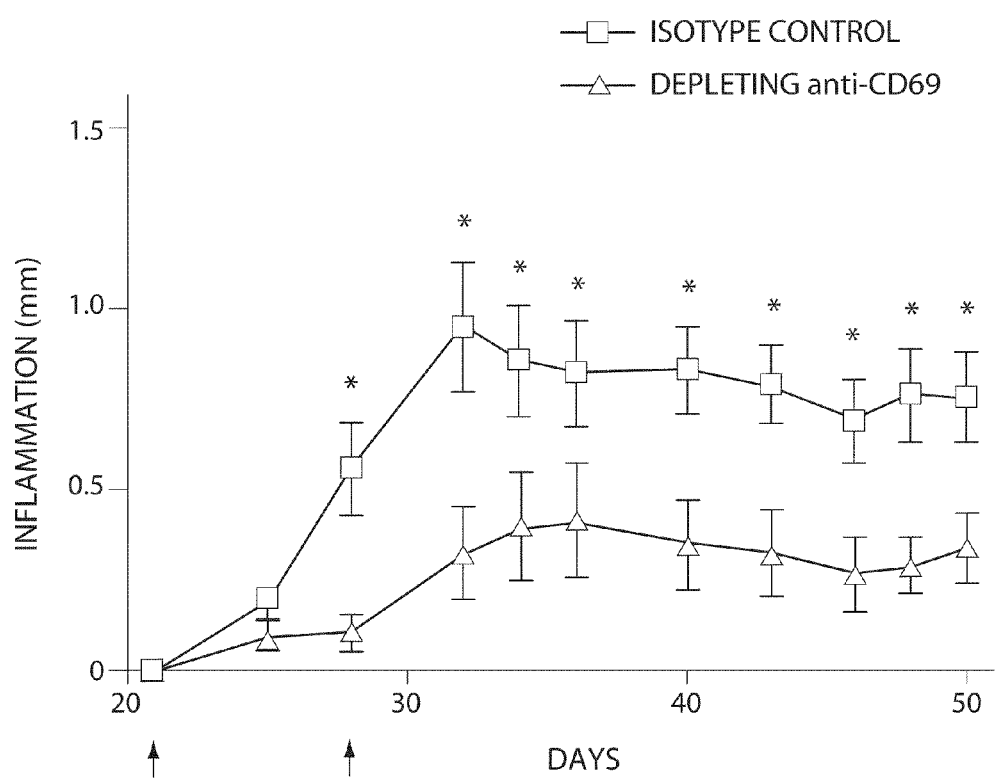
FIG. 22. Effect of treatment with 2.3 anti-CD69 mAb in CIA. DBA/1 mice were treated at days 20 and 28 with the depleting anti-CD69 mAb (A), or the isotype control IgG2a mAb (■). Paw inflammation measured with a precision caliper is expressed as mm of inflammation relative to the day 21 value. Results are expressed as the arithmetic mean±s.d. of 12 mice per group in two independent experiments. *, P<0.01 versus control antibody (Mann-Whitney U test).

The effect of 2.2 anti-mouse CD69 antibody was analyzed in vivo in a model of CIA in DBA/1 mice. In vivo treatment with this antibody leads to the complete loss of expression of CD69 in populations that express the molecule, such as CD3$^{hi}$ thymocytes (FIG. 22). As shown in the upper right quadrant of the left panel, 14.2% of thymocytes express CD69. Following mAb 2.2 treatment, only 0.9% express CD69 (upper right quadrant, right panel). However, the total thymocyte pool remains constant, since the sums of the upper quadrants in each panel are the same, namely 20.7% (6.5+14.2 for control and 19.8+0.9 for treated). This shows that mAb 2.2 does not mediate depletion of CD69+ cells in vivo. Further studies show that mAb 2.2 removes CD69 from the cell surface, i.e., antagonizes by down-modulation of CD69.

The treatment of CIA-induced DBA/1 mice with mAb 2.2 significantly exacerbated CIA when administered at days 20 and 28 during the initiation of the secondary response (FIG. 23), in agreement with our results in CD69-deficient mice (FIG. 1).

Quantitative RT-PCR analysis of mRNA from isotype control treated and anti-CD69 mAb 2.2-treated wildtype mouse hind paws showed that levels of IL-1θ were increased [25.0+/−9 to 58.4+/−8 units, p<0.01 (Mann-Whitney U test)] and TGF-θ1 were decreased [56.5+/−13 to 18.2+/−8 units, p<0.01 (Mann-Whitney U test)]. Levels of IL-4, TNF, MCP-1, and IFN-gamma mRNA were unchanged (N=12 mice per group in two independent experiments. Results for each cytokine are normalized to GAPDH expression measured in parallel in each sample). The results show that down-modulation of CD69 by mAb 2.2 leads to decreased TGFθ1 mRNA, and increased IL1θ mRNA levels, consistent with the observed exacerbation of inflammation.

MAb 2.3 behaves in vitro as a depletor antibody. As an IgG2a, it binds complement and lyses CD69-expressing cells in an in vitro chromium assay (not shown).

The effect of mAb 2.3 was also analyzed in vivo in a model of CIA in DBA/1 mice. In vivo treatment with this antibody leads to the depletion of CD69-expressing CD3$^{hi}$ thymocytes (FIG. 24). As shown in the upper right quadrant of the left panel, in this experiment 16.7% of thymocytes express CD69. Following mAb 2.3 treatment, only 0.1% express CD69 (upper right quadrant, right panel). However, the total thymocyte pool is strongly reduced, since the sums of the upper panels are now different, namely 24.8% in the control, but only 8.3% in the treated group. This shows that mAb 2.3 has depleted all CD69-expressing cells, rather than functionally 'blocking' CD69.

The treatment of CIA-induced DBA/1 mice with mAb 2.3 significantly reduced CIA when administered at days 20 and 28 during the initiation of the secondary response (FIG. 25).

These results show that the treatment with a down-modulating anti-CD69 could be useful to enhance certain immune responses. In contrast, the depletion of CD69 expressing cells may ameliorate diseases mediated by the activation of the immune system.

Example 7

CD69-Deficient Mice Develop an Enhanced Anti-Tumor Response

Figure 9A:
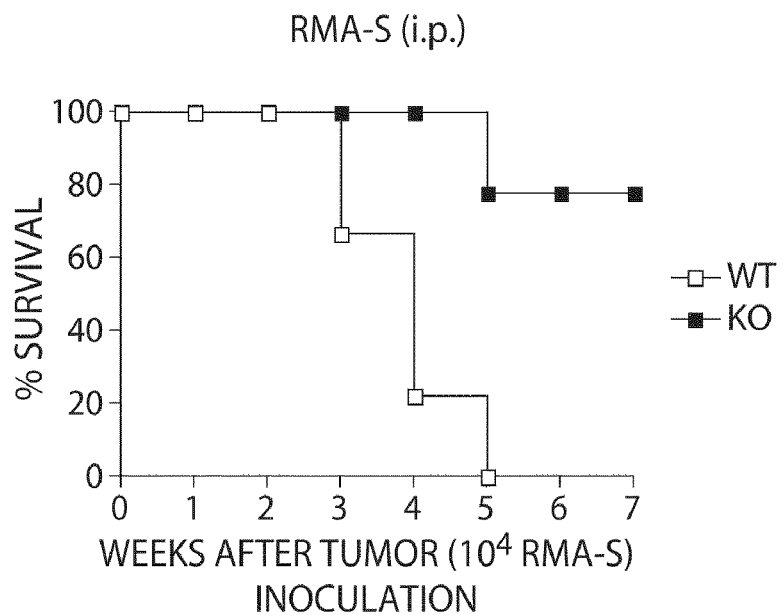
FIG. 9. Increased anti-tumor activity in CD69$^{-/-}$ mice. Mice were injected intraperitoneally with $10^4$RMA-S (A) or RMA (C) tumor cells. Mice were observed daily for tumor growth up to 12 weeks by monitoring body weight and development of ascites. Similar results were observed in mice injected subcutaneously with $10^5$ RMA-S (B). (A, n=9; B, n=6; C, n=9). (D) NK or T lymphocytes were depleted from CD69$^{-/-}$mice before intraperitoneal inoculation with $10^4$RMA-S tumor cells. Mice were treated for NK cell depletion on day −1 (before tumor challenge), and at days+2, and +4 after tumor inoculation with either control diluent or anti-Asialo GM1 antiserum (100 μl/injection). (D, n=7). Mice were treated for Lymphocyte T CD4+ depletion on day −1 (before tumor challenge), and at days+2, and +4 after tumor inoculation with either GK1.5 anti-CD4 or isotype control mAbs (100 μl/injection). (D, n=7) Results shown are representative of two independent experiments. Open symbols represent wt mice and solid symbols represent CD69$^{-/-}$ mice. (E) Photographs are of lungs from CD69$^{-/-}$ and wt mice 2 weeks after the challenge with $10^4$ RM-1 cells i.v. inoculation (upper). One representative mouse out of 10 per group is shown. Number of lung metastases was counted (lower) and each symbol represents one mouse. Open symbols represent wt mice and solid symbols, CD69-mice. Results are representative of two independent experiments.
Figure 9B:
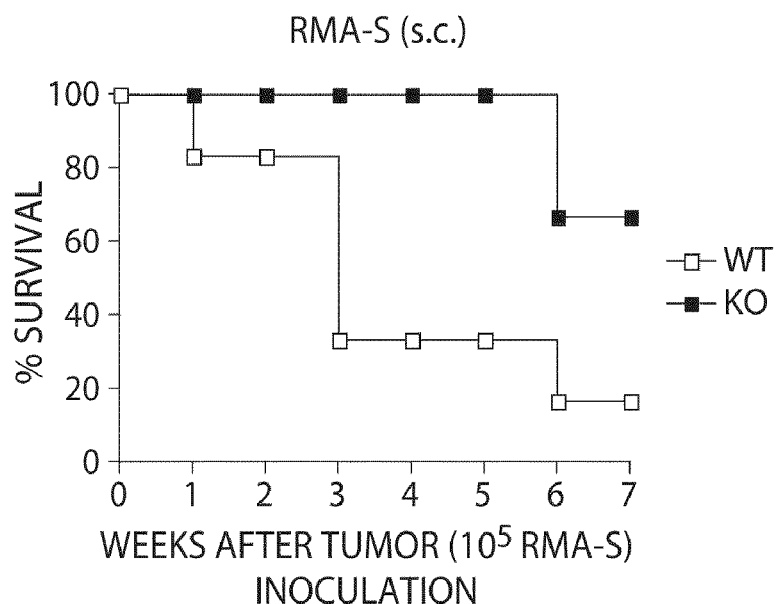
Figure 9C:
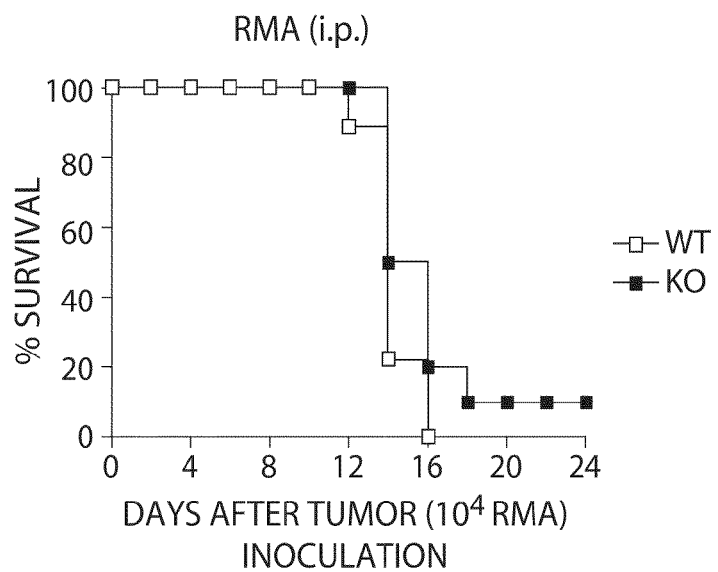

To evaluate the possible role of CD69 in in vivo anti-tumor function, wild type (wt) and CD69$^{-/-}$ mice were injected i.p. with RMA-S cells and tumor progression was analyzed (FIG. 9A). In response to 10$^4$ RMA-S cells, all wt mice developed tumors by 5 weeks, with a detectable increase of weight at day 15, whereas only 20% of CD69$^{-/-}$ mice developed detectable tumors even as late as 7 weeks (FIG. 9A). Similar results were observed when mice were subcutaneously injected with 10$^5$ RMA-S (FIG. 9B), indicating that there are no appreciable differences due to the site of tumor challenge. In contrast, only slight differences were observed in the progression of H-2$^+$ RMA cell tumors between wt and CD69$^{-/-}$ mice (FIG. 9C, and data not shown), thus suggesting that CD8$^+$ CTLs play a minor role in the enhanced anti-tumor response observed in CD69$^{-/-}$ mice.

Figure 9D:
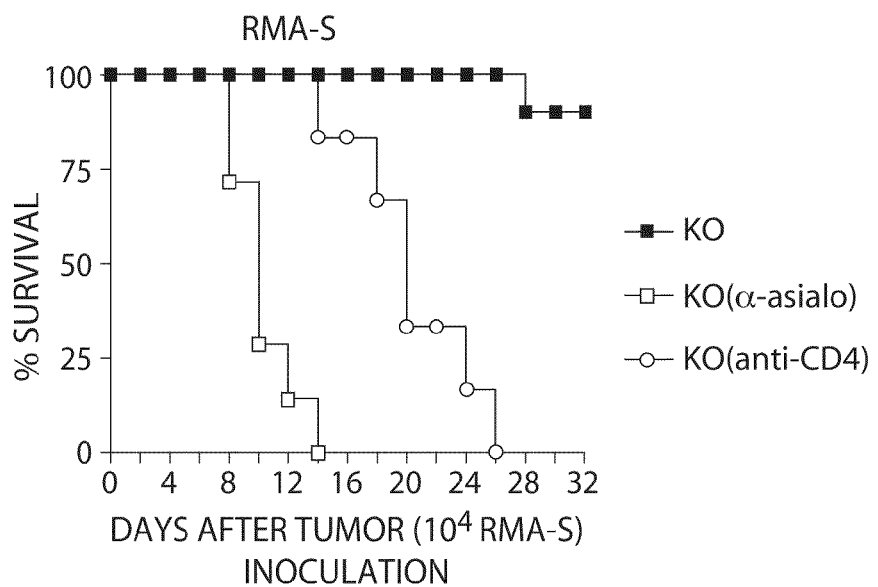

Previous studies have shown that NK cells control RMA-S growth in vivo in wt mice (Smyth et al., 1998). To further investigate the involvement of NK cells in the control of RMA-S tumor growth in CD69$^{-/-}$ mice, animals were depleted of NK cells prior to tumor induction by treatment with an anti-Asialo-GM1 serum. Injection with either control carrier or anti-Asialo-GM1 was initiated on day-1 before tumor challenge and was continued on days +2 and +4 after tumor inoculation. As expected, tumor growth was observed in all NK cell-depleted mice, but in none of the control mice (FIG. 9D). Anti-asialo GM1-treated CD69$^{-/-}$ mice developed tumors within the first 10 days after tumor inoculation, which is comparable to the earliest RMA-S tumor development observed in perforin-deficient C57BL/6 mice (Smyth and Johnstone, 2000; Smyth et al., 1998). The depletion of CD4$^+$ lymphocytes in CD69$^{-/-}$ mice increased tumor development but to a lesser extent than NK cell depletion (FIG. 9D). These results indicate that although NK cells are critically involved in RMA-S tumor rejection in CD69$^{-/-}$ mice, T cells also play a role in this process. In agreement with the relevance of T cells in tumor suppression in CD69$^{-/-}$ mice, an increased control of RMA overgrowth was observed in CD69$^{-/-}$ mice after three days of tumor inoculation (data not shown).

Figure 9E:
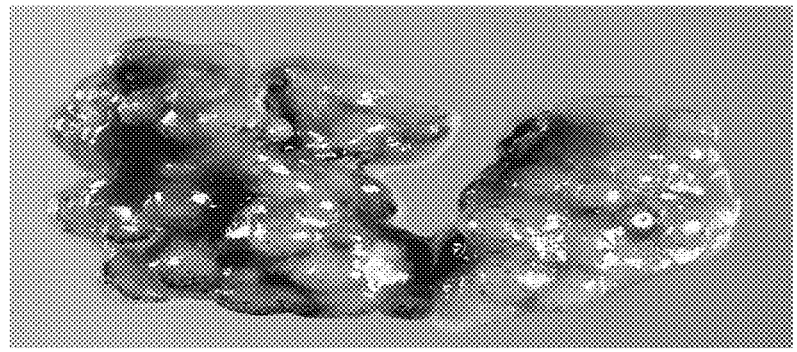
Figure 9E:
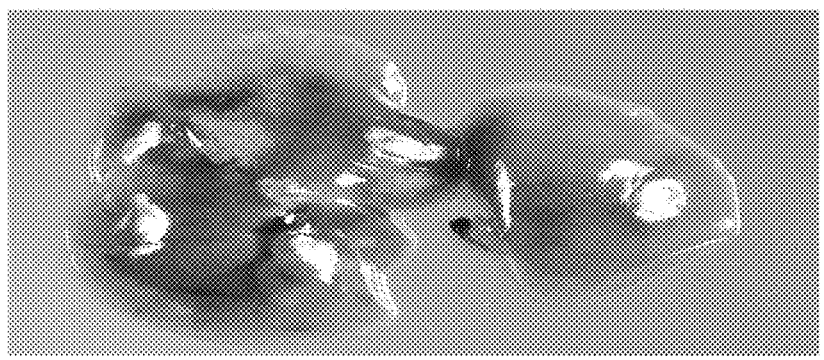
Figure 9E:
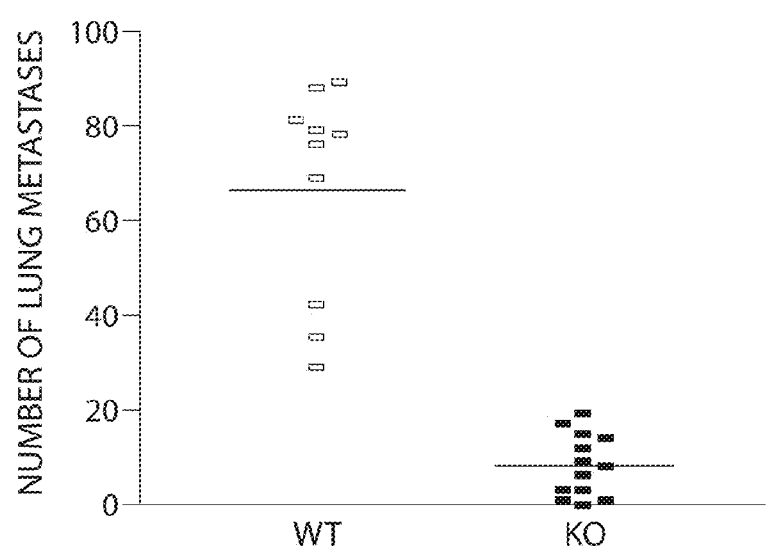

The increased anti-tumor activity of CD69$^{-/-}$ mice was not restricted to RMA-S cells, as it was also observed after challenge with C57BL/6 syngeneic RM-1 Class I$^-$ CD69$^-$ prostate carcinoma cells. There were significantly decreased numbers of lung metastases in CD69$^{-/-}$ mice compared to wt mice when challenged i.v. with RM-1 ($10^4$) cells. There was high number of pulmonary metastases in wt mice while CD69$^{-/-}$ mice remained almost free of metastasis (FIG. 9E).

Example 8

Increased Anti-Tumor Response in CD69$^{-/-}$ RAG-Deficient Mice

Figure 10A:
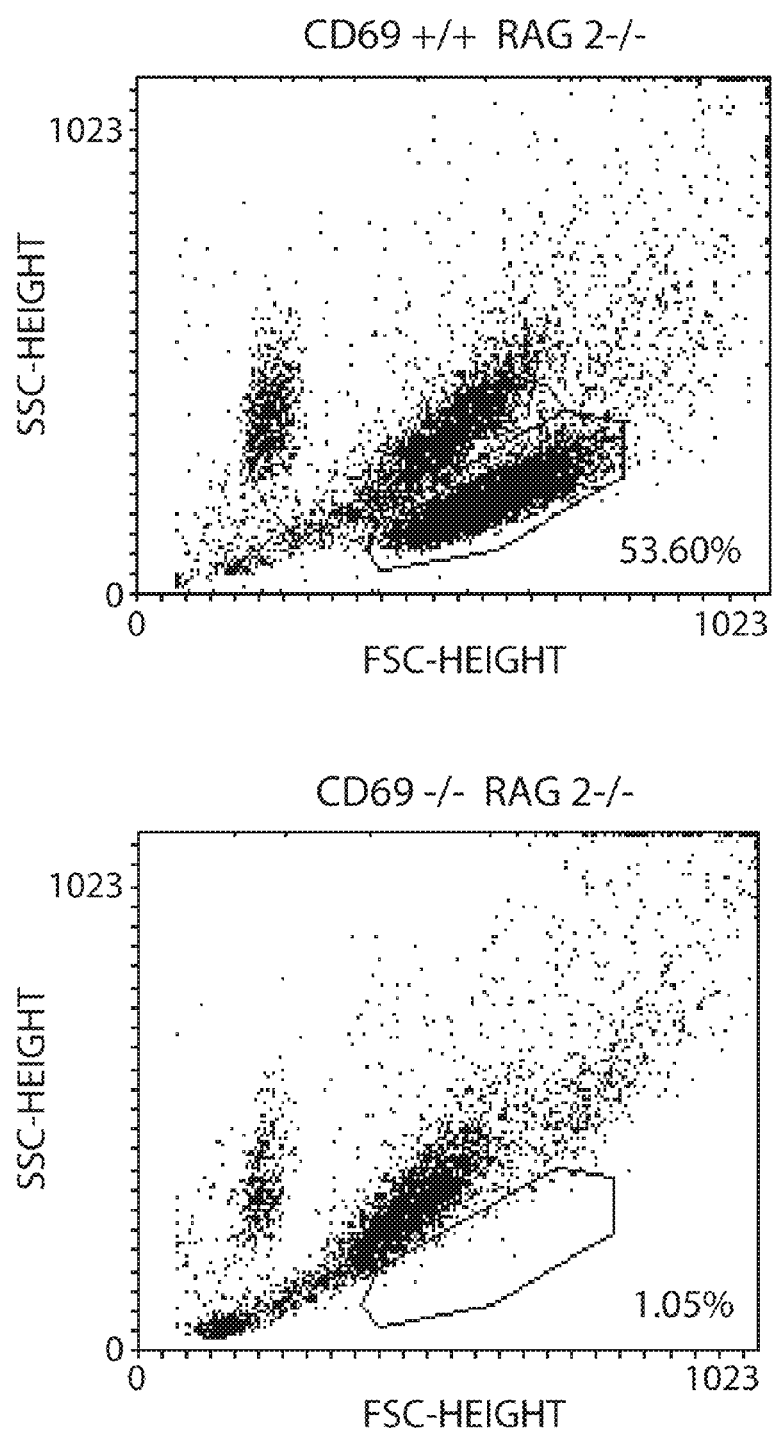
FIG. 10. Exacerbated anti-tumor response in CD69$^{-/-}$ RAG-deficient mice. Mice were injected intraperitoneally with 106 RMA-S tumor cells. Total unfractionated peritoneal cells (A, B) from CD69$^{+/+}$- and CD69$^{-/-}$-RAG2$^{-/-}$ mice were examined 72 h after tumor inoculation. (A) Forward and scattered FACS analysis. One representative mouse out of 10 per group is shown. (B) Profiles comparison by Coulter Multisizer cell counter. Results shown are representative of two independent experiments (n=8).
Figure 10B:
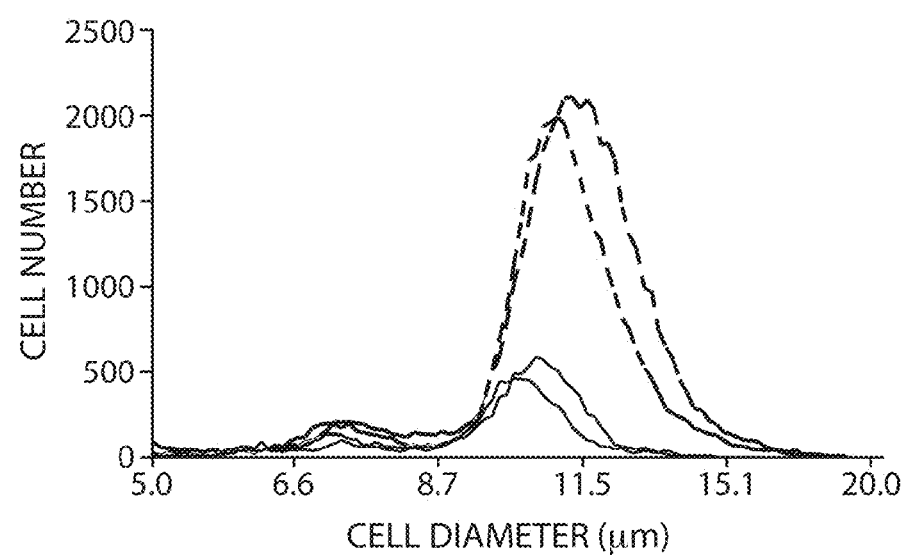

To analyze the contribution of innate immunity to the enhanced anti-tumor response observed in CD69$^{-/-}$ mice, CD69$^{-/-}$RAG-deficient mice and CD69+/+RAG-deficient mice were injected i.p. with RMA-S cells and tumor progression was analyzed (FIG. 10). Tumor cells overgrew in all wild-type RAG-deficient mice in response to $10^6$ RMA-S cells, whereas CD69$^{-/-}$RAG-deficient mice almost completely controlled tumor cell growth (FIG. 10A, B).

Example 9

Enhanced Immune Response in CD69$^{-/-}$ Mice

Figure 11A:
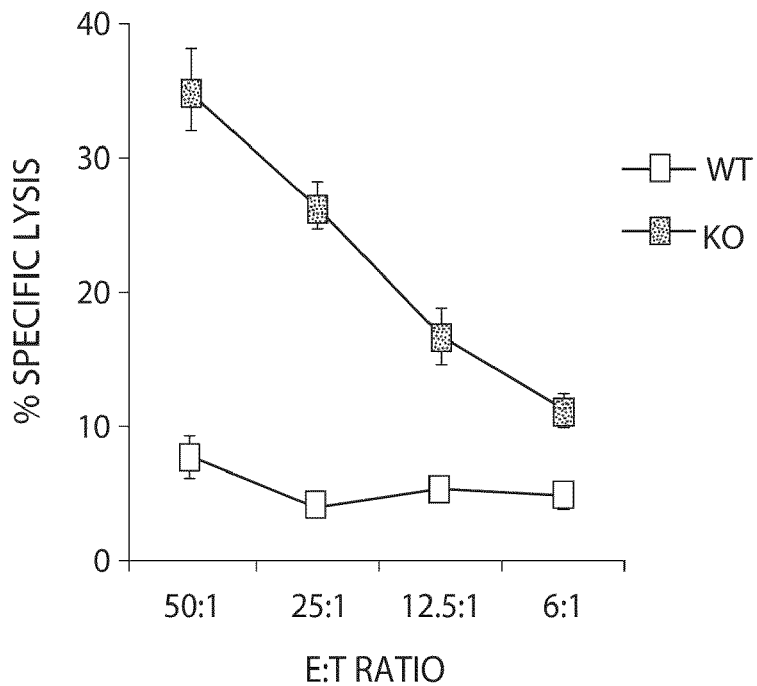
FIG. 11. Increased cytotoxicity and lymphocyte recruitment in CD69$^{-/-}$ mice. Mice received $10^4$ RMA-S cells (A) or RM-1(B) intraperitoneally. 72 h after tumor inoculation, total unfractionated peritoneal cells (A, B) from CD69$^{-/-}$ and wt mice were analyzed for cytotoxicity against YAC target cells. Two animals were used per experimental group (mean±SE). The results are representative of three experiments identically performed. Different symbols represent NK cells purified from different mice: Open symbols (wt) and solid symbols (CD69$^{-/-}$). (C, D, E) Peritoneal and splenic accumulation of lymphocytes in CD69$^{-/-}$ mice in response tumor cells. Mice were injected intraperitoneally with PBS or with $10^5$ RM-1 cells (n=7, mice/group). Peritoneal lavage was collected 3d and 6d later, and total leukocyte numbers (×$10^{-6}$) were determined (C). Cells collected from the lavage were analyzed with a Coulter Multisizer cell counter and profiles were compared at the indicated times after tumor inoculation (D). Data are representative from three independent experiments with 2/2, 2/2 and 4/4, wt (dotted lines)/CD69$^{-/-}$ (solid lines) mice. Increased spleens removed from 8 weeks old CD69$^{-/-}$ and wt mice after 3 days of i.p. $10^5$ RM-1 challenge were compared (E). Spleens shown are representative from several independent experiments.
Figure 11B:
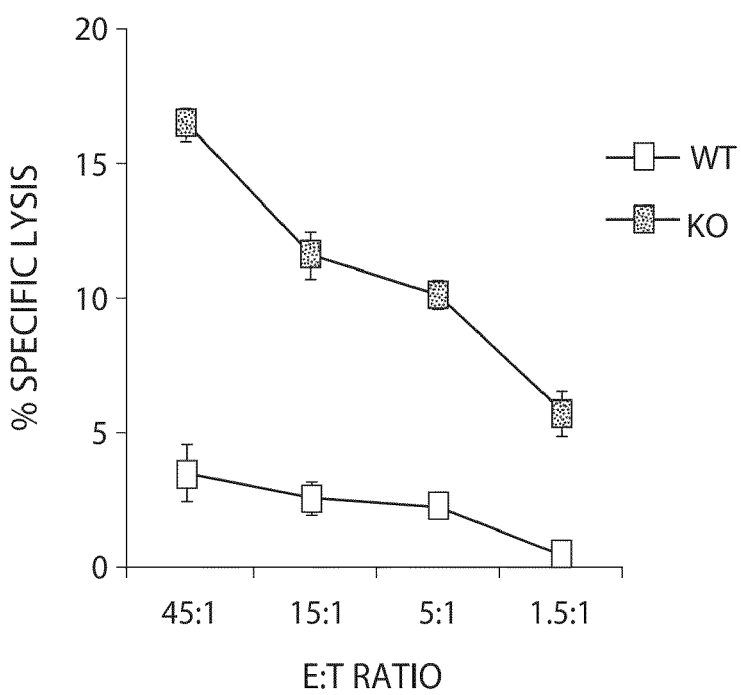
Figure 11C:
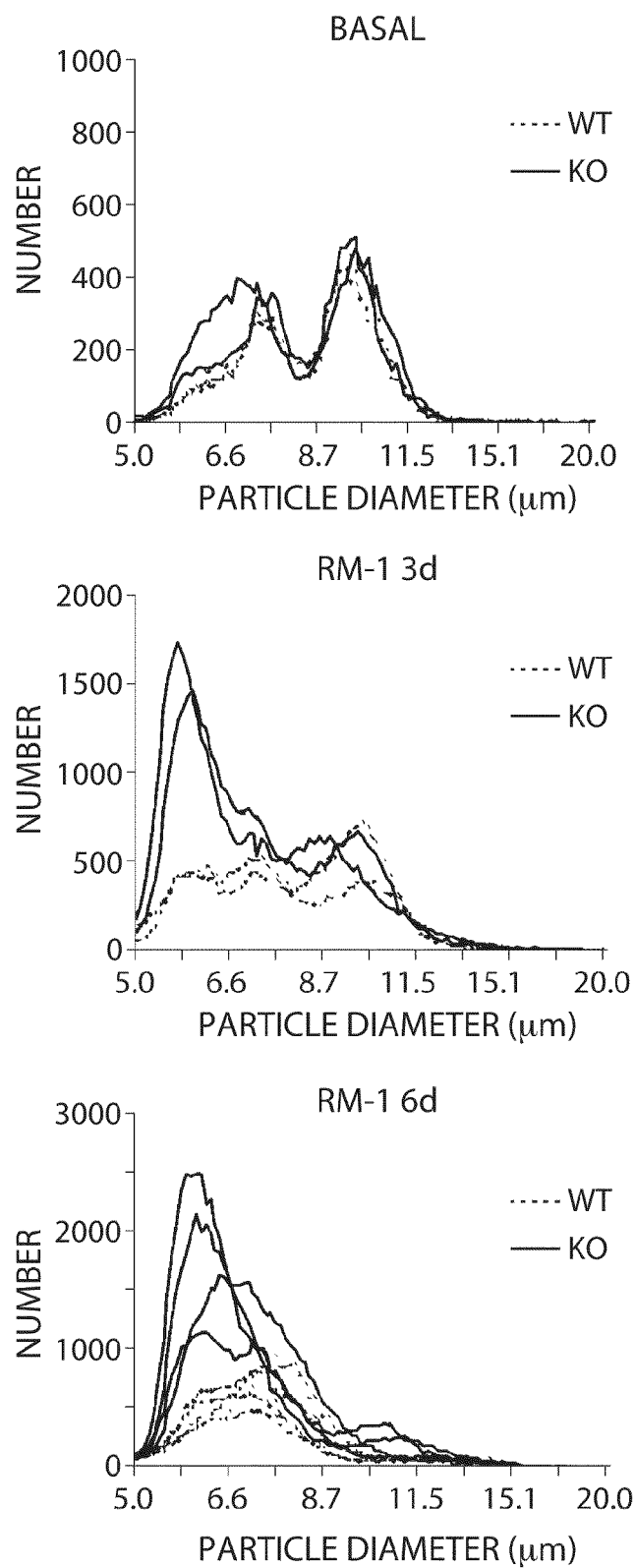
Figure 11D:
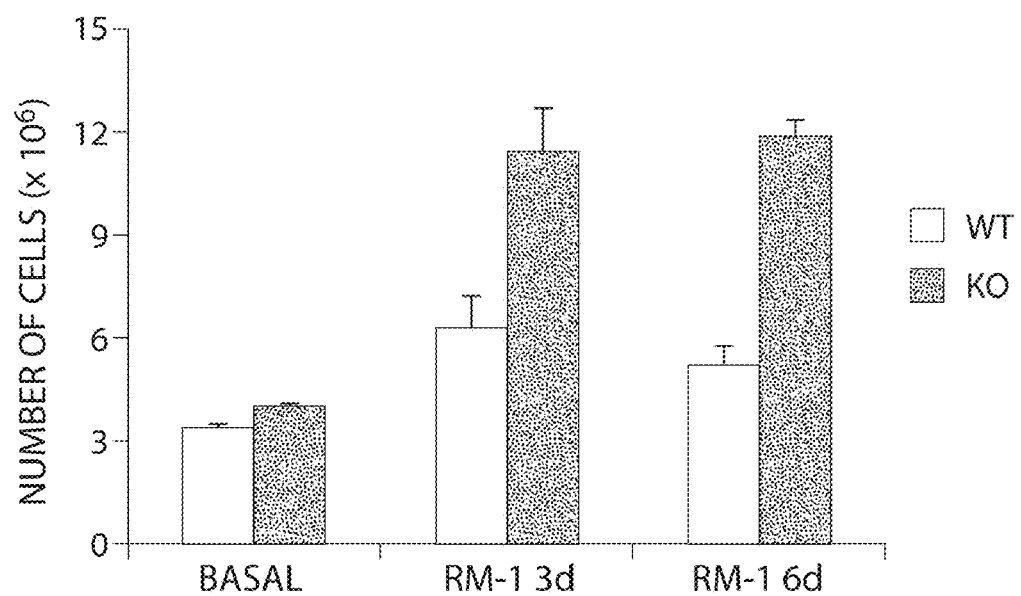
Figure 11E:
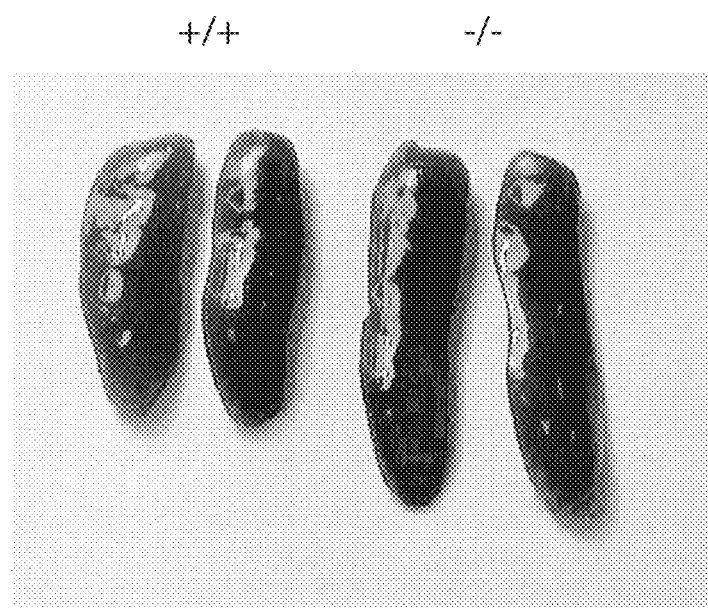

To assess whether tumor rejection was associated with an increased NK cell function, the lytic activity of peritoneal cells of RMA-S primed CD69$^{-/-}$ and wt mice was determined based on their capability to lyse NK-susceptible YAC-1 tumor cells in vitro. Freshly isolated unfractionated peritoneal cells from RMA-S inoculated (day 3) CD69$^{-/-}$ mice, were more efficient in killing YAC-1, than those derived from wt mice (FIG. 11A), thus showing a correlation between the in vivo NK immune response and in vitro NK cytotoxicity in CD69$^{-/-}$ mice. The increased tumor-induced NK cytolytic activity of CD69$^{-/-}$ mice was also observed after challenge with RM-1 prostate carcinoma cells (FIG. 11B). T lymphocytes and total peritoneal cells were quantified in mice that were unchallenged or challenged with RM-1 or RMA-S cells. Peritoneal NK cells were defined as staining positive with antibodies DX5 and 2B4 by two-color flow cytometry. As shown in FIG. 11C and Table I, the total cellularity in unchallenged peritoneal lavage was moderately increased in CD69$^{-/-}$ mice compared to wt mice. This was likely due to an increase in the number and proportion of lymphocytes, specifically, NK cells and CD3$^+$ T lymphocytes (2 fold) (Table IA). Upon RM-1 tumor challenge the total number of cells recruited to the peritoneum in CD69$^{-/-}$ mice was significantly increased compared to wt mice (FIG. 11D, Table IA). This reflects an increase in lymphocyte recruitment; the number of NK cells and CD3$^+$ T lymphocytes was almost 3 fold higher in CD69-deficient mice compared to wt mice (FIG. 11, Table I). In contrast, the number of peritoneal CD5$^+$B220$^+$ B-1 and CD5+B220$^+$ B-2 lymphocytes was similar in CD69$^{-/-}$ and wt mice, both under basal conditions and follow up tumor challenge with RM-1 (data not shown). Only slight increases were detected in monocytes and granulocytes in the peritoneum of CD69$^{-/-}$ as compared to wt mice (FIG. 11A). Moreover, the decline in cell recruitment observed in wt mice on day 6 after tumor challenge was not observed in CD69$^{-/-}$ mice (FIG. 10C). These data reveal a correlation between the number of NK cells and CD3$^+$ T lymphocytes in the peritoneum of CD69$^{-/-}$ mice and the anti-tumor response. Thus, CD69 does appear to regulate the number of NK cells and CD3$^+$ T lymphocytes recruited to the site of tumor challenge.

The spleen is a lymphoid organ strongly influenced by peritoneal inflammation. Accordingly, at day 6 of tumor challenge spleens of CD69$^{-/-}$ mice were much enlarged as compared to wt mice (FIG. 11D). Splenic cell counts showed a similar trend, but flow cytometric analyses revealed similar proportions of B220$^+$, CD3$^+$ and DX5$^+$ splenic lymphocytes in CD69$^{-/-}$ and wt mice. These data combined, suggest a role for CD69 as a regulator of lymphocyte accumulation at sites of inflammation.

Example 10

Augmented Lymphocyte Survival in CD69$^{-/-}$ Mice

Figure 12A:
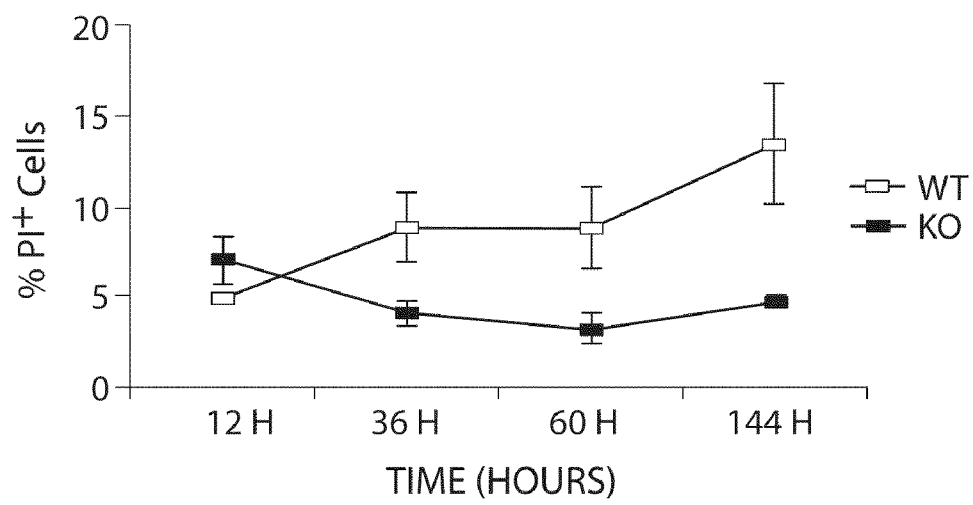
FIG. 12. Attenuation of spontaneous cell death of CD69$^{-/-}$ lymphocytes. Unfractionated peritoneal cells of untreated mice (A) were seeded in culture medium and cell survival was measured by PI staining. The values depict the percentage of PI$^+$ cells (mean±SD). Results are representative of three independent experiments. (B, C) Analysis of intracellular caspase-3 activity of spleen cells (B) and purified NK cells (C) from CD69+/+ (left) and CD69$^{-/-}$ (right) challenge mice (3 days with $10^5$ RM-1). Activation of Caspase-3 was detected by using fluorogenic substrate PhiPhiLux-GlD2. PhiPhiLux staining on FL-1 versus forward scatter channels was displayed. Data are representative of one experiment. (n=6).
Figure 12B:
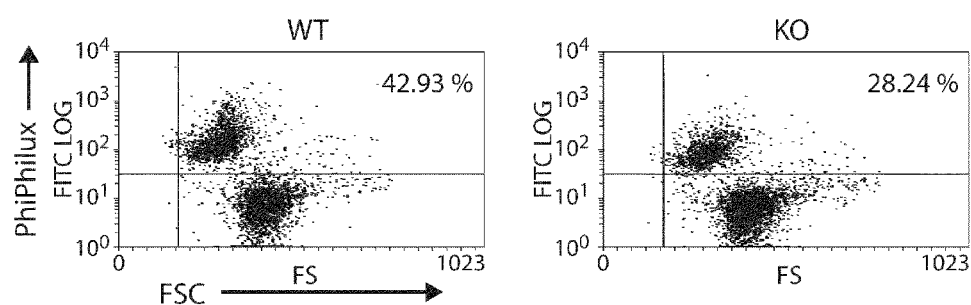
Figure 12C:
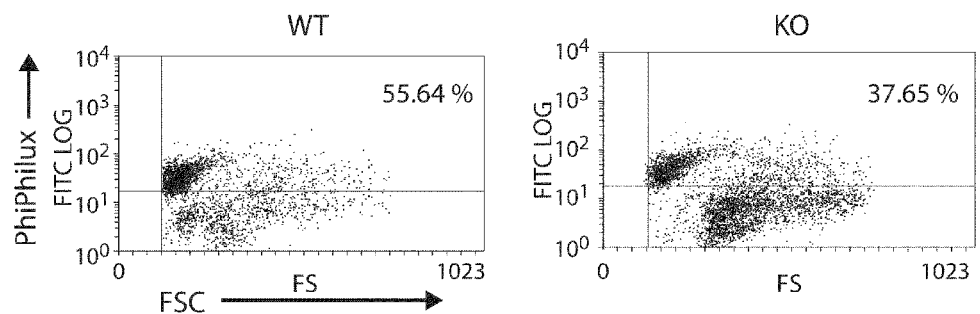

In the periphery, homeostatic mechanisms regulate the expansion and elimination of activated cells (Krammer, 2000). In order to investigate the mechanism of lymphocyte accumulation in spleen and peritoneum of CD69$^{-/-}$ mice, immune cell survival was analyzed in these mice. When peritoneal cell viability was studied in vitro, an increase in cell survival was detected in CD69$^{-/-}$ mice compared to wt mice (FIG. 12A). Although a 19% decrease in spontaneous apoptosis (24 h) of spleen lymphocytes from RM-1-challenged CD69$^{-/-}$ (23.36±1.73%, n=9) compared to wt mice (28.89±1.18%, n=9) were detected as reduced DNA-content by cell cycle analyses, this difference was significant (p<0.02). In addition, a significant decrease in spontaneous apoptosis (48 h) of spleen lymphocytes from RM-1-challenged CD69$^{-/-}$ (25.46±0.5%, n=6) compared to wt mice (44.56±1.3%, n=6) was measured by Caspase-3 activation analysis (FIG. 12B), this difference was significant (p<0.0001). Likewise, a significant decrease in spontaneous apoptosis (48 h) when Caspase-3 activation analyses were carried out with sorted DX5$^+$ CD3$^-$ NK splenocytes from RM-1-challenged CD69$^{-/-}$ (35.26±1.6%, n=4) compared to wt mice (45±1.8%, n=4) was measured by Caspase-3, this difference was significant (p<0.0001). Therefore, it appears that differences in lymphocyte survival may contribute to the elevated spleen size and cellularity observed in peritoneum of CD69$^{-/-}$ mice.

Example 11

Decreased TGF-β and Increased Pro-Inflammatory Factors in CD69$^{-/-}$ mice

Figure 13A:
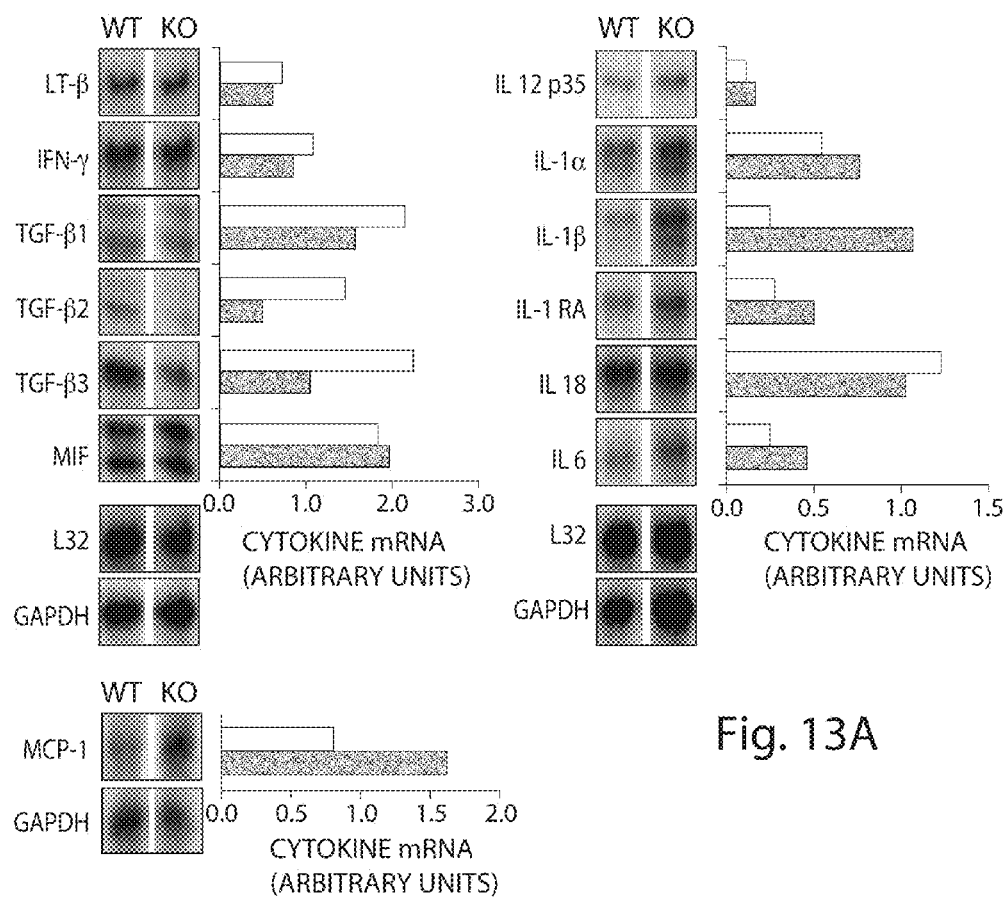
FIG. 13. Cytokine expression in CD69$^{-/-}$ mice. (A) Relative levels of cytokine and chemokine mRNA levels in peritoneal cells were analyzed after 3 days of $10^5$ RM-1 cells i.p. inoculation. Results are expressed in arbitrary densitometric units normalized for the expression of GAPDH or L32 in each sample. Five animals were used per experimental group and results are representative of four independent experiments. (B) MCP-1 levels in LPS-activated peritoneal cells from thioglycollated-treated CD69$^{-/-}$ and wt mice. Data represent the mean±SE (n=4 for each group) of one experiment representative of three independent experiments. *, P<0.004
Figure 13B:
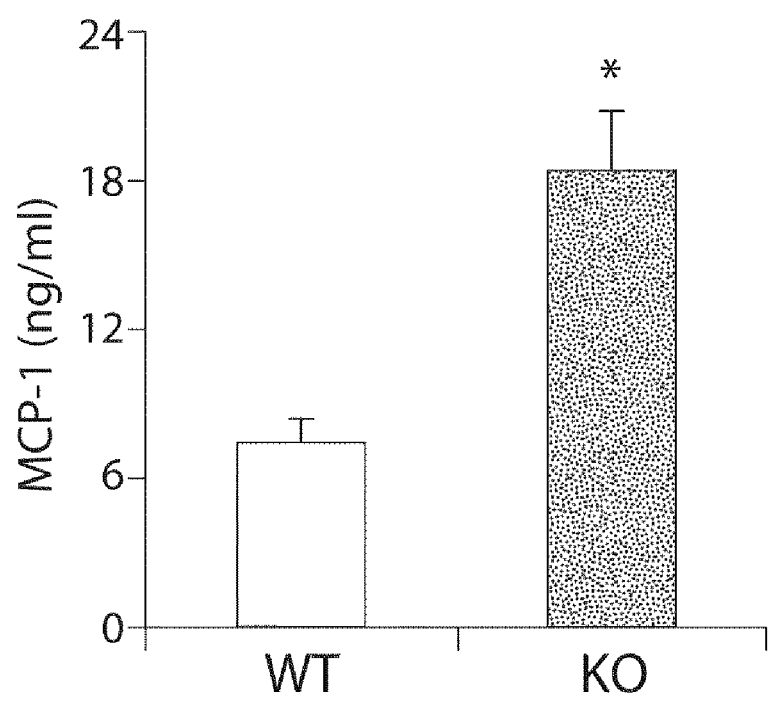

The anti-tumor response is orchestrated by a wide array of growth factors and cytokines, and altered expression of these factors may have a major impact on immune responses. Therefore, it was analyzed whether the enhanced anti-tumor response of CD69$^{-/-}$ as compared to wt mice is influenced by differences in cytokine and chemokine profiles. Assessment of relative levels of cytokine mRNA was performed by RNase Protection Assay. Analysis of peritoneal cell RNA of RM-1 challenged CD69$^{-/-}$ as compared to wt mice showed a change in TGF-β production. CD69$^{-/-}$ peritoneal cells produced less TGF-β1, -β2 and -β3 transcripts than wt peritoneal cells (FIG. 13). The decrease in mRNA levels observed in four separate experiments ranged from 33±5% for TGF-β1 levels to 74±19% for TGF-β3. The decrease in TGF-β2 RNA was sex dependent, varying from 20% for males to 110% for females. Analysis of peritoneal cells of RM-1 primed CD69$^{-/-}$ mice revealed an increase in cytokines IL-12p35 (32-68%), IL-1α (27-64%), IL-β1 (32% for males to 294% for females) and chemokine MCP-1α (133%) as compared to wt mice (FIG. 13). However, no significant changes in LT-P, IFNγ, MIF, IL-1-Rα, IL-18, Eotaxin, MIP-1α, MIP-1β, IP-10, MIP-1α, MIP-1β and Eotaxin were found (FIG. 13, and data not shown). Thus, these results suggest that the immune cells from CD69$^{-/-}$ mice have an abnormal pattern of cytokine expression, with defective synthesis of immunosuppressive factors and increased production of pro-inflammatory cytokines and chemokine MCP-1α. To further examine MCP-1 production, the ability of LPS activated peritoneal cells from thioglycolate treated mice was tested to produce MCP-1. As shown in FIG. 13B, the levels of MCP-1 produced by peritoneal cells from CD69$^{-/-}$ mice were almost three times higher than the levels made by wt mice. These changes in cytokines and chemokines observed in CD69$^{-/-}$ mice may account for the more potent immune response and T and NK lymphocyte enrichment observed in CD69$^{-/-}$ as compared to wt mice.

Example 12

Effect of Blocking TGF-β in Anti-Tumor Response in wt Mice

Figure 14:
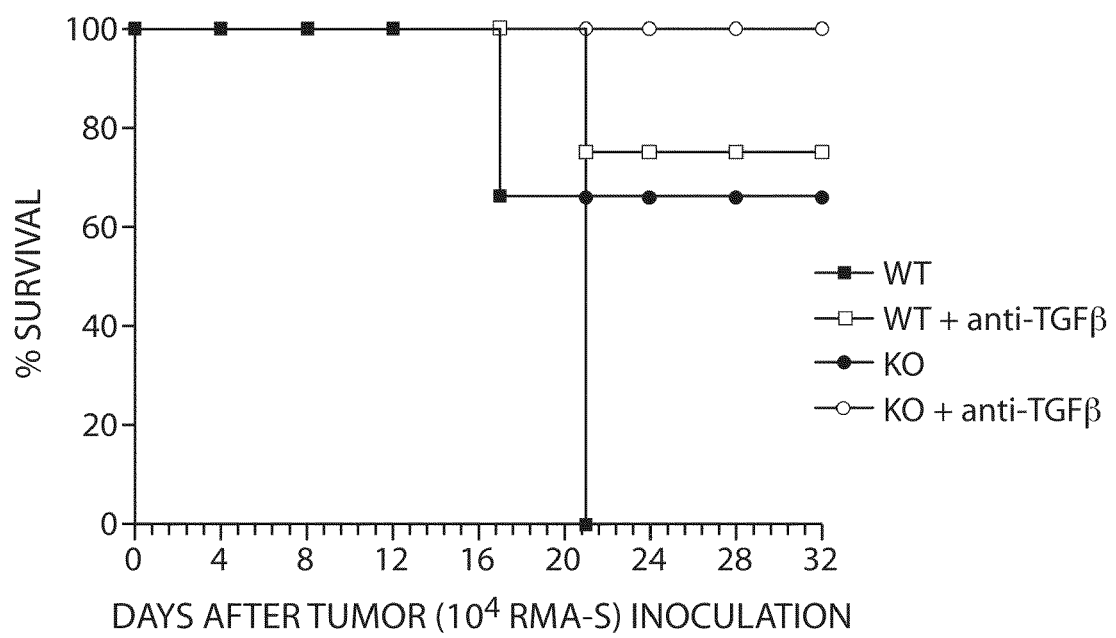
FIG. 14. Enhanced anti-tumor activity by blocking anti-TGF-β in wt mice. Survival plot of wt and CD69$^{-/-}$ mice i.p. injected on day 0 with $10^4$ RMA-S cells and treated with either 1D11 anti-TGF-β mAb (500 μg/injection) or PBS on day −3, −1 (before tumor challenge), and at days +1 and every week after tumor inoculation. (n=4). Results shown are representative of two independent experiments.

To examine whether TGF-β diminution may account for the increased anti-tumor response observed in CD69$^{-/-}$ mice, wt mice were treated with a blocking anti-TGF-β mAb. TGF-β blockade prevented tumor development, compared to control antibody or carrier (FIG. 14). These results indicate that TGF-β blockade in tumor challenged mice results in a similar phenotype to that seen in CD69-deficient mice.

Example 13

CD69 Upregulates TGF-β Secretion

Figure 15A:
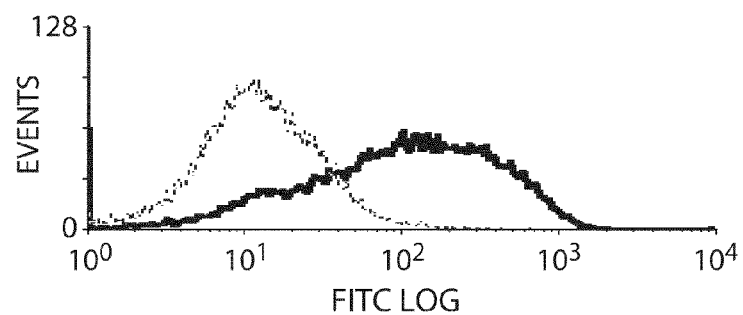
FIG. 15. CD69 engagement induces TGF-β1. Purified resting CD3$^+$ T cells were added to 96-well plates coated with anti-CD3. A) Expression of CD69 after activation with anti-CD3 were analyzed by staining with FITC-anti-murine CD69 mAb (solid line) after 24 h of culture. Dotted line represent negative control. B) Antibody engagement of CD69 induces TGF-β1 secretion in mouse T lymphocytes. Anti-CD69 (CD69.2.2) or the isotypic control (murine IgG1) was added followed by goat anti-mouse IgG antibody. Inhibition by PD98059 of CD69-induced TGF-β secretion. Cells were incubated in serum-free medium for 72 h and TGF-β1 was determined by ELISA. Data are expressed as mean±SD of replicate wells and are representative of three independent experiments. C) Cultured cells were removed and trypan blue was added. Dead cells (trypan blue positive) were determined after 48 h of culture. Data represent means of triplicate wells (bars±SD). (D) CD69 engagement induces Erk-1 and Erk-2 activation in anti-CD3 stimulated T lymphocytes. Preactivated T cells were coated on ice with anti-CD69 or isotype control mAb and lysed 5, 10, 15, 25 and 60 min after addition of warm (37° C.) goat anti-mouse antibody. Cell lysates were blotted with polyclonal anti-phospho Erk 1/2 (upper) antibody, then with anti-Erk mAb (lower) to confirm equal protein loading. The position of Erk1 and Erk2 is marked by arrows. Relative levels of Erk1 (upper right) and Erk2 (lower right) phosphorylation (phospho-Erk/total Erk, in arbitrary densitometric units) are shown. Control (□) and CD69$^{-/-}$ (■).
Figure 15B:
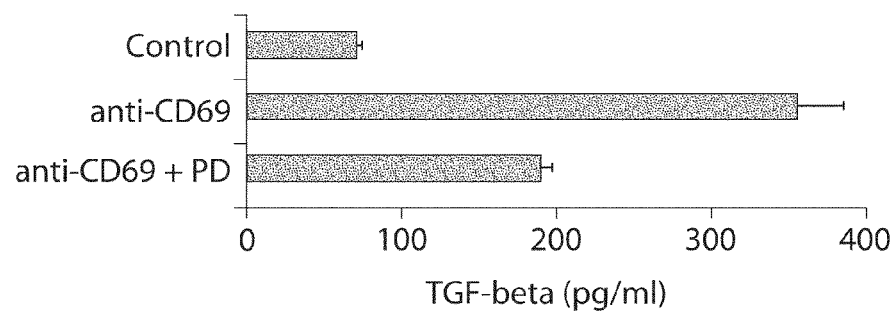
Figure 15C:
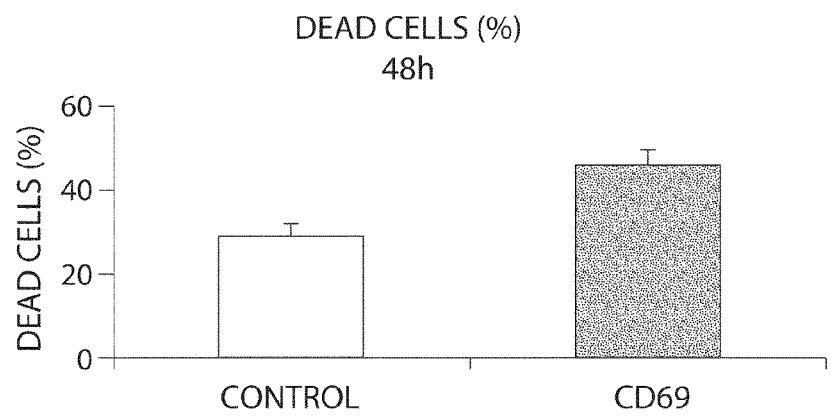

It was examined whether TGF-β is regulated by signaling through CD69 in T cells. Stimulation with anti-CD3 induced high expression of CD69 on purified spleen T cells of B6 mice (FIG. 15A). Engagement of CD69 on CD3 activated T cells markedly induced TGF-β production (FIG. 15B). This effect was not observed using a control isotype-matched antibody (FIG. 15B), indicating that antibody cross-linking of CD3 alone did not induce TGF-β, secretion as previously described (Chen et al., 2001). Quantification of viable and nonviable cells (FIG. 15C) at 48 h after cell culture, showed a reduction of lymphocyte survival, which correlates with enhanced TGF-β levels.

Figure 15D:
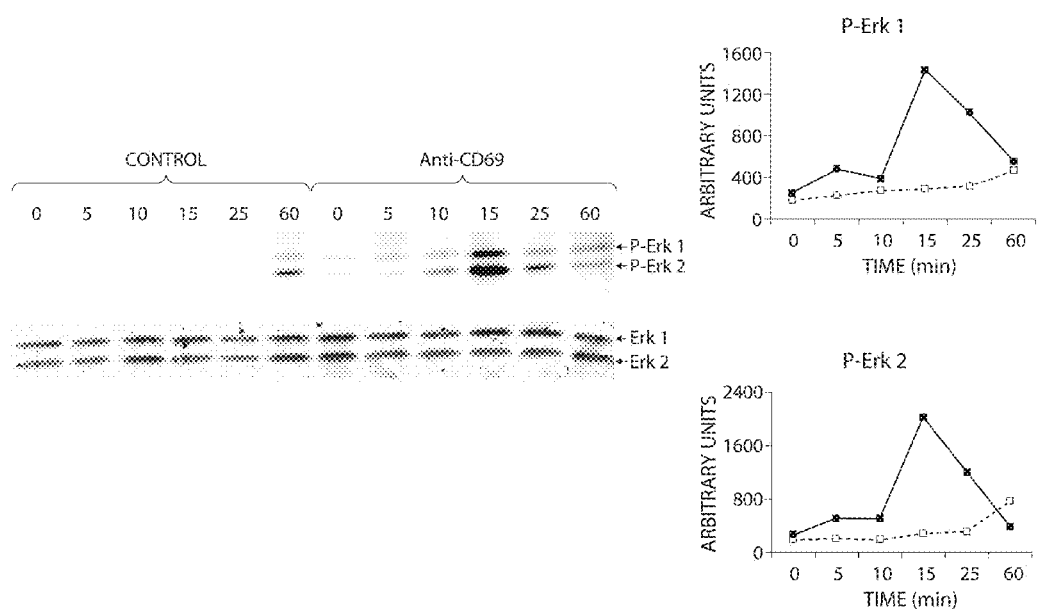

CD69 engagement on transfected mature cell lines induces phosphorylation of activating extracellular signal-regulated kinase (ERK) enzymes (Zingoni et al., 2000). To determine the transduction pathways activated by CD69 induction of TGF-β production, analysis of ERK activation was performed. CD69 engagement induces ERK-1 and ERK-2 activation in anti-CD3 stimulated T lymphocytes (FIG. 15D). ERK activation was already detected at 5-10 min, and the maximum was observed at 15 min. In addition, a significant reduction of CD69 induced TGF-β release was observed when ERK activation of T lymphocytes is inhibited by pretreatment with PD 098059 (FIG. 15B), indicating that ERK activation pathway is involved in CD69 induction of TGF-β production. These results establish a direct link between CD69 signaling and TGF-β production via ERK signal transduction and suggest a key role of CD69 on lymphocyte homeostasis.

Example 14

Anti-CD69 Abs Increase In Vivo Anti-Tumor Responses

Figure 16A:
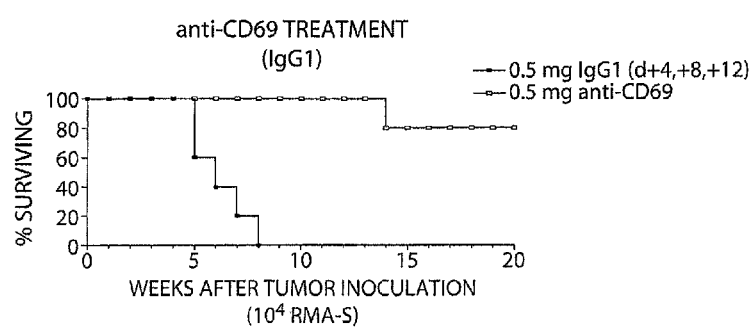
FIG. 16. Therapeutic anti-tumor activity of anti-CD69 mAbs in wt and RAG-deficient mice. Survival plot of wt and SCID mice treated with anti-CD69 mAbs or isotype control mAb. $10^4$ RMA-S tumor cells were injected intraperitoneally in wt mice (A, B) and $10^6$ RMA-S in SCID mice. (C) Mice were treated as indicated with anti-CD69 or isotype control mAbs (A, B, C) and observed daily for tumor growth up to 20 weeks by monitoring body weight and development of ascites. (A, n=9; B, n=6; C, n=9). Results shown are representative of two independent experiments.
Figure 16B:
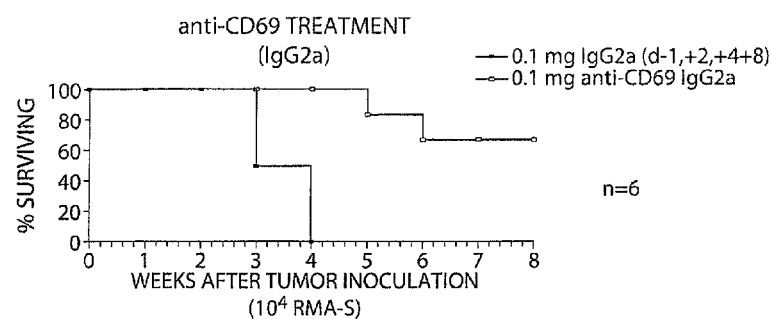
Figure 16C:
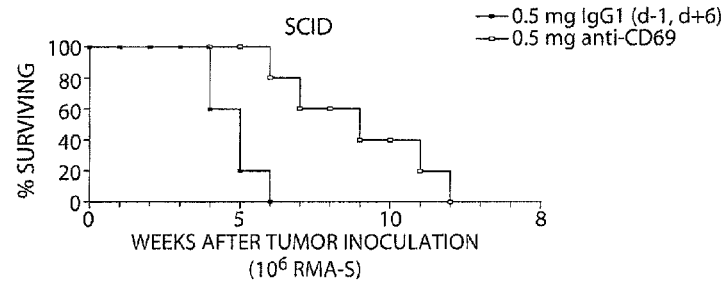

The murine mAbs were selected to examine the role of CD69 in mediating in vivo function in tumor therapy in RMA-S tumor bearing-mice. C57B6 mice receiving MHC class I—RMA-S syngeneic tumor cells (i.p.10$^5$) develop lethal tumors and 100% of the animals succumbed (FIG. 16A). When mice were treated several times with mAb anti-CD69 2.2 before and after tumor cell injection, 80% of the mice survived free of tumors (FIG. 16A); and the same inhibitory trend, although less potent, was observed after the administration of a single dose of the antibody treatment (FIG. 16 and data not shown). Also, the treatment of SCID mice with anti-CD69 2.2 inhibited the growth of RMA-S induced tumors. These results indicate that some of the mAb anti-tumor effects occur in the absence of T or B-lymphocytes.

In addition, anti-CD69 treated mice were able to kill RM-1 tumor cells and there were only a few detectable RM-1 metastases in the lung of anti-CD69 2.2 treated mice (1.25±0.9), while isotype control mice were unable to limit RM-1 lung metastasis and an average of 21.50±5.5 metastases were detected after 14 days of 10$^4$ i.v. injection of RM-1 cells.

Example 15

Anti-CD69 mAbs Affect Early Phase of Peritoneal Tumor Growth

Figure 17A:
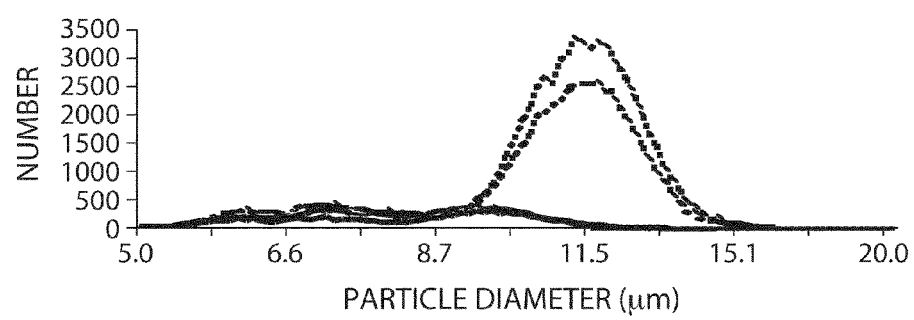
FIG. 17. Anti-CD69 Abs affect early phase of peritoneal tumor growth. Peritoneal cells of wt (A) or $RAG1^{-/-}$ (B) mice were examined at day 3 after i.p. injection of $10^6$ RMA-S tumor cells. Mice were treated one day before tumor inoculation with anti-CD69 (solid lines) or isotype control mAb (dotted lines) (500 μg per mouse). Cells collected from the lavage were analyzed with a Coulter Multisizer cell counter and profiles were compared. (n=8, mice/group). Data are representative from two independent experiments.
Figure 17B:
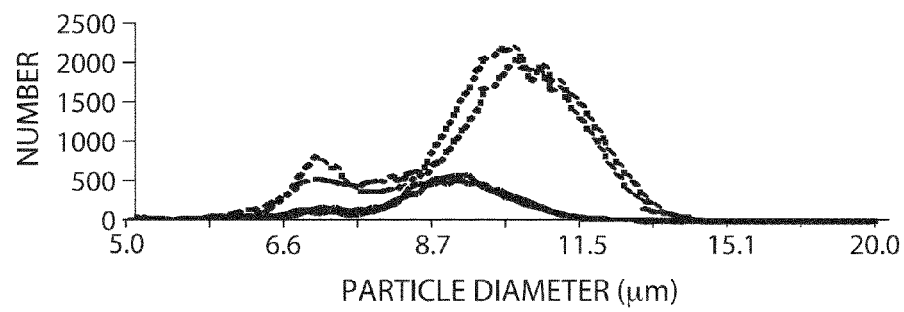
Figure 18A:
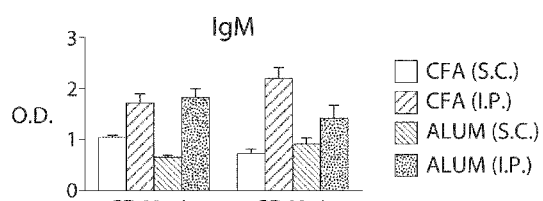
FIG. 18 depicts an antibody response to DNP-KLH in wildtype and CD69-deficient mice. The protocol followed for immunization was the injection of 100 μg of DNP-KLH per mice s.c. in the base of the tail or i.p., and using either Alum or CFA as adjuvants. Mice were bled at day 0 (not shown) and day 7 after the first injection (primary immunization). The second injection was administered at day 21, and mice were bled at day 28 (secondary immunization). a, levels of IgM in primary immunization (1:2000 serum dilution), expressed as arithmetic mean±s.d. of 4 mice/group/experiment were analyzed in two independent experiments. b, levels of IgM (1:2000 serum dilution), IgG1(1:20000), IgG2c (1:10000), IgG2b (1:10000), and IgG3 (1:10000) in secondary immunization, expressed as in (a). *, p<0.01 respect to the same treatment in WT mice (Mann-Whitney U test).
Figure 18B:
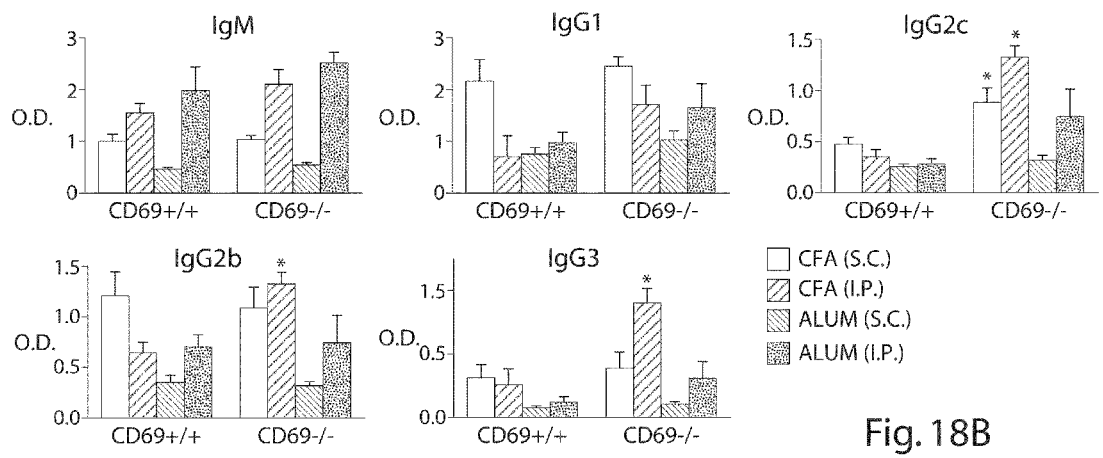

The in vivo effect of anti-CD69 mAb treatment on tumor growth was examined by ex vivo analysis of peritoneal cells after 3 days of i.p. inoculation with 2×10$^6$ RMA-S tumor cells. RMA-S cells, characterized by size-forward scattered FACS analysis, were not detected in the peritoneal cells analyses of anti-CD69 2.2 mAb-treated mice (3×10$^6$ recovered tumor cells), whereas peritoneal cell analyses of mice treated with control isotype mAb showed overgrowth of RMA-S cells (20×10$^6$ recovered tumor cells). Similar differences were observed in peritoneal cell analyses of anti-CD69 mAb treated RAG1$^{-/-}$ mice; only RMA-S cells are overgrown in control mAb treated mice but there were not detectable RMA-S cells in 75% of anti-CD69 treated mice (FIG. 17). Thus, anti-CD69-induced tumor cell elimination occurs during the early immune response and is effective in the absence of T and B-lymphocytes.

Example 16

Antibody Response to DNP-KLH in WT and CD69-Deficient Mice

In order to determine the effect of CD69 on antibody response, DNP-KLH has been injected into wildtype and CD69-deficient mice. Various different adjuvants (CFA or Alum) and different routes of immunization (i.p. or s.c. in the base of the tail) were tested. In addition, the protocol of DNP-KLH administration described in Lauzurica et al. (2000) *Blood* 95:2312-2320 was revised. The antigen dose was augmented to 100 µg/injection and the 2$^{nd}$ injection was at day 21, to allow adequate development of the germinal center reaction. The results of these experiments are shown in FIG. 19.

Figure 19:
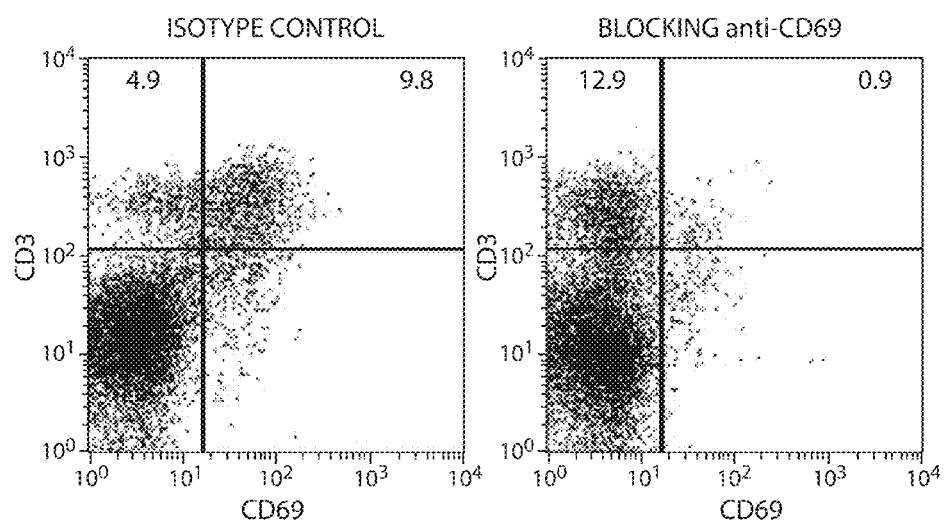
FIG. 19. anti-CD69 2.2 antibody down-regulates CD69 expression on thymocytes. Thymocytes from DBA/1 mice treated (right panel) or not (left panel) with 2.2 anti-mouse CD69 mAb were isolated and FACS stained with H1.2F3 anti-mouse CD69 FITC mAb and anti-mouse CD3 APC mAb. One representative experiment of five is shown.
Figure 20:
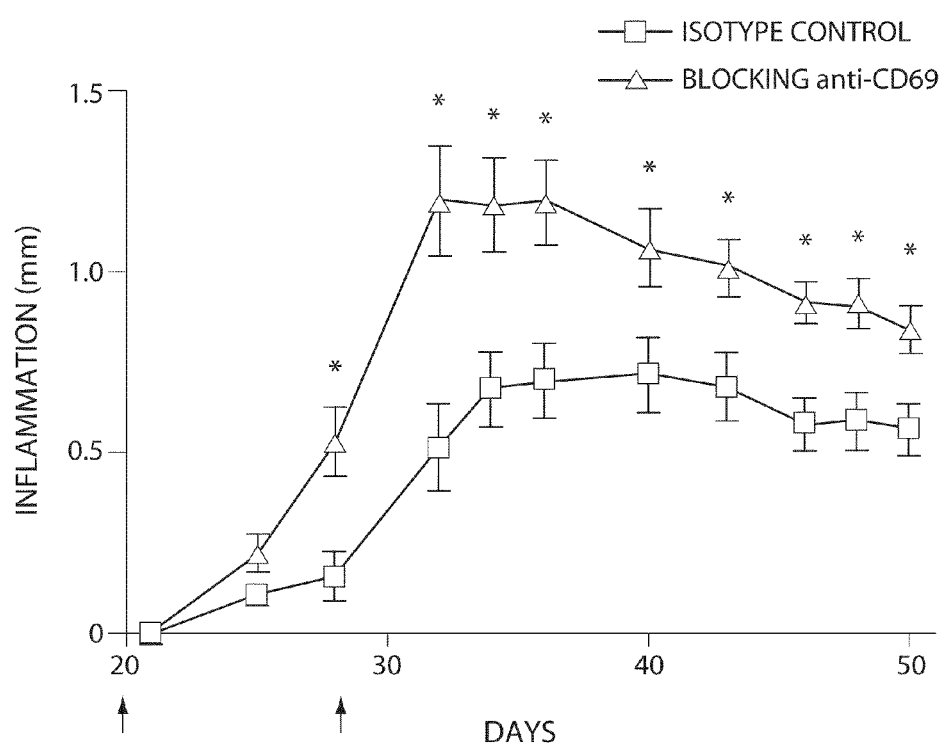
FIG. 20. Effect of treatment with 2.2 anti-CD69 mAb in CIA. DBA/1 mice were treated at days 20 and 28 with the blocking anti-CD69 mAb 2.2(▲), or the isotype control IgG1 mAb (■). Paw inflammation measured with a precision caliper is expressed as mm of inflammation relative to the day 21 value. Results are expressed as the arithmetic mean±s.d. of 12 mice per group in two independent experiments. *, P<0.01 versus control antibody (Mann-Whitney U test).
Figure 21:
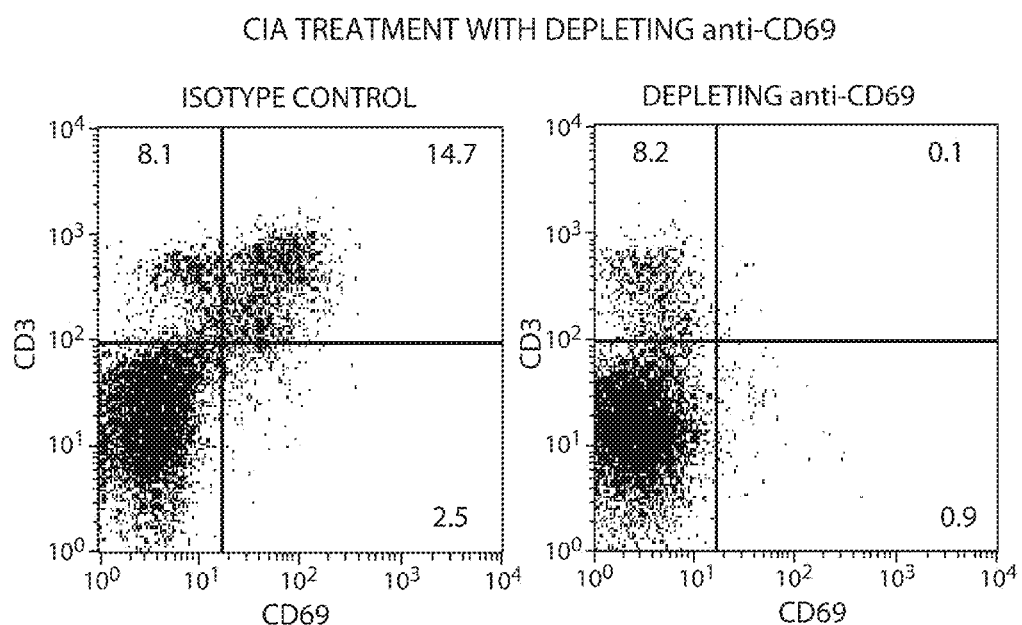
FIG. 21. anti-CD69 2.3 antibody depletes CD69 expressing-thymocytes. Thymocytes from DBA/1 mice treated (right panel) or not (left panel) with 2.3 anti-mouse CD69 mAb were isolated and FACS stained with H1.2F3 anti-mouse CD69 FITC mAb and anti-mouse CD3 APC mAb. One representative experiment of five is shown.

In the primary immunization with DNP-KLH, the higher levels of IgM response were obtained with i.p. administration of the Ag, but the higher difference (p=0.019) was obtained in the s.c. administration of CFA-DNP-KLH (FIG. 19). Therefore, no significant differences between wildtype and CD69-deficient mice were obtained for IgM. The level of IgG subtypes was low (measured at 1:2000 serum dilution), as it corresponds to the primary response and did not reveal significant changes between wildtype and CD69-deficient mice (not shown).

In the secondary immunization with DNP-KLH, i.p. administration was the most effective in the induction of IgM, without revealing significant differences (FIG. 19b). The IgG isotype levels were high (results shown at 1:10000-1:20000 serum dilution). The most relevant differences were found for IgG2c in response to CFA-DNP-KLH independently of the route of administration, although the i.p. administration was more effective (FIG. 19b). Also, IgG2b and IgG3 were augmented in response to i.p. CFA-DNP-KLH (FIG. 19b).

Regarding the adjuvant, significant differences were found only when CFA was used. These results suggest that an adjuvant that promotes Th1 responses, such as CFA, allows to detect the exacerbated Th1 response in the CD69-deficient mice easier than an adjuvant employed to enhance Th2 responses, as Alum.

Also, the route of administration shows different results, since the i.p. administration of DNP-KLH rendered more effective antibody responses than s.c. immunization.

In addition, the nature of the antigen can play difference in the immune response, since DNP-KLH is an external antigen, and type II collagen, promotes a reaction against an autoantigen. In conclusion, significant similarities have been found using this system and the secondary immunization with type II collagen, namely the finding of significant increases in C-II-specific IgG2c, IgG2b and IgG3 in CD69 deficient mice.

Material and Methods

Mice. Mice were bred at the Centro Nacional de Biotecnologia (Madrid, Spain) under SPF conditions, according to approved protocols. All experiments were performed using mice on C57BL/6 genetic background, excepted In vivo tumor challenge in $RAG2^{-/-}$ that was carried out in BALB/c genetic background. C57BL/6 and BALB/c wild type and gene targeted $CD69^{-/-}$ mice were 6 to 12 weeks of age at the time of experimentation, and littermate or age-matched litters whose parents were littermates were used as controls. $RAG1^{-/-}$ and $RAG2^{-/-}$ mice were purchased from Jackson Labs (Bar Harbor, Me.). For the generation of $RAG2^{-/-} \times CD69^{-/-}$ mice, the status of the RAG2 locus was followed by assaying blood for $CD3^+$ cells by FACS. Genotyping of the CD69 locus was performed by polymerase chain reaction as previously described (Lauzurica et al., 2000).

Induction and assessment of CIA. CFA was prepared by mixing 100 mg heat-killed *M. tuberculosis* (H37Ra; Difco, Detroit, Mich.) with 20 ml IFA (Sigma, St. Louis, Mo.). Chick CII (Sigma, 2 mg/ml) was dissolved overnight at 4° C. in 10 mM acetic acid and combined with an equal volume of CFA. Mice were injected i.d. at the base of the tail and boosted at day 21 as described (Campbell et al., 2000; Campbell et al., 2001). The same protocol was followed with DBA1 mice (Harlan, Madison, Wis.) using CFA with 1 mg/ml heat-killed *M. tuberculosis*. Control mice were treated with CFA without CII. Arthritis severity was monitored by direct examination with a digital caliper according to the following scale: grade 0, no swelling; 1, slight swelling and erythema; 2, pronounced inflammation; 3, joint rigidity. Each limb was graded, giving a maximum possible score of 12 per animal.

After sacrifice, paws were randomly collected, fixed, decalcified and paraffin embedded. Sections (5 µm) were stained with hematoxylin and eosin and scored as: no inflammation (0), slight thickening of synovial cell layer and/or some inflammatory cells in the sublining (1), thickening of synovial lining, infiltration of the sublining and localized cartilage erosions (2), and infiltration in the synovial space, pannus formation, cartilage destruction and bone erosion (3).

Blockade of TGF-β. The blocking anti-TGF-β 1D11.16.8 (mouse IgG1 hybridoma, purchased from ATCC, Manassas, Va.) (Dasch et al., 1989) at 2 mg/ml in 25 µl PBS, PBS only, or an irrelevant control isotype-matched mAb were injected s.c. in one of the paws every 2 days since the $2^{nd}$ injection of CII (21d), and paw inflammation monitored.

In Vivo blocking of active TGF-β in tumor challenge mice was performed by administration of 0.5 mg of mAb against TGF-β (1D11.16.8) on days −3, −1 and 1 relative to tumor inoculation and every week after tumor inoculation.

Cell proliferation assays. Draining LN and spleen cells ($2 \times 10^5$) in 200 µl RPMI medium (containing 50 µM 2-ME and 10% FCS) were cultured by triplicate in a 96-well plate at 37° C. (5% $CO_2$) for 72 h with 0-50 µg/ml of denatured CII (boiled for 10 min). Cells were pulsed with 1 µCi/well $^3$H-TdR (Amersham, Little Chanfont, England) the last 12 h of culture, before harvesting onto glass fiber filters for determination of $^3$H-TdR uptake.

Detection of anti-CII antibodies. ELISA for Ab to CII was performed as previously described (Campbell et al., 1998). HRP-conjugated secondary Ab specific for IgG1, IgG2a, IgG2b, IgG3, or IgM (Southern Biotechnology, Birmingham, Ala.) and IgA (Sigma) were used.

Cell isolation. Positive selection of splenocytes subsets was performed using specific biotin conjugated antibodies against CD11b, CD3, CD4, and CD8, all from BD-Pharmingen, and Biotin binder Dynabeads (Dynal A. S., Oslo, Norway) yielding about 98% cell purity. Mouse synovial cells were isolated from CIA WT mice as described for human synovial tissue (26), and further subset purification was performed as shown above. After positive selection of CD11b+ and CD3+ synovial cells, synovial cells were incubated with biotin CD45 and negatively selected using excess of avidin-magnetic beads. The remaining CD45 negative cells were used for RNA extraction. SF leukocytes were obtained from synovial effusions drained for the inflamed knees of the patients with reactive arthritis, ankylosing spondylitis, and RA who fulfilled the American College of Rheumatology 1987 criteria (27), and were purified by Ficoll-Hypaque (Pharmacia, Uppsala, Sweden) density gradient centrifugation.

RNase protection assay and quantitative real-time RT-PCR analyses. Joints were homogenized with a Polytron® (Kinematica, Littau, Switzerland) and total RNA was isolated using the Ultraspec RNA reagent (Biotecx, Houston, Tex.). In tumor challenge experiments total RNA was extracted from unfractionated peritoneal cells. RNase protection assays were performed on 2.5 to 5 µg of RNA using the Riboquant MultiProbe RNase Protection Assay System (PharMingen, San Diego, Calif.). For RT-PCR, 2 µg of DNaseI-treated RNA were reverse transcribed with MuLV RT (Roche Diagnostics Ltd, Lewes, UK). Real-time PCR was performed in a Lightcycler rapid thermal cycler system (Roche) using primers from different exons that generated products of about 200 bp length.

Anti-CD69 mAb. Murine mAb specific for mouse CD69 were generated by fusion of NS-1 myeloma cells with splenocytes from a CD69$^{-/-}$ mouse (Lauzurica et al., 2000) immunized with mouse pre-B cells expressing CD69. Antibodies specific for CD69 were purified and used at in vitro cytokine production assays.

In vivo treatment with anti-CD69. For in vivo treatment with anti-CD69 in CIA, 300 µg of 2.2 (IgG1) and 2.3 (IgG2a) mouse anti-mouse CD69 were injected i.p. as preventive (d. 20, and 28) or therapeutic (d. 32, and 40). As isotype control, 2.8 (IgG1) and 2.22 (IgG2a) were used. Paw inflammation was then monitored. For in vivo treatment with anti-CD69 in tumor challenged wt mice 500 µg of 2.2 (IgG1) mouse anti-mouse CD69 were injected i.p. (d. +4, +8 and +12) or 100 µg of 2.3 (IgG2a) mouse anti-mouse CD69 were injected i.p. (d. −1, +2, +4 and +8). SCID mice were injected i.p. with 500 µg of 2.2 (IgG1) mouse anti-mouse CD69 (d. −1 and +6). RAG1$^{-/-}$ mice were injected i.p. with 500 µg of 2.2 (IgG1) mouse anti-mouse CD69 at the day of tumor inoculation.

Determination of cytokine production in CIA. To determine the levels of cytokines in washouts of joint tissue, patellae with adjacent synovium were obtained at mice sacrifice (day 50) in a standardized manner from knee joints as previously described (Lubberts et al., 2000), and incubated in RPMI-1640 medium (200 µl/patella) with 0.1% BSA for 1 h at RT. Then, active and total TGF-β1 (Emax ImmunoAssay System; Promega Corp., Madison, Wis.), and IL-1β, TNF-α, and RANTES (OptEIA ELISA Sets; BD-Pharmingen) were quantified in culture supernatants. For in vitro cytokine production, mouse splenocytes (pre-stimulated with 5 µg/ml ConA; Sigma for 16 h, and then purified as described above) or synovial cells were incubated with an anti-mouse CD69, clone CD69.2.2 (mouse IgG1), or control mouse IgG1 mAb (both at 10 µg/ml) plus a goat anti-mouse IgG, Fc fragment specific (F(ab')$_2$, Jackson Immunoresearch, West Grove, Pa.) at 20 µg/ml. Then, active and total TGF-β1, IL-1β, TNF-α, and RANTES were assayed in culture supernatants after 24 h, as above. In addition, human synovial fluid leukocytes from patients with inflammatory joint diseases (RA, reactive arthritis, ankylosing spondylitis) were treated at 1×10$^6$ cells/ml with the anti-human CD69 TP1/8 or with an isotype control mAb, with or without cross-linking. TGF-β1 was assayed in culture supernatant after 24 h, as above.

TGF-β and MCP-1 production and ELISA in anti-tumor response. For in vitro TGF-β production, purified CD3$^+$ T cells from single cell suspensions of lymph nodes and spleen of C57BL/6 or BALB/c mice were obtained. For isolation of CD3$^+$ T lymphocytes, cells were incubated with anti-MAC-1 mAb, followed by two panning steps on petri dishes coated with a rabbit anti-mouse/rat IgG (DAKO, Denmark) at 4° C. The average purity of CD3$^+$ cells was >95%, as determined by flow cytometry analysis. T lymphocytes were stimulated (2×10$^6$ cells/ml) with plate-bound anti-CD3 mAb (1 µg/ml). Cells were added in 200 µl of serum-free Stem Span (Stem Cell Technologies Inc., Vancouver, BC) medium in flat-bottomed 96-well plates. Purified anti-CD69, clone CD69.2.2 (IgG1-κ), or control mouse IgG1 mAb were added at 20 µg/ml. For cross-linking, F(ab')$_2$ fragments of goat anti-mouse IgG F(ab')$_2$ Fc specific (Jackson ImmunoResearch Laboratories, Inc., West Grove, Pa.) were added at a final concentration of 20 µg/ml. PD98059 (Calbiochem, San Diego, Calif.) was added 1 h before addition of mAb and the final concentration of PD98059 was 20 µM. Cultures were incubated (37° C., 5% CO$_2$), supernatants were collected after 72 h, and secreted TGF-β assayed using a TGF-β1 Emax ImmunoAssay System (Promega Corp., Madison, Wis.) ELISA kit, according to the manufacturer's protocol. To measure MCP-1 production, 1 ml of thioglycollate solution (3% w/v; Sigma, St. Louis, Mo.) was injected i.p. into CD69$^{-/-}$ and wt mice. Mice were euthanized 3 days later, and leukocyte infiltrate was recovered by peritoneal lavage using 5 ml cold RPMI 1640 with 2% FCS. Peritoneal cells were added in 1 ml of complete medium in flat-bottomed 24-well plates and stimulated overnight with LPS (1 µg/ml) at 2×10$^6$ cells/ml. Culture supernatants were collected and MCP-1 was assayed using a mouse MCP-1 OptEIA ELISA Set (BD PharMingen).

Cell culture. The RM-1 prostate carcinoma (H-2$^b$) (a gift from Dr T. Thompson, Baylor College of Medicine, Houston, Tex.), YAC-1 (H-2$^a$), RMA (H-2$^b$) lymphoma cell lines and RMA-S(H-2$^b$) mutant lymphoma cells (derived from Rauscher virus-induced murine cell line RBL-5 and defective for peptide loading of MHC class I molecules) and 300.19 pre-B cells, were cultured in RPMI 1640 medium supplemented with 10% heat-inactivated fetal calf serum (FCS), 2 mm L-glutamine, 100 U/ml penicillin, and 100 µg/ml streptomycin (Gibco-Life Sciences, Gaithersburg, Md.) at 37° C., 5% CO$_2$.

Tumor control in vivo. Tumor cells (RMA, RMA-S or RM-1) in 0.2 ml of PBS were injected intraperitoneally or subcutaneously in untreated wt and CD69$^{-/-}$ mice, and in antibody depleted mice, as indicated. In experiments performed with NK cells-depleted mice, animals were injected i.p. with 100 µl rabbit anti-Asialo-GM-1 (Wako Chemicals, Richmond, Va.) 1 day before tumor inoculation and at days +2 and +4 after tumor challenge. Mice were treated for Lymphocyte T CD4+ depletion on day −1 (before tumor challenge), and at days+2, and +4 after tumor inoculation with either GK1.5 anti-CD4 or isotype control mAbs (100 µl/injection). Mice were observed by monitoring body weight daily for tumor ascites development for 12 weeks. Mice were killed, for ethical reasons, when the body weight had increased by 25%, corresponding to note obvious signs of irreversible tumor growth and the animals became moribund.

RM-1 lung colonization. RM-1 cells (1×10$^4$) suspended in 100 µl PBS were injected into the tail vein of CD69$^{-/-}$ and wt mice. Mice were euthanized 14 days later, the lungs removed and fixed in 4% paraformaldehyde solution and individual surface lung metastases were counted with the aid of dissecting microscope.

Flow Cytometry. Spleen and peritoneal exudate cells (1×10$^6$) were first preincubated with a blocking solution (PBS with 5% heat-inactivated fetal calf serum, 15% heat-inactivated rabbit serum, 0.02% sodium azide and 2.4G2 mAb) to avoid binding of Abs to Fcγ receptors. Cells were then stained for 30 min on ice with FITC- or PE-conjugated antibodies or with biotinylated antibodies followed by streptavidin-FITC or -PE (Southern Biotech, Birmingham, Al.) The following antibodies were used, anti-DX5 (DX5), -2B4 (2B4), -CD3 (145-2C11), -B220/CD45 (RA3-6B2), -CD4 (GK1.5), -CD8 (53.6.7), -CD5 (53-7.3), -CD11b (M1/70) and -CD69 (H1.2F3) (all from PharMingen, San Diego, Calif.). Finally, cells were washed and analyzed on FACS-Calibur flow cytometer (Becton Dickinson, Mountain View, Calif.), counting 10$^4$ live cells and using CellQuest software (Becton Dickinson). The number of cells migrating to the peritoneum was determined with a Coulter Multisizer II (Beckton Coulter, Fullertone, Ca).

IL-2 activated NK cells. Purified spleen NK cells were obtained using the CELLection Biotin Binder Kit (Dynal, Oslo, Norway) and biotinylated anti-DX5 antibody according to manufacturer's instructions. Briefly, viable single cell suspensions were incubated (1 h at 37° C.) on polystyrene tissue culture dishes (Becton Dickinson, Mountain View, Calif.). Nonadherent spleen cells were incubated (15 min, 4° C.) with biotinylated anti-DX5 antibody, washed twice, and CELLection biotin magnetic Dynabeads (1×10$^7$ magnetic beads per 1×10⁶ cells) added to capture antibody-coated cells. Cell purity was always >95% DX5⁺. NK cells were cultured in complete medium with 20% inactivated FCS, alone or with 1000 UI/ml human rIL-2 (72 h).

$^{51}$Cr-release assays. Direct NK cell cytotoxic activity was assessed by a standard $^{51}$Cr release assay. In all experiments, 5×10³ Na₂ $^{51}$CrO₄-labeled YAC-1 target cells were mixed with effector cells at the ratios indicated (4 h, 37° C.). Spontaneous $^{51}$Cr release was determined by incubating target cells with medium alone; maximum release was determined by adding Triton X100 at a final concentration of 2.5%. The percentage of specific lysis was calculated as % specific lysis=[(sample cpm−spontaneous cpm)/(maximal cpm−spontaneous cpm)]×100. Spontaneous $^{51}$Cr release was always <10%, and all experiments were performed in triplicate.

Cell death assays. Splenocytes (4×10⁶ cells/ml) from challenge mice (3 days with 10⁵ RM-1) were cultured in 24-well plates (Costar, Cambridge. MA) and cell death was assayed at 24 hours after the initiation of culture. Cell Cycle was monitored, cells were stained with propidium iodide (PI), and apoptosis was determined by flow cytometric analysis on an XL cytometer (Beckman Coulter, Fullertone, Calif.). Data are expressed as mean±SE (n=9). Caspase-3 activity was assayed at 48 hours after initiation of culture by incubation with the PhiPhiLux-G1D2 substrate solution (OncoImmunin, College Park, Md.) according to the manufacturer's protocol. Flow cytometric analysis was performed within 60 min of the end of the incubation period using an XL cytometer. Peritoneal cells (1×10⁶) from untreated mice were cultured in 24-well plates and cell death was assessed, at indicated time points, by PI staining. PI⁺-stained samples were considered apoptotic cells.

Western Blot Analysis. C57BL/6 T cells were preactivated with plate-bound anti-CD3 (5 μg/ml) in serum free medium (37° C., overnight). Cells were harvested, washed twice, and then rested for 4 h in serum free medium. Preactivated T cells were incubated in medium with anti-CD69 (IgG1) or control mouse IgG1 mAb (each at 10 μg/ml) for 30 min on ice. Cells were washed twice with cold medium and goat anti-mouse IgG F(ab')₂Fc specific (Jackson ImmunoResearch Laboratories, Inc., West Grove, Pa.) was added at 20 μg/ml in 37° C. medium. At the time indicated, the reaction was terminated by addition of ice-cold PBS, after which the cells were centrifuged. Pelleted cells were lysed in ice-cold lysis buffer (62.5 mM Tris-HCl, pH:6.8 at 25° C., 2% w/v SDS, 10% glycerol, 50 mM DTT, 0.01% w/v bromophenol blue) containing protease and phosphatase inhibitors. After centrifugation (13.000 g, 20 min), to remove insoluble cell fragments, cell lysate supernatant was separated on a 12% SDS-PAGE gel, transferred to Immun-Blot PVDF membrane (BioRad, Hercules, Calif.) and blotted with the indicated antibody. Polyclonal anti-phospho-Erk 1/2 antibody was from Calbiochem (San Diego, Calif.). The blot was stripped and reprobed with Erk kinase (Erk 1/2) monoclonal antibody (Zymed Lab. Inc. San Francisco, Calif.) to confirm equal protein loading. Western blotting was performed using anti-rabbit-HRP or anti-mouse-HRP and visualized by enhanced chemiluminesence.

Analysis of cell viability. T cells were cultured as for the TGF-β production assay; after 24 and 48 h culture, cell viability was determined by trypan blue addition.

Other Embodiments

From the foregoing detailed description of the specific embodiments of the invention, it should be apparent that unique methods of immune regulation based on the targeting of early activation molecules have been described. Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims. For instance, the choice of the particular type of tissue, or the particular effector to be translocated is believed to be a matter of routine for a person of ordinary skill in the art with knowledge of the embodiments described herein.

REFERENCES

Allavena, P., G. Bianchi, D. Zhou, J. van Damme, P. Jilek, S. Sozzani, and A. Mantovani. 1994. Induction of natural killer cell migration by monocyte chemotactic protein-1, -2 and -3. *Eur J Immunol.* 24:3233-6.

Allen, J. B., et al. 1990. Rapid onset synovial inflammation and hyperplasia induced by transforming growth factor-beta. J. Exp. Med. 171:231-247.

Arnett, F. C., et al. 1988. The American Rheumatoid Association 1987 revised criteria for the classification of rheumatoid arthritis. *Arthritis Rheum.* 31:315-324.

Border, W. A., and E. Ruoslahti. 1992. Transforming growth factor-beta in disease: the dark side of tissue repair. *J. Clin. Invest.* 90:1-7.

Bradford, M., 1976. A rapid and sensitive method for the quantification of microgram quantities of protein utilizing the principle of protein-dye binding. Anal. Biochem. 72, 248-254.

Brandes, M. E., et al. 1991. Transforming growth factor θ1 suppresses acute and chronic arthritis in experimental animals. *J. Clin. Invest.* 87:1108-1113.

Brüggemann, M. and Neuberger, M. S., 1996. Strategies for expressing human antibody repertoires in transgenic mice. Immunol. Today 17, 391-397.

Brüggemann, M. and Taussig, M. J., 1997. Production of human antibody repertoire in transgenic mice. Curr. Op. Biotechnol. 8, 455-458.

Butler, D. M., A. M. Malfait, L. J. Mason, P. J. Warden, G. Kollias, R. N. Maini, M. Feldmann, and F. M. Brennan. 1997. DBA/1 mice expressing the human TNF-alpha transgene develop a severe, erosive arthritis: characterization of the cytokine cascade and cellular composition. *J. Immunol.* 159:2867-76. Campbell, I. K., J. A. Hamilton, and I. P. Wicks. 2000. Collagen-induced arthritis in C57BL/6 (H-2$^b$) mice: new insights into an important disease model of rheumatoid arthritis. *Eur. J. Immunol.* 30:1568-1575. Campbell, I. K., K. O'Donnell, K. E. Lawlor, and I. P. Wicks. 2001. Severe inflammatory arthritis and lymphadenopathy in the absence of TNF. *J. Clin. Invest.* 107:1519-27. Campbell, I. K., M. J. Rich, R. J. Bischof, A. R. Dunn, D. Grail, and J. A. Hamilton. 1998. Protection from collagen-induced arthritis in granulocyte-macrophage colony-stimulating factor-deficient mice. *J. Immunol.* 1998:3639-3644.

Carr, M. W., S. J. Roth, E. Luther, S. S. Rose, and T. A. Springer. 1994. Monocyte chemoattractant protein 1 acts as a T-lymphocyte chemoattractant. *Proc Natl Acad Sci USA.* 91:3652-6.

Caspar-Bauguil, S., M. Saadawi, A. Negre-Salvayre, M. Thomsen, R. Salvayre, and H. Benoist. 1998. Mildly oxidized low-density lipoproteins suppress the proliferation of activated CD4+ T-lymphocytes and their interleukin 2 receptor expression in vitro. *Biochem. J.* 330:659-666.

Cazac, B. B., et al. 2000. TGF-beta receptor controls B cell responsiveness and induction of IgA in vivo. *Immunity* 13:443-451

Cebrian, M., E. Yague, M. Rincon, M. Lopez-Botet, M. O. de Landazuri, and F. Sanchez-Madrid. 1988. Triggering of T cell proliferation through AIM, an activation inducer molecule expressed on activated human lymphocytes. *J Exp Med.* 168:1621-37.

Chen, W., M. E. Frank, W. Jin, and S. M. Wahl. 2001. TGF-beta released by apoptotic T cells contributes to an immunosuppressive milieu. *Immunity.* 14:715-25.

Chen, W., et al. 1998. Engagement of cytotoxic T lymphocyte-associated antigen-4 (CTLA-4) induces transforming growth factor-beta production by murine CD+ T cells. *J. Exp. Med.* 188:1849

Chen, Y., V. K. Kuchroo, J. Inobe, D. A. Hafler, and H. L. Weiner. 1994. Regulatory T cell clones induced by oral tolerance: suppression of autoimmune encephalomyelitis. *Science.* 265:1237-1240.

Conde, M., Montano, R., Moreno-Aurioles, V. R., Ramirez, R., Sanchez-Mateos, P., Sanchez-Madrid, F., and Sobrino, F. 1996. Anti-CD69 antibodies enhance phorbol-dependent glucose metabolism and Ca2+ levels in human thymocytes. Antagonist effect of cyclosporin A. *J. Leukoc. Biol.*, 278-284.

Cosulich, M. E. 1987. Functional characterization of an antigen involved in an early step of T-cell activation. *Proc. Natl. Acad. Sci. USA* 84:4205-4209.

Coventry, B. J., S. C. Weeks, S. E. Heckford, P. J. Sykes, J. Bradley, and J. M. Skinner. 1996. Lack of IL-2 cytokine expression despite IL-2 messenger RNA transcription in tumor-infiltrating lymphocytes in primary human breast carcinoma: selective expression of early activation markers. *J. Immunol.* 156:3486-3492.

Crispín, J. C., Martinéz, A., Pablo, P. de, Velasquillo, C. and Alcocer-Varela, J., 1998. Participation of the CD69 antigen in the T-cell activation process of patients with systemic lupus erythematosus. Scand. J. Immunol. 48, 196-200.

Dasch, J. R., D. R. Pace, W. Waegell, D. Inenaga, and L. Ellingsworth. 1989. Monoclonal antibodies recognizing transforming growth factor-beta. Bioactivity neutralization and transforming growth factor beta 2 affinity purification. *J. Immunol.* 142:1536-41.

Dighe A S, R. E., Old L J, Schreiber R D. 1994. Enhanced in vivo growth and resistance to rejection of tumor cells expressing dominant negative IFN gamma receptors. *Immunity.* 1:447-456.

Erlanson, M., Grönlund, E., Löfvenberg, E., Roos, G. and Lindh, J., 1998. Expression of activation markers CD23 and CD69 in B-cell non-Hodgkin's lymphoma. Eur. J. Haematol. 60, 125-132.

Esplugues, E. et al. 2003. Enhanced antitumor immunity in mice deficient in CD69. *J. Exp. Med.* 197:1093-1106.

Falcone, M., and N. Sarvetnick. 1999. Cytokines that regulate autoimmune responses. *Curr. Opin. Immunol.* 11:670-676.

Fava, R., et al. 1989. Active and latent forms of transforming growth factor-beta activity in synovial effusions. *J. Exp. Med.* 169:291

Feldmann, M. 2002. Development of anti-TNF therapy for rheumatoid arthritis. *Nat. Rev. Immunol.* 2:364-371

Feldmann, M., F. M. Brennan, and R. N. Maini. 1996. Role of cytokines in rheumatoid arthritis. *Ann. Rev. Immunol.* 14:397-440.

Feng, C., et al. 2002. A potencial role for CD69 in thymocyte migration. Int. Immunol. 14:535-544

García-Monzón, C., R. Moreno-Otero, J. M. Pajares, A. García-Sanchez, M. López-Botet, M. O. de Landazuri, and F. Sánchez-Madrid. 1990. Expression of a novel activation antigen on intrahepatic CD8+ T lymphocytes in viral chronic active hepatitis. Gastroenterology. 98:1029-1035.

Gessl, A. and Waldhäusl, W., 1998. Increased CD69 and human leukocyte antigen-DR expression on T lymphocytes in insulin-dependent diabetes mellitus of long standing. J. Clin. Endocrinol. Metabol. 83, 2204-2209.

Gill P S, H. W. J., Kaplan M H, Ribeiro R C, Bennett J M, Liebman H A, Bernstein-Singer M, Espina B M, Cabral L, Allen S, Kornblau S, Pike M C, Levine A M. 1995. Treatment of adult T-cell leukemia-lymphoma with a combination of interferon alfa and zidovudine. *N Engl J Med.* 332::1744-1748.

Gorelik, L., and R. A. Flavell. 2000. Abrogation of TGFbeta signaling in T cells leads to spontaneous T cell differentiation and autoimmune disease. *Immunity.* 12:171-81.

Gorelik, L., and R. A. Flavell. 2001. Immune-mediated eradication of tumors through the blockade of transforming growth factor-β signaling in T cells. *Nat. Med.* 7:1118-1122.

Griffiths, M. M., et al. 1999. Mapping autoimmunity genes. *Curr. Opin. Immunol.* 11:689-700.

Gu, L., B. Rutledge, J. Fiorillo, C. Ernst, I. Grewal, R. Flavell, R. Gladue, and B. Rollins. 1997. In vivo properties of monocyte chemoattractant protein-1. *J Leukoc Biol.* 62:577-80.

Hallegua, D. S., et al. 2002. Potential therapeutic uses of interleukin 1 receptor antagonists in human diseases. *Ann. Rheum. Dis.* 61:960-967.

Hara, T., L. K. Jung, J. M. Bjorndahl, and S. M. Fu. 1986. Human T cell activation. III. Rapid induction of a phosphorylated 28 kD/32 kD disulfide-linked early activation antigen (EA 1) by 12-o-tetradecanoyl phorbol-13-acetate, mitogens, and antigens. *J. Exp. Med.* 164:1988-2005.

Hartnell, A., D. S. Robinson, A. B. Kay, and A. J. Wardlaw. 1993. CD69 is expressed by human eosinophils activated in vivo in asthma and in vitro by cytokines. *Immunology.* 80:281-286.

Harwood, S. J., Valdivia, S., Hung, G. L., Quenzer, R. W., 1999. Use of Sulesomab, a radiolabeled antibody fragment, to detect osteomyelitis in diabetic patients with foot ulcers by leukoscintigraphy. Clin. Infect. Dis. 6, 1200-1205.

Hernandez-García, C., et al. 1996. The CD69 activation pathway in rheumatoid arthritis synovial fluid T cells. *Arthritis Rheum.* 39:1277-1286.

Hojo, M., T. Morimoto, M. Maluccio, T. Asano, K. Morimoto, M. Lagman, T. Shimbo, and M. Suthanthiran. 1999. Cyclosporine induces cancer progression by a cell-autonomous mechanism. *Nature.* 397:530-534.

Iannone, F., Corrigal, V. M. and Panayi, G. S., 1996. CD69 on synovial T cells in rheumatoid arthritis correlates with disease activity. Br. J. Rheumatol. 39, 397.

Jakobovits, A., 1995. Production of fully human antibodies by transgenic mice. Curr. Op. Biotechnol. 6, 561-566.

Ji, H., et al. 2002. Critical roles for interleukin 1 and tumor necrosis factor alpha in antibody induced arthritis. *J. Exp. Med.* 196:77-85.

Kaplan D H, S. V., Dighe A S, Stockert E, Aguet M, Old L J, Schreiber R D. 1998. Demonstration of an interferon gamma-dependent tumor surveillance system in immunocompetent mice. *Proc Natl Acad Sci USA.* 95:7556-61.

Kehrl, J. H., L. M. Wakefield, A. B. Roberts, S. Jakowlew, M. Alvarez-Mon, R. Derynck, M. B. Spom, and A. S. Fauci. 1986. Production of transforming growth factor beta by human T lymphocytes and its potential role in the regulation of T cell growth. *J Exp Med.* 163:1037-50.

Kitamura, D., Roes, J., Kuhn, R., and Rajewsky, K. 1991. A B cell-deficient mouse by targeted disruption of the membrane exon of the immunoglobulin μ chain gene. Nature. 350, 423-426.

Klein et al. 2001 Gene Expression Profiling of B Cell Chronic Lymphocytic Leukemia Reveals a Homogeneous Phenotype Related to Memory B Cells. J. Exp. Med. 11:1625.

Klee, G. G., 2000. Human anti-mouse antibodies. Arch. Pathol. Lab. Med., 124, 921-923.

Köhler, G. and Milstein, C., 1975. Continuous cultures of fused cells secreting antibody of redefined specificity. Nature, 256, 495-497.

Krammer, P. H. 2000. CD95's deadly mission in the immune system. *Nature.* 407:789-95.

Kulkarni, A. B., et al. 1993. Transforming growth factor beta 1 null mutation in mice causes excessive inflammatory response and early death. *Proc. Natl. Acad. Sci. USA* 90:770-774.

Kuruvilla, A. P., R. Shah, G. M. Hochwald, H. D. Liggitt, M. A. Palladino, and G. J. Thorbecke. 1991. Protective effect of transforming growth factor β1 on experimental autoimmune disease in mice. *Proc. Natl. Acad. Sci. USA.* 88:2918-2921.

Laffon, A., R. García-Vicuna, A. Humbria, A. A. Postigo, A. L. Corbi, M. O. de Landazuri, and F. Sanchez-Madrid. 1991. Upregulated expression and function of VLA-4 fibronectin receptors on human activated T cells in rheumatoid arthritis. *J. Clin. Invest.* 88:546-52.

Lanier, L. L., Buck, D. W., Rhodes, L., Ding, A., Evans, E., Barney, C. and Phillips, J. H., 1988. Interleukin 2 activation of natural killer cells rapidly induces the expression and phosphorylation of the Leu-23 activation antigen. J. Exp. Med. 167, 1572-1585.

Lauzurica, P., D. Sancho, M. Torres, B. Albella, M. Marazuela, T. Merino, J. A. Bueren, A. C. Martinez, and F. Sanchez-Madrid. 2000. Phenotypic and functional characteristics of hematopoietic cell lineages in CD69-deficient mice. *Blood.* 95:2312-20.

Letterio, J. J., and A. B. Roberts. 1997. TGF-beta: a critical modulator of immune cell function. *Clin Immunol Immunopathol.* 84:244-50.

Letterio, J. J., and A. B. Roberts. 1998. Regulation of immune responses by TGF-beta. *Annu. Rev. Immunol.* 16:137-61.

Linenberger, M. L., Maloney D. G., Bernstein I. D., 2002. Antibody directed therapies for hematological malignancies. Trends. Mol. Med. 8, 69-76.

Llera, A. S., Viedma, F., Sánchez-Madrid, F. and Tormo, J., 2001. Crystal structure of the C-type lectin-like domain from the human hematopoietic cell receptor CD69. J. Biol. Chem. 276, 7312-7319.

Lopez-Cabrera, M. et al. 1993. Molecular cloning, expression and chromosomal location of the human earliest lymphocyte activation antien AIM/CD69, a new member of the C-type lectin superfamily of signal-transmitting receptors. *J. Exp. Med.* 178:537-547.

Lubberts, E., L. A. Joosten, F. A. van de Loo, L. A. van den Gersselaar, and W. B. van den Berg. 2000. Reduction of interleukin-17-induced inhibition of chondrocyte proteoglycan synthesis in intact murine articular cartilage by interleukin-4. *Arthritis Rheum.* 43:1300-6.

Magadán, S., Valladares, M., Suarez, E., Sanjuan, I., Molina, A., Ayling C., Davies, S., Zou, X., Williams, G. T., Neuberger, M. S., Brüggemann, M., Gambón, F., Díaz-Espada, F. and González-Fernández, A., 2002. Production of antigen-specific human monoclonal antibodies from translocus mice: comparison of mice carrying IgH/kappa or IgH/kappa/lambda transloci. Biotechniques 33: 680-690.

Maini, R. N., et al. 1999. Infliximab (chimeric anti-tumour necrosis factor alpha monoclonal antibody) versus placebo in rheumatoid arthritis patients receiving concomitant methotrexate: a randomized phase III trial. ATTRACT Study Group. *Lancet* 354:1932-1939.

Mampaso, F., F. Sanchez-Madrid, R. Marcen, A. Molina, J. Pascual, T. Bricio, A. Martin, and V. Alvarez. 1993. Expression of adhesion molecules in allograft renal dysfunction. A distinct diagnostic pattern in rejection and cyclosporine nephrotoxicity. *Transplantation.* 56:687-691.

McInnes, I. B., et al. 1997. Interleukin 15 mediates T cell-dependent regulation of tumor necrosis factor-alpha production in rheumatoid arthritis. *Nat. Med.* 3:189-195.

Mc Indoe, R. A., et al. 1999. Localization of non-MHC collagen-induced arthritis susceptibility loci in DBA/lj mice. *Proc. Natl. Acad. Sci. USA* 96:2210-2214.

Molina, A., Valladares, M., Magadán, S., Sanch, D., Viedma, F., Sanjuan, I., Gambon, F., Sanchez-Madrid, F., González-Fernández, A., 2003. The use of transgenic mice for the production of a human monoclonal antibody specific for human CD69 antigen. *J. Immunol. Methods* 282(1-2):147-58.

Myers, L. K., et al. 1997. Collagen-induced arthritis, an animal model of autoimmunity. *Life Sci.* 61:1861-1878.

Nakayama, T. et al. 2002. The generation of mature, single-positive thymocytes in vivo is dysregulated by CD69 blockade or overexpression. *J. Immunol.* 168:87-94.

Nicholson, I. C., Zou, X., Popov, A. V., Cook, G. P., Corps, E. M., Humphries, S., Ayling, C., Goyenechea, B., Xian, J., Taussig, M. J., Neuberger, M. S. and Brüggemann, M., 1999. Antibody repertoires of four- and five-feature translocus mice carrying human immunoglobulin heavy chain and kappa and lambda light chain yeast artificial chromosomes. J. Immunol. 163, 6898-6909.

O'Shea, J. J., A. Ma, and P. Lipsky. 2002. Cytokines and autoimmunity. *Nat. Rev. Immunol.* 2:37-45.

Piccirillo, C. A., Y. Chang, and G. J. Prud'homme. 1998. Transforming growth factor beta-1 (TGF-β1) somatic gene therapy prevents autoimmune disease in NOD mice. *J. Immunol.* 161:3950-3956.

Powrie, F., J. Carlino, M. W. Leach, S. Mauze, and R. L. Coffinan. 1996. A critical role for transforming growth factor-beta but not interleukin 4 in the supression of T helper type 1-mediated colitis by CD45RB(low) CD4+ T cells. *J. Exp. Med.* 183:2669-2674.

Prud'homme, G. J., and C. A. Piccirillo. 2000. The inhibitory effects of transforming growth factor-beta-1 (TGF-beta1) in autoimmune diseases. *J. Autoimmun.* 14:23-42.

Remmers, E. F., et al. 1996. A geneome scan localizes five non-MHC loci controlling collagen-induced arthritis in rats. *Nat. Genet.* 14:82-85.

Rosenwald et al. 2001 Relation of Gene Expression Phenotype to Immunoglobulin Mutation Genotype in B Cell Chronic Lymphocytic Leukemia. J. Exp. Med. 11:1639.

Sancho, D., et al. 2000. Functional analysis of ligand-binding and signal transduction domains of CD69 and CD23 C-type lectin leukocyte receptors. *J. Immunol.* 165:3868-3875.

Sancho, D., et al. 1999. Activation of peripheral blood T cells by interaction and migration through endothelium: role of lymphocyte function antigen-1/intracellular adhesion molecule-1 and interleukin 15. *Blood* 93:886-896.

Sancho, D., et al. 2003. CD69 downregulates autoimmune reactivity through active transforming growth factor-θ production in collagen induced arthritis. *J. Clin. Invest.* 112: 872.

Sanchez-Mateos, P., M. Cebrian, A. Acevedo, M. Lopez-Botet, M. O. de Landazuri, and F. Sanchez-Madrid. 1989. Expression of a gp33/27,000 Mw activation inducer molecule (AIM) on human lymphoid tissues. Induction of cell proliferation on thymocytes and B lymphocytes by anti-AIM antibodies. *Immunology.* 68:72-79.

Santis, A. G., et al. 1992. Tumor necrosis factor-alpha production induced in T lymphocytes through the AIM/CD69 activation pathway. *Eur. J. Immunol.* 22:1253-1259.

Santis, A. G., López-Cabrera, M., Hamann, J., Strauss, M. and Sánchez-Madrid, F., 1994. Structure of the gene coding for the human early lymphocyte activation antigen CD69: a C-type lectin receptor evolutionarily related with the gene families of natural killer cell-specific receptors. Eur. J. Immunol. 24, 1692-1697.

Shankaran V, I. H., Bruce A T, White J M, Swanson P E, Old L J, Schreiber R D. 2001. IFNgamma and lymphocytes prevent primary tumour development and shape tumour immunogenicity. *Nature.* 410:1107-1111.

Shull, M. M., et al. 1992. Targeted disruption of mouse transforming growth factor-beta 1 gene results in multifocal inflammatory disease. *Nature* 359:693-699.

Smyth, M. J., and D. I. Godfrey. 2000. NKT cells and tumor immunity—a double-edged sword. *Nat Immunol.* 1:459-60.

Smyth, M. J., and R. W. Johnstone. 2000. Role of TNF in lymphocyte-mediated cytotoxicity. *Microsc Res Tech.* 50:196-208.

Smyth, M. J., J. M. Kelly, A. G. Baxter, H. Korner, and J. D. Sedgwick. 1998. An essential role for tumor necrosis factor in natural killer cell-mediated tumor rejection in the peritoneum. *J Exp Med.* 188:1611-9.

Smyth, M. J., K. Y. Thia, S. E. Street, D. MacGregor, D. I. Godfrey, and J. A. Trapani. 2000. Perforin-mediated cytotoxicity is critical for surveillance of spontaneous lymphoma. *J Exp Med.* 192:755-60.

Testi, R. D., et al. 1989. T cell activation via Leu-23 (CD69). *J. Immunol.* 143:1123-1128.

Testi, R., D. D'Ambrosio, R. De Maria, and A. Santoni. 1994. The CD69 receptor: a multipurpose cell-surface trigger for hematopoietic cells. *Immunol. Today.* 15:479-83.

van den Broek M E, K. D., Ossendorp F, Toes R, Vamvakas S, Lutz W K, Melief C J, Zinkemagel R M, Hengartner H. 1996. Decreased tumor surveillance in perforin-deficient mice. *J Exp Med.* 184:1781-90.

Vaughan T. J., Osbourn J. K., Tempest P. R., 1998. Human antibodies by design. Nat Biotechnol. 16, 535-539.

Walunas, T. L. et al. 1994. CTLA-4 can function as a negative regulator of T cell activation. *Immunity* 1:405-413.

Wahl, S. M., et al. 1990. Antagonistic and agonistic effects of transforming growth factor-beta and IL-1 in rheumatoid synovium. *J. Immunol.* 145:2514

Wandstrat, A., et al. 2001. The genetics of complex autoimmune diseases: non-MHC susceptibility genes. *Nat. Immunol.* 2:802-809.

Watson, W. C., et al. 1985. Genetic susceptibility to murine collagent II autoimmune arthritis. Proposed relationship to the IgG2 autoantibody subclass response, complement C5, major histocompatibility complex (MHC), and non MHC loci. *J. Exp. Med.* 162:1878-1891.

Weinblatt, M. E., et al. 1999. A trial on etanercept, a recombinant tumour necrtosis factor receptor: Fc fusion protein, in patients with rheumatoid arthritis receiving methotrexate. *N. Engl. J. Med.* 340:253-259.

Williams, R. O., et al. 2000. Evaluation of TNF-alpha and IL-1 blockade in collagen-induced arthritis and comparison with anti-TNF alpha/anti-CD4 therapy. *J. Immunol.* 165:7240-7245.

Yu, X., et al. 2001. Anti-CD69 autoantibodies cross-react with low density lipoprotein receptor related protein 2 in systemic autoimmune diseases. *J. Immunol.* 166:1360

Zajac, A. J., J. N. Blattman, K. Murali-Krishna, D. J. Sourdive, M. Suresh, J. D. Altman, and R. Ahmed. 1998. Viral immune evasion due to persistence of activated T cells without effector function. *J. Exp. Med.* 188:2199-2204.

Ziegler, S. F., et al. 1993. Molecular caracterization of early activation antigen CD69: a type II membrane glycoprotein related to a family of natural killer cell activation antigens. Eur. *J. Immunol.* 23:1643-1648.

Zingoni, A., G. Palmieri, S. Morrone, M. Carretero, M. Lopez-Botel, M. Piccoli, L. Frati, and A. Santoni. 2000. CD69-triggered ERK activation and functions are negatively regulated by CD94/NKG2-A inhibitory receptor. *Eur J Immunol.* 30:644-51.

Zou, X., Xian, J., Popov, A. V., Rosewell, I. R., Muller, M., and Brüggemann, M., 1995. Subtle differences in antibody responses and hypermutation of lambda light chains in mice with a disrupted chi constant region. Eur J. Immunol. 25, 2154-2162.

---

We claim:

1. A method for treating cancer in a subject in need thereof comprising administering an effective amount of a non-depleting antagonist anti-CD69 antibody molecule, wherein the antagonist anti-CD69 antibody molecule induces CD69 positive cells to decrease TGF-β production or down-regulate their cell surface expression of CD69, or both.

2. The method of claim 1, wherein the anti-CD69 antibody molecule is selected from the group consisting of: a humanized anti-CD69 antibody molecule, a human anti-CD69 antibody molecule, a chimeric anti-CD69 antibody molecule and a deimmunized anti-CD69 antibody molecule.

3. The method of claim 1, wherein said anti-CD69 antibody molecule is a monoclonal antibody.

4. The method of claim 1, wherein the cancer is lymphoma.

5. The method of claim 1, further comprising administering the antibody in combination with a second therapeutic agent.

* * * * *

SEQUENCE LISTING

```
<160> NUMBER OF SEQ ID NOS: 6

<210> SEQ ID NO 1
<211> LENGTH: 1702
<212> TYPE: DNA
<213> ORGANISM: Homo sapiens

<400> SEQUENCE: 1
agactcaaca agagctccag caaagacttt cactgtagct tgacttgacc tgagattaac      60
tagggaatct tgagaataaa gatgagctct gaaaattgtt tcgtagcaga gaacagctct     120
ttgcatccgg agagtggaca agaaaatgat gccaccagtc cccatttctc aacacgtcat     180
gaagggtcct tccaagttcc tgtcctgtgt gctgtaatga atgtggtctt catcaccatt     240
```

```
ttaatcatag ctctcattgc cttatcagtg ggccaataca attgtccagg ccaatacaca    300
ttctcaatgc catcagacag ccatgtttct tcatgctctg aggactgggt tggctaccag    360
aggaaatgct actttatttc tactgtgaag aggagctgga cttcagccca aatgcttgt     420 tctgaacatg gtgctactct tgctgtcatt gattctgaaa aggacatgaa ctttctaaaa    480
cgatacgcag gtagagagga cactgggtt ggactgaaaa aggaacctgg tcacccatgg     540
aagtggtcaa atggcaaaga atttaacaac tggttcaacg ttacagggtc tgacaagtgt    600 gttttctga aaacacaga ggtcagcagc atggaatgtg agaagaattt atactggata      660
tgtaacaaac cttacaaata taaggaaac atgttcactt attgactatt atagaatgga    720
actcaaggaa atctgtgtca gtggatgctg ctctgtggtc cgaagtcttc catagagact    780
ttgtgaaaaa aaattttata gtgtcttggg aattttcttc caaacagaac tatgaaaaa    840 aaggaagaaa ttccaggaaa atctgcactg tgggctttta ttgccatgag ctagaagcat    900
cacaggttga ccaataacca tgcccaagaa tgagaagaat gactatgcaa cctttggatg    960
cactttatat tatttgaat ccagaaataa tgaaataact aggcgtggac ttactattta    1020
ttgctgaatg actaccaaca gtgagagccc ttcatgcatt tgcactactg gaaggagtta    1080
gatgttggta ctagatactg aatgtaaaca aggaattat ggctggtaac ataggttttt    1140
agtctaattg aatcccttaa actcagggag catttataaa tggacaaatg cttatgaaac    1200
taagatttgt aatatttctc tcttttaga gaaatttgcc aatttacttt gttatttttc    1260
cccaaaaaga atgggatgat cgtgtattta ttttttact tcctcagctg tagacaggtc     1320
cttttcgatg gtacatattt ctttgccttt ataatctttt atacagtgtc ttacagagaa    1380
aagacataag caaagactat gaggaatatt tgcaagacat agaatagtgt tggaaaatgt    1440
gcaatatgtg atgtggcaaa tctctattag gaaatattct gtaatcttca gacctagaat    1500
aatactagtc ttataatagg tttgtgactt tcctaaatca attctattac gtgcaatact    1560
tcaatacttc atttaaaata tttttatgtg caataaaatg tatttgtttg tattttgtgt    1620
tcagtacaat tataagctgt ttttatatat gtgaaataaa agtagaataa acacaaaaaa    1680
aaaaaaaaaa aaaaaaaaaa aa                                             1702

<210> SEQ ID NO 2
<211> LENGTH: 199
<212> TYPE: PRT
<213> ORGANISM: Homo sapiens

<400> SEQUENCE: 2

Met Ser Ser Glu Asn Cys Phe Val Ala Glu Asn Ser Ser Leu His Pro
1               5                   10                  15

Glu Ser Gly Gln Glu Asn Asp Ala Thr Ser Pro His Phe Ser Thr Arg
            20                  25                  30

His Glu Gly Ser Phe Gln Val Pro Val Leu Cys Ala Val Met Asn Val
        35                  40                  45

Val Phe Ile Thr Ile Leu Ile Ile Ala Leu Ile Ala Leu Ser Val Gly
    50                  55                  60

Gln Tyr Asn Cys Pro Gly Gln Tyr Thr Phe Ser Met Pro Ser Asp Ser
65                  70                  75                  80

His Val Ser Ser Cys Ser Glu Asp Trp Val Gly Tyr Gln Arg Lys Cys
                85                  90                  95

Tyr Phe Ile Ser Thr Val Lys Arg Ser Trp Thr Ser Ala Gln Asn Ala
            100                 105                 110

Cys Ser Glu His Gly Ala Thr Leu Ala Val Ile Asp Ser Glu Lys Asp
```

```
                    115                 120                 125
Met Asn Phe Leu Lys Arg Tyr Ala Gly Arg Glu Glu His Trp Val Gly
    130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                165                 170                 175

Lys Asn Thr Glu Val Ser Ser Met Glu Cys Glu Lys Asn Leu Tyr Trp
            180                 185                 190

Ile Cys Asn Lys Pro Tyr Lys
        195

<210> SEQ ID NO 3
<211> LENGTH: 759
<212> TYPE: DNA
<213> ORGANISM: Homo sapiens

<400> SEQUENCE: 3
ctgtgctgta aaacaagag taacattttt atattaaagt taaataaagt tacaactttg    60
aagagagttt ctgcaagaca tgacacaaag ctgctagcag aaaatcaaaa cgctgattaa   120
aagaagcacg gtatgatgac caaacataaa aagtgtttta aattgttgg tgttttaata   180 acaactaata ttattactct gatagttaaa ctaactcgag attctcagag tttatgcccc   240
tatgattgga ttggtttcca aaacaaatgc tattatttct ctaaagaaga aggagattgg   300
aattcaagta atacaactg ttccactcaa catgccgacc taactataat tgacaacata   360
gaagaaatga attttcttag gcggtataaa tgcagttctg atcactggat tggactgaag   420
atggcaaaaa atcgaacagg acaatgggta catggagcta catttaccaa atcgtttggc   480
atgagaggga gtgaaggatg tgcctacctc agcgatgatg gtgcagcaac agctagatgt   540
tacaccgaaa gaaatggat ttgcaggaaa agaatacact aagttaatgt ctaagataat   600
ggggaaaata gaaaataaca ttattaagtg taaaaccagc aaagtacttt tttaattaaa   660
caaagttcga gttttgtacc tgtctggtta attctgctta cgtgtcaggc tacacataaa   720
agccacttca aagattggca aaaaaaaaaa aaaaaaaa                          759

<210> SEQ ID NO 4
<211> LENGTH: 149
<212> TYPE: PRT
<213> ORGANISM: Homo sapiens

<400> SEQUENCE: 4

Met Met Thr Lys His Lys Lys Cys Phe Ile Ile Val Gly Val Leu Ile
1               5                   10                  15

Thr Thr Asn Ile Ile Thr Leu Ile Val Lys Leu Thr Arg Asp Ser Gln
            20                  25                  30

Ser Leu Cys Pro Tyr Asp Trp Ile Gly Phe Gln Asn Lys Cys Tyr Tyr
        35                  40                  45

Phe Ser Lys Glu Glu Gly Asp Trp Asn Ser Ser Lys Tyr Asn Cys Ser
    50                  55                  60

Thr Gln His Ala Asp Leu Thr Ile Ile Asp Asn Ile Glu Glu Met Asn
65                  70                  75                  80

Phe Leu Arg Arg Tyr Lys Cys Ser Ser Asp His Trp Ile Gly Leu Lys
                85                  90                  95

Met Ala Lys Asn Arg Thr Gly Gln Trp Val His Gly Ala Thr Phe Thr
            100                 105                 110
```

Lys Ser Phe Gly Met Arg Gly Ser Glu Gly Cys Ala Tyr Leu Ser Asp
            115                 120                 125

Asp Gly Ala Ala Thr Ala Arg Cys Tyr Thr Glu Arg Lys Trp Ile Cys
        130                 135                 140

Arg Lys Arg Ile His
145

<210> SEQ ID NO 5
<211> LENGTH: 850
<212> TYPE: DNA
<213> ORGANISM: Homo sapiens

<400> SEQUENCE: 5
gaattccggc aaaatgcatg acagtaacaa tgtggagaaa gacattacac catctgaatt      60
gcctgcaaac ccaggttgtc tgcattcaaa agagcattct attaaagcta ccttaatttg     120
gcgcttattt ttcttaatca tgtttctgac aatcatagtg tgtggaatgg ttgctgcttt     180
aagcgcaata agagctaact gccatcaaga gccatcagta tgtcttcaag ctgcatgccc     240
agaaagctgg attggttttc aaagaaagtg tttctatttt tctgatgaca ccaagaactg     300
gacatcaagt cagaggtttt gtgactcaca agatgctgat cttgctcagg ttgaaagctt     360
ccaggaactg aatttcctgt tgagatataa aggcccatct gatcactgga ttgggctgag     420
cagagaacaa ggccaaccat ggaaatggat aaatggtact gaatgacaa acagtttcc      480
tatcctggga gcaggagagt gtgcctattt gaatgacaaa ggtgccagta gtgccaggca     540
ctacacagag aggaagtgga tttgttccaa atcagatata catgtctaga tgttacagca     600
aagcccccaac taatctttag aagcatattg aactgataa ctccatttta aaatgagcaa      660
agaatttatt tcttatacca acaggtatat gaaaatatgc tcaatatcac taataactgg     720
gaaaatacaa atcaaaatca tagtaaaata ttacctgttt tcatggtgct aatattacct     780
gttctcccac tgctaatgac ataccgcgaga atgagtaatt tataaataaa agagatttaa     840
ttgaaaaaaa                                                            850

<210> SEQ ID NO 6
<211> LENGTH: 191
<212> TYPE: PRT
<213> ORGANISM: Homo sapiens

<400> SEQUENCE: 6

Met His Asp Ser Asn Asn Val Glu Lys Asp Ile Thr Pro Ser Glu Leu
1               5                   10                  15

Pro Ala Asn Pro Gly Cys Leu His Ser Lys Glu His Ser Ile Lys Ala
            20                  25                  30

Thr Leu Ile Trp Arg Leu Phe Phe Leu Ile Met Phe Leu Thr Ile Ile
        35                  40                  45

Val Cys Gly Met Val Ala Ala Leu Ser Ala Ile Arg Ala Asn Cys His
    50                  55                  60

Gln Glu Pro Ser Val Cys Leu Gln Ala Ala Cys Pro Glu Ser Trp Ile
65                  70                  75                  80

Gly Phe Gln Arg Lys Cys Phe Tyr Phe Ser Asp Thr Lys Asn Trp
            85                  90                  95

Thr Ser Ser Gln Arg Phe Cys Asp Ser Gln Asp Ala Asp Leu Ala Gln
            100                 105                 110

Val Glu Ser Phe Gln Glu Leu Asn Phe Leu Arg Tyr Lys Gly Pro
            115                 120                 125

Ser Asp His Trp Ile Gly Leu Ser Arg Glu Gln Gly Gln Pro Trp Lys

```
                130                 135                 140
Trp Ile Asn Gly Thr Glu Trp Thr Arg Gln Phe Pro Ile Leu Gly Ala
145                 150                 155                 160

Gly Glu Cys Ala Tyr Leu Asn Asp Lys Gly Ala Ser Ser Ala Arg His
                165                 170                 175

Tyr Thr Glu Arg Lys Trp Ile Cys Ser Lys Ser Asp Ile His Val
                180                 185                 190
```